US007795208B2

(12) United States Patent
Sartorelli et al.

(10) Patent No.: US 7,795,208 B2
(45) Date of Patent: *Sep. 14, 2010

(54) METHODS OF USING DEACETYLASE INHIBITORS TO PROMOTE CELL DIFFERENTIATION AND REGENERATION

(75) Inventors: Vittorio Sartorelli, Bethesda, MD (US); Pier Lorenzo Puri, San Diego, CA (US)

(73) Assignees: The Salk Institute for Biological Study, La Jolla, CA (US); The United States of America as represented by the Department of Health and Human Services, Washington, DC (US)

( * ) Notice: Subject to any disclaimer, the term of this patent is extended or adjusted under 35 U.S.C. 154(b) by 647 days.

This patent is subject to a terminal disclaimer.

(21) Appl. No.: 11/800,151

(22) Filed: May 4, 2007

(65) Prior Publication Data

US 2008/0248994 A1 Oct. 9, 2008

Related U.S. Application Data

(63) Continuation of application No. 10/492,901, filed as application No. PCT/US02/33570 on Oct. 17, 2002, now Pat. No. 7,229,963.

(60) Provisional application No. 60/343,854, filed on Oct. 25, 2001, provisional application No. 60/335,705, filed on Oct. 18, 2001.

(51) Int. Cl.
*A61K 38/00* (2006.01)
*A61K 31/557* (2006.01)
*A61K 31/165* (2006.01)

(52) U.S. Cl. .............................. 514/2; 514/12; 514/574; 514/619

(58) Field of Classification Search .................. 514/2, 514/12, 574, 619
See application file for complete search history.

(56) References Cited

U.S. PATENT DOCUMENTS

| 4,443,470 | A | 4/1984 | Hodge et al. |
| 4,822,821 | A | 4/1989 | Perrine |
| 5,025,029 | A | 6/1991 | Perrine |
| 5,185,436 | A | 2/1993 | Villa et al. |
| 5,563,173 | A | 10/1996 | Yatsu et al. |
| 5,834,249 | A | 11/1998 | Furukawa et al. |
| 5,993,845 | A | 11/1999 | Geerts et al. |
| 6,030,961 | A | 2/2000 | Nudelman et al. |
| 6,043,389 | A | 3/2000 | Nudelman et al. |
| 6,110,697 | A | 8/2000 | Dulski et al. |
| 7,229,963 | B2* | 6/2007 | Sartorelli et al. ............... 514/2 |
| 2002/0183388 | A1 | 12/2002 | Gudas et al. |

FOREIGN PATENT DOCUMENTS

| EP | 0 424 055 | 7/1994 |
| EP | 0 827 742 | 3/1998 |
| WO | WO 96/39035 | 12/1996 |
| WO | WO 99/23885 | 5/1999 |
| WO | WO 99/37150 | 7/1999 |
| WO | WO 00/06720 | 2/2000 |
| WO | WO 00/08048 | 2/2000 |
| WO | WO 01/18171 | 3/2001 |

OTHER PUBLICATIONS

Blau and Epstein, "Manipulation of Myogenesis in Vitro: Reversible Inhibition by DMSO," *Cell* 17(1):95-108, 1979.
Choi et al., "14-3-3tau Associates with and Activates the MEF2d Transcription Factor During Muscle Cell Differentiation," *Nucleic Acids Res.* 29(13):2836-2842, 2001.
Davis et al., "Histone Deacetylase Inhibitors Decrease Proliferation and Modulate Cell Cycle Gene Expression in Normal Mammary Epithelial Cells," *Clinical Cancer Research* 6(11):4334-4342, 2000.
Fiszman et al., "Expression of Myogenic Differentiation and Myotube Formation by Chick Embryo Myoblasts in the Presence of Sodium Butyrate," *Exp. Cell Res.* 126:31-37, 1980.
Gabbianelli et al., "Histone switching in unicellular erythroid culture of sibling erythroid burst-forming units: kit ligand induces a does-dependent fetal hemoglobin reactivation potentiated by sodium butyrate," *Blood* 95(11):3555-3561, 2000.
Iezzi et al., "Deacetylase Inhibitors Incrase Muscle Cell Size by Promoting Myoblast Recruitment and Fusion Through Induction of Follistatin," *Developmental Cell* 6:673-684, 2004.
Johnston et al., "Sodium Butyrate Inhibits Myogenesis by Interfering with the Transcriptional Activation Function of MyoD and Myogenin," *Mol. Cell. Biol.* 12(11):5123-5130, 1992.
Lu et al., "Regulation of Skeletal Myogenesis by Association of the MEF2 Transcription Factor with Class II Histone Deacetylases," *Mol. Cell* 6(22):233-244, 2000.
Mal et al., "A Role of Histone Deacetylase HDAC1 in Modulating the Transcriptional Activity of MyoD: Inhibition of the Myogenic Program," *EMBO J.* 20(7):1739-1753, 2001.
McCafferty et al., "Induction of γ-Globin by Histone Deacetylase Inhibitors," *Blood* 90(5):2075-2083, 1997.

(Continued)

Primary Examiner—Raymond J Henley, III
(74) Attorney, Agent, or Firm—Klarquist Sparkman, LLP

(57) ABSTRACT

A method of enhancing progenitor cell differentiation, including enhancing myogenesis, neurogenesis, and hematopoiesis, by contacting a progenitor cell with an effective amount of a deacetylase inhibitor (DI). The progenitor cell can be part of cell culture, such as a cell culture used for in vitro or in vivo analysis of progenitor cell differentiation, or can be part of an organism, such as a human or other mammal. Contacting the progenitor cell with a DI can lead to enhancement of expression of terminal cell-type specific genes in the progenitor cell, such as enhancing expression of muscle-specific genes in myoblasts. Administering a DI to a subject also can provide some prophylactic or therapeutic effect for inhibiting, preventing, or treating associated with a degeneration or loss of tissue. The DI can be administered to a subject as part of a pharmaceutical composition.

45 Claims, 22 Drawing Sheets

OTHER PUBLICATIONS

O'Neil et al., "A developmental switch in H acetylation upstream of *Xist* plays a role in X chromosome inactivation," *EMBO Journal* 18(10):2897-2907, 1999.

Richon et al., "Histone Deacetylase Inhibitor Selectively Induces p21$^{WAH1}$ Expression and Gene-Associated Histone Acetylation," *Proc. Natl. Acad. Sci. USA* 97(18)10014-10019, 2000.

Sartorelli et al., "Aceylation of MyoD Directed by PCAF is Necessary for the Execution of the Muscle Program," *Mol. Cell* 4:725-734, 1999.

Schultz et al., "Reprogramming of Gene Expression During Preimplantation Development," *Journal of Experimental Zoology* 285(3):276-282, 1999.

Steinbach et al., "Histone Deacetylase Activity is Required for the Induction of the MyoD Muscle Cell Lineage in Xenopus," *Biological Chemistry* 381(9-10):1013-1016, 2000.

Youn et al., "Calcium Regulates Transcriptional Repression of Myocyte Enhancer Factor2 by Histone Deacetylase 4,"*J. Biol. Chem.* 275(29):22563-22567, 2000.

Zhang et al., "The Transcriptional Corepressor MITR is a Signal-Responsive Inhibitor of Myogenesis," *Proc. Natl. Acad. Sci. USA* 98(13):7354-7359, 2001.

Zhao et la., "The Modular Nature of Histone Deacetylase hdac4 Confers Phosphorylation-Dependent Intracellular Trafficking," *J. Biol. Chem* 276(3):35042-35048, 2001.

* cited by examiner

FIG. 1A

MHC — B tubulin myogenin

FIG. 1C

MHC — B T V tubulin myogenin

MCK — T
GAPDH

FIG. 1E

MHC — T
tubulin

FIG. 3B
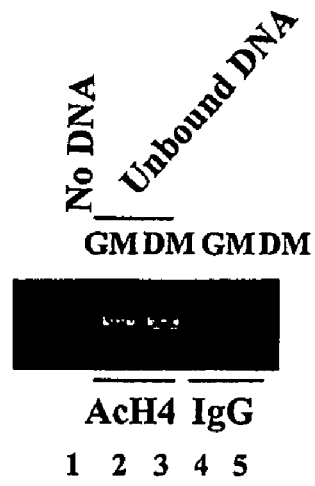
FIG. 3C
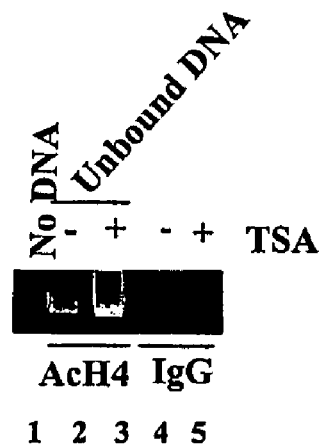
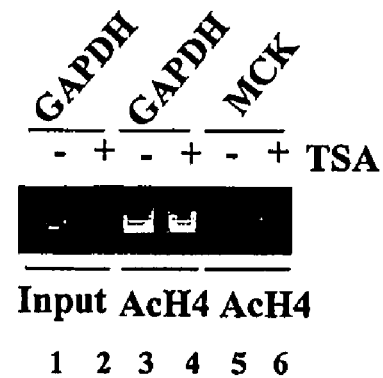

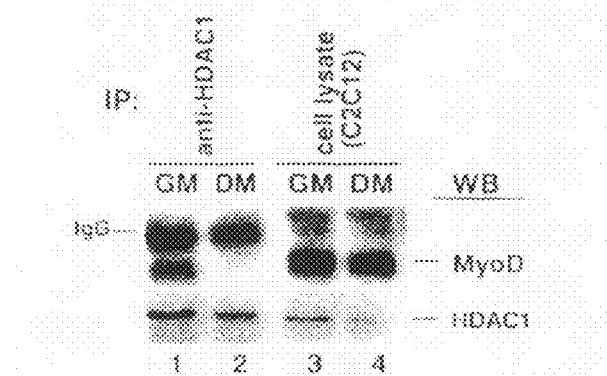
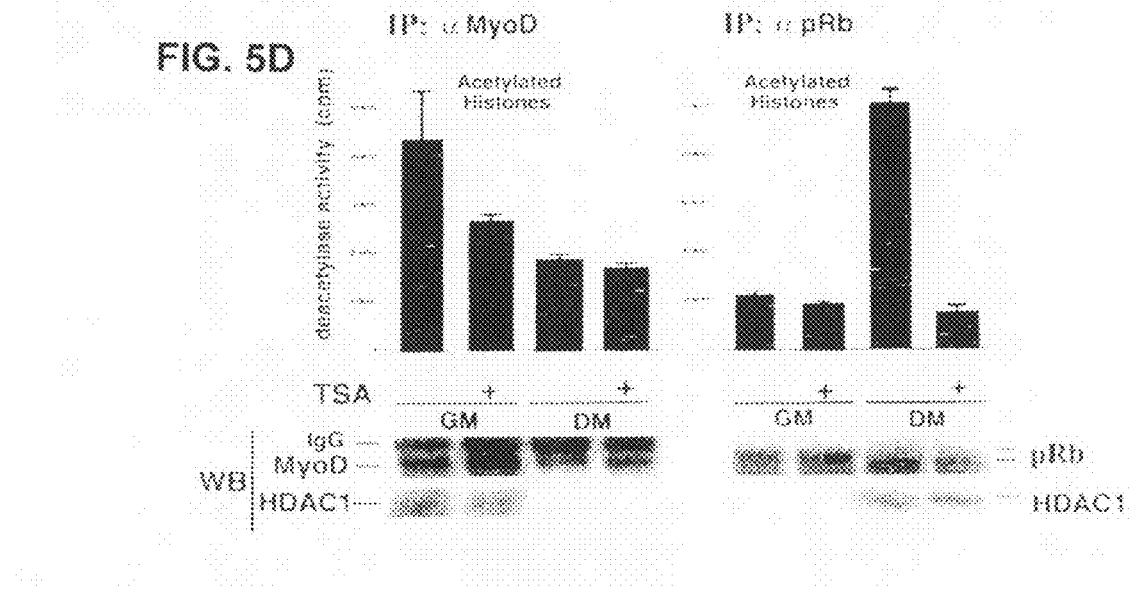

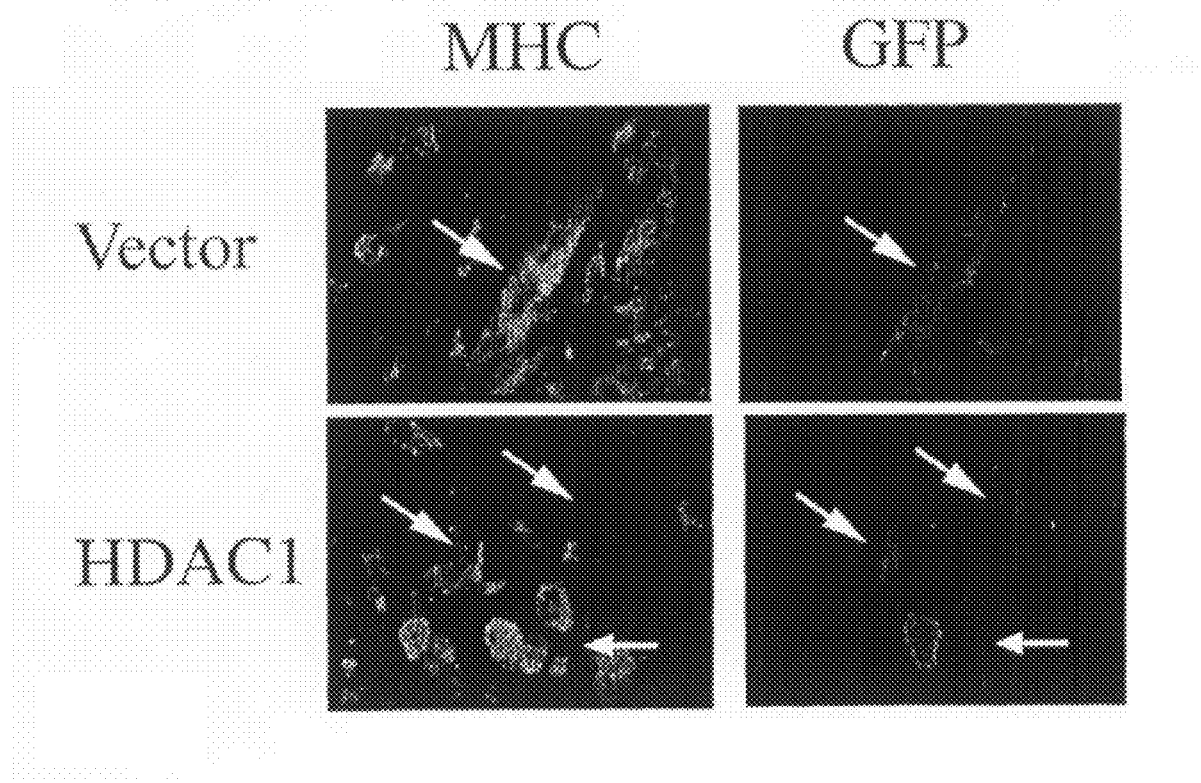

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gctcactggc atggccttcc g                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gtaggccatg aggtccacca c                                              21

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
gccactatgg gtctaggctg c                                              21
```

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cgagcttctc ctccatggtg                                                    20

<210> SEQ ID NO 5
<211> LENGTH: 2567
<212> TYPE: DNA
<213> ORGANISM: Mus musculus

<400> SEQUENCE: 5
aactataact actaactcca gagattacca gatggcgaaa ggtaaacgta ggaatcttac          60
taacaggaac caagaccact caccatcatc agaacccagc acttccactt tgcccagtcc         120
agggcacccc aacacacccg aaaacctaga cctagattta aaagcatatc tcatgatgat         180
ggtagaggac atcaagaagg actttaataa atcacttaaa gaaatacagg agaacactgc         240
taaagagtta caagtcctta agaaaaaaca ggaaaacaca atcaaacagg tagaagtcct         300
tacagaaaaa gaggaaatgt acttgctgag ttttaagatg ttttattgat gtgctatcat         360
ggctggacac cacaaaaacc aggctatgaa tatctcagtc aaggtttcaa ctgtgttacg         420
aaatgtatat caaaacctga aaacctgtc tactggacat tccctaagca cctacaatct         480
tttacaaata cttttaacttt ctgggagatt caggagtctg tgtgcaactg taaccttgca         540
tccctaagag aggaatgtgt acctcagcgc cccctagtga cattgttctg agcattttat         600
aaagacatgt gcagcattga gactatatcc caattcacac atggtgatat aacttaacac         660
aatgacttac agcacacaat taacttttat gatcatgtaa ggtttaaacg tgttaaatt          720 tttcccagat gtgtttgcaa tagataagaa aatatataca aactctcaga atcctgtatt         780
tcctcatctg tgaggatcat agggggaatg ccagcaagaa gtgtttactg gactgctgaa         840
tagcgcatcc aaaatacacc ctgctttgga ataaggcggg ccttcccaca tgtatgtagt         900
cataaagtac caggagagtg caagagagct cagattcctt tcctgtgtcc tctatttaga         960
catcccttgg acaagcaagc cagaggaat ggtgttcacc ctctgtcaag gtcacttctc         1020
ttctcttcct gcccatgatc catggtattt tctgatgtct atcattgtgg tccctgctgg        1080
ttgtcactat tgtgtcattg tagtgtctct ggggttctca agattgtaac tgattaacgg        1140
tctgatgatg aggtccgtag tcagtctctt ttagctacta atgcacaagt gagctctctg        1200
cctcattcaa actttcttct ttcatctctc agatctagat gctttaaata ataattatt        1260 acgcctataa tagtgatagc tcgtaaaagg ggtgacaaaa tgagttgtga aaatcttaga        1320
gggtcagaac acttttcttt ccggctttga gcctaacact tggggtaaat cactcactca        1380
gtgtgggtgg ctgccatgga gggtaaccta ttgtgtagca ttacatgcaa tgacaattta        1440
aaagtataaa agatttttacc tgccagcctg tgaaagacaa gttcacctga tagaattata        1500
aagcaaccat ctactgaatt tagcaattta agtcaggaga acagtggttg aaaatatcag        1560
gccagatcac agggacagtt agagtagatt tcctgtcata ttcagcaaca gctgtgcctg        1620
tatcaagtta gtcaaatcca actcggcctt tcaagggcac cgtggaggcc gatccaccca        1680
ccttctctgt ccatggggag agttttgtgg acagcatgcc tttcctccca ccttaagtaa        1740
aagtatgtag cacccacctc attggcgtca ccgctagcct tgagcctttg cctgtaccct        1800
```

-continued

```
aggaaatcat gtctgtatct ccttctgtga tgcagtagaa acactcatgg gtatcacaca    1860
gcagtctgtt gccctgcag tgcacgagtg gggagacgtc tatgacaaac cctccagaaa    1920
ggggccagac aagttcatct ctgtcctgac tccctctcct cttactacca accccttcca    1980
ctgcctaatc tgagaattca ctttcttcct catggttaga ccttcagact tcagaagaat    2040
ctatcaccag tctttctaaa actccagccc ttgcctaaga attttatct taatatctgt    2100 cactcggtgc ttccagtcac agtgtcagat ctaaagttca ctccatactc cgtaatggct    2160
ctaagcacta gcagattaat tagtcccact cgccccacac cgggctcgtt cctgtggaaa    2220
cagctttata ggcactagag tgagtaggga cctggctttg aattctgtga tgaatgatac    2280
aacacccaag ccgggagaaa cagcctccaa aaaccctgga tctccattcc ctatcagatg    2340
cttataaaga accctagatc atcccctgtc aaattattta tagatgacaa gaaatatttc    2400
taattatatc cattcacagc cacagtcagt gaatattgtg taaagagatt gccaaaaatg    2460
gttttgccaa gtaggtccgc agctaggaca gctgaggtgg ctgctgtgtt tgcagaacag    2520
cctctataaa agtgaagctg gggtgcctct gtcctgtcct tcctcaa                 2567

<210> SEQ ID NO 6
<211> LENGTH: 1481
<212> TYPE: DNA
<213> ORGANISM: Mus musculus

<400> SEQUENCE: 6
ggagcttggg ggccagtggc aggaacaagc cttttccgac ctgatggagc tgtatgagac      60
atccccctat ttctaccagg agccccactt ctatgatggg gaaaactacc ttcctgtcca     120
ccttcagggc ttcgagcccc cgggctatga gcggactgag ctcagcttaa gcccggaagc     180
ccgagggccc ctggaagaaa agggactggg gacccctgag cattgtccag ccagtgcct     240 gccgtgggca tgcaaggtgt gtaagaggaa gtctgtgtcg gtggaccgga ggagggcagc     300
cacactgagg gagaagcgca ggctcaagaa agtgaatgag gccttcgagg ccctgaagag     360
gagcaccctg ctcaaccccc accagcggct gcctaaagtg gagatcctgc gcagcgccat     420
ccagtacatt gagcgcctac aggccttgct cagctccctc aaccaggagg agcgcgatct     480
ccgctacaga ggcgggggcg ggccccagcc catggtgccc agtgaatgca actcccacag     540
cgcctcctgc agtccggagt ggggcaatgc actggagttc ggtcccaacc caggagatca     600
tttgctcgcg gctgaccta cagacgccca caatctgcac tcccttacgt ccatcgtgga     660
cagcatcacg gtggaggata tgtctgttgc cttcccagac gaaaccatgc ccaactgaga     720
ttgtctgtca ggctgggtgt gcatgtgagc ccccaagttg gtgtcaaaag ccatcacttc     780
tgtagcaggg ggcttttaag tggggctgtc ctgatgtcca gaaaacagcc ctgggctgcc     840
acaagccaga ctcccccactc cccattcaca taaggctaac cccagcccca gcgagggaat     900
ttagctgact ccttaaagca gagagcatcc tcttctgagg agagaaagat ggagtccaga     960
gagccccctt gttaatgtcc ctcagtgggg caaactcagg agcttctttt tgtttatca    1020 taatatgcct cgaattccac ccccacccc caaaatgaaa ccgtttgaga gacatgagtg    1080
ccctgacctg acaagtgtg cacatctgtt ctagtctctt cctgaagcca gttgcgtggg    1140
ctgggcctgc cctgagttga gagagaaggg ggaggagcta tccggttcca aagcctctgg    1200
gggccaagca tttgcagtgg atcttgggaa ccttccagtg cttttgtgtat tgtttattgt    1260 tttgtgtgtt gtttgtaaag ctgccgcctg accaaggtct cctgtgctga tgataccggg    1320
aacaggcagg gaaggggtg ggggctcttg gggtgacttc ttttgttaac taagcattgt    1380
```

| | |
|---|---:|
| gtggttttgc caattttttt tcttttgtaa ttcttttgct aacttatttg gatttccttt | 1440 |
| tttaaaaaat gaataaagac tggttgctat caaaaaaaaa c | 1481 |

<210> SEQ ID NO 7
<211> LENGTH: 1849
<212> TYPE: DNA
<213> ORGANISM: Mus musculus

<400> SEQUENCE: 7

| | |
|---|---:|
| ggacgcccca ggacacgact gctttcttca ccactcctct gacaggacag gacagggagg | 60 |
| aggggtagag gacagccggt gtgcattcca acccacagaa cctttgtcat tgtactgttg | 120 |
| gggttccgga gtggcagaaa gttaagacga ctctcacggc ttgggttgag ctggacccca | 180 |
| ggaactggga tatggagctt ctatcgccgc cactccggga catagacttg acaggccccg | 240 |
| acggctctct ctgctccttt gagacagcag acgacttcta tgatgacccg tgtttcgact | 300 |
| caccagacct gcgcttttt gaggacctgg acccgcgcct ggtgcacatg ggagccctcc | 360 |
| tgaaaccgga ggagcacgca cacttcccta ctgcggtgca cccaggccca ggcgctcgtg | 420 |
| aggatgagca tgtgcgcgcg cccagcgggc accaccaggc gggtcgctgc ttgctgtggg | 480 |
| cctgcaaggc gtgcaagcgc aagaccacca acgctgatcg ccgcaaggcc gccaccatgc | 540 |
| gcgagcgccg ccgcctgagc aaagtgaatg aggccttcga gacgctcaag cgctgcacgt | 600 |
| ccagcaaccc gaaccagcgg ctacccaagg tggagatcct gcgcaacgcc atccgctaca | 660 |
| tcgaaggtct gcaggctctg ctgcgcgacc aggacgccgc gcccctggcc gccgctgcct | 720 |
| tctacgcacc tggaccgctg cccccaggcc gtggcagcga gcactacagt ggcgactcag | 780 |
| atgcatccag cccgcgctcc aactgctctg atggcatgat ggattacagc ggcccccaa | 840 |
| gcggccccg gcggcagaat ggctacgaca ccgcctacta cagtgaggcg cgcgcgagt | 900 |
| ccaggccagg aagagtgcg gctgtgtcga gcctcgactg cctgtccagc atagtggagc | 960 |
| gcatctccac agacagcccc gctgcgcctg cgctgctttt ggcagatgca ccaccagagt | 1020 |
| cgcctccggg tccgccagag ggggcatccc taagcgacac agaacaggga acccagaccc | 1080 |
| cgtctcccga cgccgcccct cagtgtcctg caggctcaaa ccccaatgcg atttatcagg | 1140 |
| tgctttgaga gatcgactgc agcagcagag ggcgcaccac cgtaggcact cctggggatg | 1200 |
| gtgtccctgg ttcttcacgc ccaaaagatg aagcttaaat gacactcttc ccaactgtcc | 1260 |
| tttcgaagcc gttcttccag agggaaggga agagcagaag tctgtcctag atccagcccc | 1320 |
| aaagaaagga catagtcctt tttgttgttg ttgttgtagt ccttcagttg tttgtttgtt | 1380 |
| ttttcatgcg gctcacagcg aaggccactt gcactctggc tgcacctcac tgggccagag | 1440 |
| ctgatccttg agtggccagg cgctcttcct ttcctcatag cacaggggtg agccttgcac | 1500 |
| acctaagccc tgccctccac atcctttgt ttgtcacttt ctggagccct cctggcaccc | 1560 |
| actttccc acagcttgcg gaggccactc aggtctcagg tgtaacaggt gtaaccatac | 1620 |
| cccactctcc cccttcccgc ggttcaggac cacttatttt tttatataag acttttgtaa | 1680 |
| tctattcgtg taaataagag ttgcttggcc agagcggag cccttgggc tatatttatc | 1740 |
| tcccaggcat gctgtgtagt gcaacaaaaa ctttgtatgt ttattcctca agcgggcgag | 1800 |
| cctcgaggct cgctcgctca ggtgttggaa ataaagacgc taatttata | 1849 |

<210> SEQ ID NO 8
<211> LENGTH: 4101
<212> TYPE: DNA

<213> ORGANISM: Mus musculus
<220> FEATURE:
<221> NAME/KEY: misc_feature
<222> LOCATION: (309)..(310)
<223> OTHER INFORMATION: n is a, c, g, or t

<400> SEQUENCE: 8

| | | | | | |
|---|---|---|---|---|---|
| cagctgaggt | gcaaaaggct | cctgtcatat | tgtgtcctgc | tctggtctgc | cttcacagct | 60 |
| tgggggccac | ctagcccacc | tctccctagg | gatgagagca | gccactatgg | gtctaggctg | 120 |
| cccatgtaag | gaggcaaggc | ctggggacac | ccgagatgcc | tggttataat | taacccagac | 180 |
| atgtggctgc | tcccccccc | caacacctgc | tgcctgagcc | tcaccccac | cccggtgcct | 240 |
| gggtcttagg | ctctgtacac | catggaggag | aagctcgctc | taaaataac | cctgtccctg | 300 |
| gtggatccnn | tccggagggg | caggctgagg | gcggccactt | ccctcagccg | cagtttgttt | 360 |
| tcccaagaat | ggttttctg | cttctgtagc | ttttcctgtc | aattctgcca | tggtggagca | 420 |
| gcctgcactg | ggcttctggg | agaaaccaaa | ccgggttcta | acctttcagc | tacagtcatt | 480 |
| gcctttcctg | tagatgggcg | actacagccc | cacccccacc | cccgtctcct | gtatccttcc | 540 |
| tgggcctggg | gatcctaggc | tttcactgga | aatttccccc | caggtgctgt | aggctagagt | 600 |
| cacggctccc | aagaacagtg | cttgcctggc | atgcatggtt | ctgaacctcc | aactgcaaaa | 660 |
| aatgacacat | accttgaccc | ttggaaggct | gaggcagggg | gattgccatg | agtgcaaagc | 720 |
| cagactgggt | ggcatagtta | gaccctgtct | caaaaaacca | aaacaatta | aataactaaa | 780 |
| gtcaggcaag | taatcctact | caggagactg | aggcagaggg | attgttacat | gtctgaggcc | 840 |
| agcctggact | acatagggtt | tcaggctagc | cctgtctaca | gagtaaggcc | ctatttcaaa | 900 |
| aacacaaaca | aaatggttct | cccagctgct | aatgctcacc | aggcaatgaa | gcctggtgag | 960 |
| cattagcaat | gaaggcaatg | aaggagggtg | ctggctacat | caggctgtgg | gggactgagg | 1020 |
| gcaggctgta | acaggcttgg | ggggccaggggc | ttatacgtgc | ctgggactcc | caaagtatta | 1080 |
| ctgttccatg | ttcccggcga | agggccagct | gtccccgcc | agctagactc | agcacttagt | 1140 |
| ttaggaacca | gtgagcaagt | cagcccttgg | ggcagcccat | acaaggccat | ggggctgggc | 1200 |
| aagctgcacg | cctgggtccg | gggtgggcac | ggtgcccggg | caacgagctg | aaagctcatc | 1260 |
| tgctctcagg | ggcccctccc | tggggacagc | ccctcctggc | tagtcacacc | ctgtaggctc | 1320 |
| ctctatataa | cccaggggca | cagggctgc | ccccgggtca | ccaccacctc | cacagcacag | 1380 |
| acagacactc | aggagccagc | cagccaggta | gggactgaga | gaaatcactg | gggtgggagt | 1440 |
| ggggcgtggg | agtccaaggg | tctgctcacc | cagtcatgtt | atggttgtgg | attttgcagc | 1500 |
| acaagttgtg | gggacaaatg | tctgggacac | ctaggtctca | atagccacca | agtgtcccct | 1560 |
| ccttgcaagg | cagggtgggc | tggaacttag | tttagcagag | ttaatggccc | acacaaagac | 1620 |
| agttgtctca | gtgacacctg | tcagtggccc | tttaactttg | taaccatgtg | gacctgtgtt | 1680 |
| gcagctctgt | gaccttgtgt | ctcactgtcc | tggtctgtct | ctatgtctct | ctgtctctct | 1740 |
| gtctctctgt | ctctatctct | ctctttctgt | ctctctctct | ccctctctct | ttcgagatgg | 1800 |
| gtcagggggg | gtgtgttct | ctgcgtagcc | ctggctgtcc | tggaactcac | tctgtagacc | 1860 |
| agcctggcct | cgaactcaga | aatccacctg | cctcccaagt | gctgggatta | aaggcatgtg | 1920 |
| ccaccaccgc | ccggcggtct | ttcttgtgtg | agacttgggg | gctctcactc | ttacaggccc | 1980 |
| ctgctttcct | ttgagtcctt | ctgtctggct | gtctctggga | tcttgaaggc | aggaaggact | 2040 |
| acatgactca | gttacctgg | agatcttaga | gaatctgtga | tgagtttggg | gacttccgaa | 2100 |
| gctttctgct | tctgcggtct | tgcctcggtg | tcctgtctcc | tggggtgccc | tgaggagggg | 2160 |

-continued

```
gtagcggagg atacagaacc ttctaaggga gagatctggg ctgggagcct ggggtgtcct    2220
tgagtcccag agcctggctg tgtgtcctcc tggccacccc agcccacctg tcccaatgct    2280
gacttagtgc aaggcgagcc agcaaggagg gaggacaggt ggcagtgggg ggtgaggagc    2340
atctaaaaat agccacaaag tagcagcttc aagggctttg ggtctctgtc tgccccacac    2400
tcttctctca gcttggtcca ccttccctct caccttcctc tgaggccccc ttccagcccc    2460
gatggaggcc tgatgtcccc catggtcagt gcttcaggga tctagtcaat aaaattaata    2520
atgaaaaaca acagtaataa aatacacgtg acgtgactgg ggcagcttag ggcttagttc    2580
aaatcccagt gttcacaccc tttaaaagac aagacaaaac aaaacagctg gctgtggggg    2640
agaacatcag aatcccctg ggaggtgggg acagggatc tgtggggctc catggccagg     2700
cagcctagct ccaggcctgc gagagaccct acctcaagat aaaaataaaa taaaataaaa    2760
taaaataaaa taaatatata aaataacaat gttgcagcac ctgaggtcac cactggaatg    2820
tgcacacctg tgaatacatg agcctgcact acaaacaaaa atattaacag taactgttag    2880
aatcccagct gcaacttcat gccaggtgcc aggtccatgc taatcagtca gggactggaa    2940
ctcagagatc tcctgggaag cttcagtctc acagattcaa atgccagaga gatctagtca    3000
cagcctgggg cccagagcag tgacttagga gagacgtgcc ttttaaagtg gaccttgtag    3060
acagccagag gtggagggac tgggagaggt ggctgaagcc tccagactca ttcccacacc    3120
cacatctgga ctaatttgga tcaagaatct caggggagcc cttatggctt ttctcaggtg    3180
tgcacatata atctttacca gggtcctcac acagagcctg tcagattggt tttcaatttc    3240
tgtgataaac accatgacca agacaaccta gaaaagagaa agcattaatt tgggactcag    3300
ggttctggag cggcagggag gtgggtatgg tgctggagca gaggctggaa gctcacatct    3360
ttatcaacaa ccagaggcag tgagagccac ttgggaatgg ggtggctttt cggaaatctc    3420
aaagcccaca agcaatggca cacctcctcc aacaaggcca cacctccgaa tccttcccaa    3480
acagttccac cgactgggga ccaaacattc aaatatgtga gtctgaggct cttctcattc    3540
aaatcaccac agacccaaga acaatcgaat aaaatatttg tgttatgtgc caggcatggc    3600
gaggcgcttt tcttgtcttt taatccctcc caagaggtca gcgatgccac agtctccatg    3660
ttacagatga gtgaacagga aagtcaaaca ggctcctcag agtcacgcgg ctgcttgtaa    3720
gttgcaaagc cgaaattcga acccagacca tctgatccag atcctttgct gcttttattc    3780
atctttttat tttattttat tttattttat tttattttat tttattttat tttattttat    3840
tttaattcct ggtggcaggg tttcgtagtc caggctaccc ttgaattcac tgcaacctcc    3900
tgcctcagtt tcagagtgtt ggaattacaa gcaatggacc atcatgccca gttcctttgg    3960
gtagagatag agacctgtgt aggagcccag actcggctg gtctccagct ctctacgtag     4020
atgaagatga ccttgaactg ctgggatttc aggcatgagc agccacaccc agatttctga    4080
gagccaaact gttacccagg g                                              4101
```

<210> SEQ ID NO 9
<211> LENGTH: 1228
<212> TYPE: DNA
<213> ORGANISM: Mus musculus

<400> SEQUENCE: 9

```
acagccgcat cttcttgtgc agtgccagcc tcgtcccgta gacaaaatgg tgaaggtcgg     60
tgtgaacgga tttggccgta ttgggcgcct ggtcaccagg gctgccattt gcagtggcaa    120
```

| | |
|---|---:|
| agtggagatt gttgccatca acgacccctt cattgacctc aactacatgg tctacatgtt | 180 |
| ccagtatgac tccactcacg gcaaattcaa cggcacagtc aaggccgaga atgggaagct | 240 |
| tgtcatcaac gggaagccca tcaccatctt ccaggagcga gacccactaa acatcaaatg | 300 |
| gggtgaggcc ggtgctgagt atgtcgtgga gtctactggt gtcttcacca ccatggagaa | 360 |
| ggccggggcc cacttgaagg gtggagccaa acgggtcatc atctccgccc cttctgccga | 420 |
| tgcccccatg tttgtgatgg gtgtgaacca cgagaaatat gacaactcac tcaagattgt | 480 |
| cagcaatgca cctgcacca ccaactgctt agccccctg gccaaggtca tccatgacaa | 540 |
| ctttggcatt gtgaagggc tcatgaccac agtccatgcc atcactgcca cccagaagac | 600 |
| tgtggatggc ccctctggaa agctgtggcg tgatggccgt ggggctgccc agaacatcat | 660 |
| ccctgcatcc actggtgctg ccaaggctgt gggcaaggtc atcccagagc tgaacgggaa | 720 |
| gctcactggc atggccttcc gtgttcctac ccccaatgtg tccgtcgtgg atctgacgtg | 780 |
| ccgcctggag aaacctgcca agtatgatga catcaagaag gtggtgaagc aggcatctga | 840 |
| gggcccactg aagggcatct tgggctacac tgaggaccag gttgtctcct gcgacttcaa | 900 |
| cagcaactcc cactcttcca ccttcgatgc cggggctggc attgctctca atgacaactt | 960 |
| tgtcaagctc atttcctggt atgacaatga atacggctac agcaacaggg tggtggacct | 1020 |
| catggcctac atggcctcca aggagtaaga aaccctggac cacccacccc agcaaggaca | 1080 |
| ctgagcaaga gaggccctat cccaactcgg cccccaacac tgagcatctc cctcacaatt | 1140 |
| tccatcccag accccataa taacaggagg ggcctaggga gccctcccta ctctcttgaa | 1200 |
| taccatcaat aaagttcgct gcacccac | 1228 |

<210> SEQ ID NO 10
<211> LENGTH: 853
<212> TYPE: DNA
<213> ORGANISM: Homo sapiens

<400> SEQUENCE: 10

| | |
|---|---:|
| actcagggac cggagcagcc ctcaactcac tcttcagctt ccctgctgtg ttgctgccca | 60 |
| gccgctccat catgtccttc agtgctgacc agattgctga attcaaggag gcatttctcc | 120 |
| tgtttgacag aacaggtgat tccaagatca ccttaagcca ggtcggtgat gtccttcgag | 180 |
| ctctgggcac aaatcccacc aatgcagagg tcaggaaagt tctgggaaac cccagcaatg | 240 |
| aagagctgaa tgccaagaaa attgagtttg aacaatttct gcctatgatg caagccattt | 300 |
| ccaacaacaa ggaccaggcc acctatgaag actttgttga gggtctgcgt gtctttgaca | 360 |
| aggaaggcaa tggcacagtc atgggtgctg aactccgcca tgttctagcc accctgggtg | 420 |
| aaaagatgaa gaggaagaa gtggaagccc tgatggcagg tcaagaagac tccaatggct | 480 |
| gcatcaacta cgaagctttt gtcaagcaca tcatgtctat ctgaatggag ctctcaagaa | 540 |
| caagcattgt ttaggaagac tggctggaaa cttatttaa tcacacccat gacaaactct | 600 |
| ccagatctgt ttaccatcat tcaggaaaac aaagcaatct ggacggttca agactgagca | 660 |
| actcccctgaa ttttataca tcttcagttt ttctctgaat tgaattcata ccacacaaac | 720 |
| aaatgtctgc tgctctagat gagaagaata aaatattgac aatctcaaat ccaagcagcc | 780 |
| ttctttatta tctaccatga atcaacgaaa cattcttaaa acaataaatc aataaacaat | 840 |
| tttggtcagt ctg | 853 |

<210> SEQ ID NO 11
<211> LENGTH: 921

```
<212> TYPE: PRT
<213> ORGANISM: Mus musculus

<400> SEQUENCE: 11

Met Pro Pro Lys Ala Pro Arg Arg Ala Ala Ala Glu Pro Pro Pro
1               5                   10                  15

Pro Pro Pro Pro Pro Arg Glu Asp Asp Pro Ala Gln Asp Ser Gly
            20                  25                  30

Pro Glu Glu Leu Pro Leu Ala Arg Leu Glu Phe Glu Ile Glu Glu
            35                  40                  45

Pro Glu Phe Ile Ala Leu Cys Gln Lys Leu Lys Val Pro Asp His Val
50                  55                  60

Arg Glu Arg Ala Trp Leu Thr Trp Glu Lys Val Ser Ser Val Asp Gly
65                  70                  75                  80

Ile Leu Glu Gly Tyr Ile Gln Lys Lys Lys Glu Leu Trp Gly Ile Cys
                85                  90                  95

Ile Phe Ile Ala Ala Val Asp Leu Asp Glu Met Pro Phe Thr Phe Thr
            100                 105                 110

Glu Leu Gln Lys Ser Ile Glu Thr Ser Val Tyr Lys Phe Phe Asp Leu
        115                 120                 125

Leu Lys Glu Ile Asp Thr Ser Thr Lys Val Asp Asn Ala Met Ser Arg
130                 135                 140

Leu Leu Lys Lys Tyr Asn Val Leu Cys Ala Leu Tyr Ser Lys Leu Glu
145                 150                 155                 160

Arg Thr Cys Glu Leu Ile Tyr Leu Thr Gln Pro Ser Ser Ala Leu Ser
                165                 170                 175

Thr Glu Ile Asn Ser Met Leu Val Leu Lys Ile Ser Trp Ile Thr Phe
            180                 185                 190

Leu Leu Ala Lys Gly Glu Val Leu Gln Met Glu Asp Asp Leu Val Ile
        195                 200                 205

Ser Phe Gln Leu Met Leu Cys Val Val Asp Tyr Phe Ile Lys Phe Ser
210                 215                 220

Pro Pro Ala Leu Leu Arg Glu Pro Tyr Lys Thr Ala Ala Ile Pro Ile
225                 230                 235                 240

Asn Gly Ser Pro Arg Thr Pro Arg Arg Gly Gln Asn Arg Ser Ala Arg
                245                 250                 255

Ile Ala Lys Gln Leu Glu Asn Asp Thr Arg Ile Ile Glu Val Leu Cys
            260                 265                 270

Lys Glu His Glu Cys Asn Ile Asp Glu Val Lys Asn Val Tyr Phe Lys
        275                 280                 285

Asn Phe Ile Pro Phe Ile Asn Ser Leu Gly Ile Val Ser Ser Asn Gly
290                 295                 300

Leu Pro Glu Val Glu Ser Leu Ser Lys Arg Tyr Glu Glu Val Tyr Leu
305                 310                 315                 320

Lys Asn Lys Asp Leu Asp Ala Arg Leu Phe Leu Asp His Asp Lys Thr
                325                 330                 335

Leu Gln Thr Asp Pro Ile Asp Ser Phe Glu Thr Glu Arg Thr Pro Arg
            340                 345                 350

Lys Asn Asn Pro Asp Glu Glu Ala Asn Val Val Thr Pro His Thr Pro
        355                 360                 365

Val Arg Thr Val Met Asn Thr Ile Gln Gln Leu Met Val Ile Leu Asn
370                 375                 380

Ser Ala Ser Asp Gln Pro Ser Glu Asn Leu Ile Ser Tyr Phe Asn Asn
385                 390                 395                 400
```

```
Cys Thr Val Asn Pro Lys Glu Asn Ile Leu Lys Arg Val Lys Asp Val
            405                 410                 415
Gly His Ile Phe Lys Glu Lys Phe Ala Asn Ala Val Gly Gln Gly Cys
            420                 425                 430
Val Asp Ile Gly Val Gln Arg Tyr Lys Leu Gly Val Arg Leu Tyr Tyr
            435                 440                 445
Arg Val Met Glu Ser Met Leu Lys Ser Glu Glu Arg Leu Ser Ile
            450                 455                 460
Gln Asn Phe Ser Lys Leu Leu Asn Asp Asn Ile Phe His Met Ser Leu
465                 470                 475                 480
Leu Ala Cys Ala Leu Glu Val Val Met Ala Thr Tyr Ser Arg Ser Thr
            485                 490                 495
Leu Gln His Leu Asp Ser Gly Thr Asp Leu Ser Phe Pro Trp Ile Leu
            500                 505                 510
Asn Val Leu Asn Leu Lys Ala Phe Asp Phe Tyr Lys Val Ile Glu Ser
            515                 520                 525
Phe Ile Lys Val Glu Ala Asn Leu Thr Arg Glu Met Ile Lys His Leu
            530                 535                 540
Glu Arg Cys Glu His Arg Ile Met Glu Ser Leu Ala Trp Leu Ser Asp
545                 550                 555                 560
Ser Pro Leu Phe Asp Leu Ile Lys Gln Ser Lys Asp Gly Glu Gly Pro
            565                 570                 575
Asp Asn Leu Glu Pro Ala Cys Pro Leu Ser Leu Pro Leu Gln Gly Asn
            580                 585                 590
His Thr Ala Ala Asp Met Tyr Leu Ser Pro Leu Arg Ser Pro Lys Lys
            595                 600                 605
Arg Thr Ser Thr Thr Arg Val Asn Ser Ala Ala Asn Thr Glu Thr Gln
            610                 615                 620
Ala Ala Ser Ala Phe His Thr Gln Lys Pro Leu Lys Ser Thr Ser Leu
625                 630                 635                 640
Ala Leu Phe Tyr Lys Lys Val Tyr Arg Leu Ala Tyr Leu Arg Leu Asn
            645                 650                 655
Thr Leu Cys Ala Arg Leu Leu Ser Asp His Pro Glu Leu Glu His Ile
            660                 665                 670
Ile Trp Thr Leu Phe Gln His Thr Leu Gln Asn Glu Tyr Glu Leu Met
            675                 680                 685
Arg Asp Arg His Leu Asp Gln Ile Met Met Cys Ser Met Tyr Gly Ile
            690                 695                 700
Cys Lys Val Lys Asn Ile Asp Leu Lys Phe Lys Ile Ile Val Thr Ala
705                 710                 715                 720
Tyr Lys Asp Leu Pro His Ala Ala Gln Glu Thr Phe Lys Arg Val Leu
            725                 730                 735
Ile Arg Glu Glu Glu Phe Asp Ser Ile Ile Val Phe Tyr Asn Ser Val
            740                 745                 750
Phe Met Gln Arg Leu Lys Thr Asn Ile Leu Gln Tyr Ala Ser Thr Arg
            755                 760                 765
Pro Pro Thr Leu Ser Pro Ile Pro His Ile Pro Arg Ser Pro Tyr Lys
            770                 775                 780
Phe Ser Ser Ser Pro Leu Arg Ile Pro Gly Gly Asn Ile Tyr Ile Ser
785                 790                 795                 800
Pro Leu Lys Ser Pro Tyr Lys Ile Ser Glu Gly Leu Pro Thr Pro Thr
            805                 810                 815
```

```
Lys Met Thr Pro Arg Ser Arg Ile Leu Val Ser Ile Gly Glu Ser Phe
              820                 825                 830

Gly Thr Ser Glu Lys Phe Gln Lys Ile Asn Gln Met Val Cys Asn Ser
          835                 840                 845

Asp Arg Val Leu Lys Arg Ser Ala Glu Gly Gly Asn Pro Pro Lys Pro
      850                 855                 860

Leu Lys Asn Val Arg Phe Asp Ile Glu Gly Ala Asp Glu Ala Asp Gly
865                 870                 875                 880

Ser Lys His Leu Pro Ala Glu Ser Lys Phe Gln Gln Lys Leu Ala Glu
              885                 890                 895

Met Thr Ser Thr Arg Thr Arg Met Gln Lys Gln Arg Met Asn Glu Ser
              900                 905                 910

Lys Asp Val Ser Asn Lys Glu Glu Lys
              915                 920

<210> SEQ ID NO 12
<211> LENGTH: 2091
<212> TYPE: DNA
<213> ORGANISM: Homo sapiens

<400> SEQUENCE: 12
gagcggagcc gcgggcggga gggcggacgg accgactgac ggtagggacg ggaggcgagc    60
aagatggcgc agacgcaggg cacccggagg aaagtctgtt actactacga cggggatgtt   120
ggaaattact attatggaca aggccaccca atgaagcctc accgaatccg catgactcat   180
aatttgctgc tcaactatgg tctctaccga aaaatggaaa tctatcgccc tcacaaagcc   240
aatgctgagg agatgaccaa gtaccacagc gatgactaca ttaaattctt gcgctccatc   300
cgtccagata acatgtcgga gtacagcaag cagatgcaga gattcaacgt tggtgaggac   360
tgtccagtat tcgatggcct gtttgagttc tgtcagttgt ctactggtgg ttctgtggca   420
agtgctgtga aacttaataa gcagcagacg gacatcgctg tgaattgggc tggggggcctg   480 caccatgcaa agaagtccga ggcatctggc ttctgttacg tcaatgatat cgtcttggcc   540
atcctggaac tgctaaagta tcaccagagg gtgctgtaca ttgacattga tattcaccat   600
ggtgacggcg tggaagaggc cttctacacc acggaccggg tcatgactgt gtccttttcat   660 aagtatggag agtacttccc aggaactggg gacctacggg atatcggggc tggcaaaggc   720
aagtattatg ctgttaacta cccgctccga gacgggattg atgacgagtc ctatgaggcc   780 atttcaagc cggtcatgtc caaagtaatg gagatgttcc agcctagtgc ggtggtctta   840
cagtgtggct cagactccct atctggggat cggttaggtt gcttcaatct aactatcaaa   900
ggacacgcca gtgtgtggaa atttgtcaag agctttaacc tgcctatgct gatgctggga   960
ggcggtggtt acaccattcg taacgttgcc cggtgctgga catatgagac agctgtggcc  1020
ctggatacgg agatccctaa tgagcttcca tacaatgact actttgaata ctttggacca  1080
gatttcaagc tccacatcag tccttccaat atgactaacc agaacacgaa tgagtacctg  1140
gagaagatca acagcgact gtttgagaac cttagaatgc tgccgcacgc acctgggtc  1200 caaatgcagg cgattcctga ggacgccatc cctgaggaga gtggcgatga ggacgaagac  1260
gaccctgaca gcgcatctc gatctgctcc tctgacaaac gaattgcctg tgaggaagag  1320
ttctccgatt ctgaagagga gggagagggg ggccgcaaga actcttccaa cttcaaaaaa  1380
gccaagagag tcaaaacaga ggatgaaaaa gagaaagacc cagagagaa gaaagaagtc  1440 accgaagagg agaaaaccaa ggaggagaag ccagaagcca aggggtcaa ggaggaggtc  1500
```

| | |
|---|---|
| aagttggcct gaatggacct ctccagctct ggcttcctgc tgagtccctc acgtttcttc | 1560 |
| cccaacccct cagattttat attttctatt tctctgtgta tttatataaa aatttattaa | 1620 |
| atataaatat ccccagggac agaaaccaag gccccgagct cagggcagct gtgctgggtg | 1680 |
| agctcttcca ggagccacct tgccacccat tcttcccgtt cttaactttg aaccataaag | 1740 |
| ggtgccaggt ctgggtgaaa gggatacttt tatgcaacca taagacaaac tcctgaaatg | 1800 |
| ccaagtgcct gcttagtagc tttggaaagg tgcccttatt gaacattcta gaagggtgg | 1860 |
| ctgggtcttc aaggatctcc tgttttttc aggctcctaa agtaacatca gccattttta | 1920 |
| gattggttct gttttcgtac cttcccactg gcctcaagtg agccaagaaa cactgcctgc | 1980 |
| cctctgtctg tcttctccta attctgcagg tggaggttgc tagtctagtt tccttttga | 2040 |
| gatactattt tcattttgt gagcctcttt gtaataaaat ggtacatttc t | 2091 |

<210> SEQ ID NO 13
<211> LENGTH: 8459
<212> TYPE: DNA
<213> ORGANISM: Homo sapiens

<400> SEQUENCE: 13

| | |
|---|---|
| ggaggttgtg gggccgccgc cgcggagcac cgtccccgcc gccgcccgag cccgagcccg | 60 |
| agcccgcgca cccgcccgcg ccgccgccgc gccgcccga acagcctccc agcctgggcc | 120 |
| cccggcggcg ccgtggccgc gtcccggctg tcgccgcccg agcccgagcc cgcgcgccgg | 180 |
| cgggtggcgg cgcaggctga ggagatgcgg cgcggagcgc cggagcaggg ctagagccgg | 240 |
| ccgccgccgc ccgccgcggt aagcgcagcc ccggcccggc gcccgcgggc cattgtccgc | 300 |
| cgcccgcccc gcgcccgcg cagcctgcag gccttggagc ccgcggcagg tggacgccgc | 360 |
| cggtccacac ccgccccgcg cgcggccgtg ggaggcgggg gccagcgctg gccgcgcgcc | 420 |
| gtgggacccg ccggtcccca gggccgcccg gccccttctg gaccttttcca cccgcgccgc | 480 |
| gaggcggctt cgcccgccgg ggcggggggcg cggggggtggg cacggcaggc agcggcgccg | 540 |
| tctcccggtg cggggcccgc gcccccccgag caggttcatc tgcagaagcc agcggacgcc | 600 |
| tctgttcaac ttgtgggtta cctggctcat gagaccttgc cggcgaggct cggcgcttga | 660 |
| acgtctgtga cccagccctc accgtcccgg tacttgtatg tgttggtggg agtttggagc | 720 |
| tcgttggagc tatcgtttcc gtggaaattt tgagccattt cgaatcactt aaaggagtgg | 780 |
| acattgctag caatgagctc ccaaagccat ccagatggac tttctggccg agaccagcca | 840 |
| gtggagctgc tgaatcctgc ccgcgtgaac cacatgccca gcacggtgga tgtggccacg | 900 |
| gcgctgcctc tgcaagtggc cccctcggca gtgcccatgg acctgcgcct ggaccaccag | 960 |
| ttctcactgc ctgtggcaga gccggccctg cgggagcagc agctgcagca ggagctcctg | 1020 |
| gcgctcaagc agaagcagca gatccagagg cagatcctca tcgctgagtt ccagaggcag | 1080 |
| cacgagcagc tctcccggca gcacgaggcg cagctccacg agcacatcaa gcaacaacag | 1140 |
| gagatgctgg ccatgaagca ccagcaggag ctgctggaac accagcggaa gctggagagg | 1200 |
| caccgccagg agcaggagct ggagaagcag caccgggagc agaagctgca gcagctcaag | 1260 |
| aacaaggaga agggcaaaga gagtgccgtg gccagcacag aagtgaagat gaagttacaa | 1320 |
| gaatttgtcc tcaataaaaa gaaggcgctg gcccaccgga atctgaacca ctgcatttcc | 1380 |
| agcgacccctc gctactggta cgggaaaacg cagcacagtt cccttgacca gagttctcca | 1440 |
| ccccagagcg gagtgtcgac ctcctataac cacccggtcc tgggaatgta cgacgccaaa | 1500 |
| gatgacttcc ctcttaggaa aacagcttct gaaccgaatc tgaaattacg gtccaggcta | 1560 |

-continued

```
aagcagaaag tggccgaaag acggagcagc ccctgttac gcaggaaaga cgggccagtg  1620
gtcactgctc taaaaagcg tccgttggat gtcacagact ccgcgtgcag cagcgcccca  1680
ggctccggac ccagctcacc caacaacagc tccgggagcg tcagcgcgga aacggtatc   1740
gcgcccgccg tccccagcat cccggcggag acgagtttgg cgcacagact tgtggcacga  1800
gaaggctcgg ccgctccact tccctctac acatcgccat ccttgcccaa catcacgctg   1860
ggcctgcctg ccaccggccc ctctgcgggc acggcgggcc agcaggacac cgagagactc  1920
acccttcccg ccctccagca gaggctctcc cttttcccg gcacccacct cactccctac   1980
ctgagcacct cgcccttgga gcgggacgga ggggcagcgc acagccctct tctgcagcac  2040
atggtcttac tggagcagcc accggcacaa gcaccctcg tcacaggcct gggagcactg    2100
cccctccacg cacagtcctt ggttggtgca gaccgggtgt ccccctccat ccacaagctg  2160
cggcagcacc gcccactggg gcggacccag tcggccccgc tgcccagaa cgcccaggct    2220
ctgcagcacc tggtcatcca gcagcagcat cagcagtttc tggagaaaca caagcagcag  2280
ttccagcagc agcaactgca gatgaacaag atcatcccca agccaagcga gccagcccgg  2340
cagccggaga gccacccgga ggagacggag gaggagctcc gtgagcacca ggctctgctg  2400
gacgagccct acctggaccg gctgccgggg cagaaggagg cgcacgcaca ggccggcgtg  2460
caggtgaagc aggagcccat tgagagcgat gaggaagagg cagagccccc acgggaggtg  2520
gagccgggcc agcgccagcc cagtgagcag gagctgctct tcagacagca agccctcctg  2580
ctggagcagc agcggatcca ccagctgagg aactaccagg cgtccatgga ggccgccggc  2640
atccccgtgt ccttcggcgg ccacaggcct ctgtcccggg cgcagtcctc acccgcgtct  2700
gccaccttcc ccgtgtctgt gcaggagccc ccaccaagc cgaggttcac gacaggcctc    2760
gtgtatgaca cgctgatgct gaagcaccag tgcacctgcg ggagtagcag cagccacccc  2820
gagcacgccg ggaggatcca gagcatctgg tcccgcctgc aggagacggg cctccggggc  2880
aaatgcgagt gcatccgcgg acgcaaggcc accctggagg agctacagac ggtgcactcg  2940
gaagcccaca ccctcctgta tggcacgaac cccctcaacc ggcagaaact ggacagtaag  3000
aaacttctag gctcgctcgc ctccgtgttc gtccggctcc cttgcggtgg tgttggggtg  3060
gacagtgaca ccatatggaa cgaggtgcac tcggcggggg cagcccgcct ggctgtgggc  3120
tgcgtggtag agctggtctt caaggtggcc acaggggagc tgaagaatgg ctttgctgtg  3180
gtccgccccc ctggacacca tgcggaggag agcacgccca tgggcttttg ctacttcaac  3240
tccgtggccg tggcagccaa gcttctgcag cagaggttga gcgtgagcaa gatcctcatc  3300
gtggactggg acgtgcacca tggaaacggg acccagcagg cttctacag cgaccctagc    3360
gtcctgtaca tgtccctcca ccgctacgac gatgggaact tcttcccagg cagcggggct  3420
cctgatgagg tggcacagg gccggcgtg ggtttcaacg tcaacatggc tttcaccggc    3480
ggcctggacc ccccatggg agacgctgag tacttggcgg ccttcagaac ggtggtcatg  3540
ccgatcgcca gcgagtttgc cccggatgtg gtgctggtgt catcaggctt cgatgccgtg  3600
gagggccacc ccaccccctct tggggctac aacctctccg ccagatgctt cgggtacctg   3660
acgaagcagc tgatgggcct ggctggcggc cggattgtcc tggccctcga gggaggccac  3720
gacctgaccg ccatttgcga cgcctcggaa gcatgtgttt ctgccttgct gggaaacgag  3780
cttgatcctc tcccagaaaa ggttttacag caaagaccca atgcaaacgc tgtccgttcc  3840
atggagaaag tcatggagat ccacagcaag tactggcgct gcctgcagcg cacaacctcc  3900
```

```
acagcggggc gttctctgat cgaggctcag acttgcgaga acgaagaagc cgagacggtc    3960
accgccatgg cctcgctgtc cgtgggcgtg aagcccgccg aaaagagacc agatgaggag    4020
cccatggaag aggagccgcc cctgtagcac tccctcgaag ctgctgttct cttgtctgtc    4080
tgtctctgtc ttgaagctca gccaagaaac tttcccgtgt cacgcctgcg tcccaccgtg    4140
gggctctctt ggagcaccca gggacaccca gcgtgcaaca gccacgggaa gcctttctgc    4200
cgcccaggcc cacaggtctc gagacgcaca tgcacgcctg ggcgtggcag cctcacaggg    4260
aacacgggac agacgccggc gacgcgcaga cacacggaca cgcggaagcc aagcacactc    4320
tggcgggtcc cgcaagggac gccgtggaag aaggagcct gtggcaacag gcggccgagc     4380
tgccgaattc agttgacacg aggcacagaa acaaatatc aaagatctaa taatacaaaa     4440
caaacttgat taaaactggt gcttaaagtt tattacccac aactccacag tctctgtgta    4500
aaccactcga ctcatcttgt agcttatttt tttttaaag aggacgtttt ctacggctgt     4560
ggcccgcctc tgtgaaccat agcggtgtgc ggcgggggt ctgcacccgg gtggggaca     4620
gagggacctt taaagaaaac aaaactggac agaaacagga atgtgagctg ggggagctgg    4680
cttgagtttc tcaaaagcca tcggaagatg cgagtttgtg cctttttttt tattgctctg    4740
gtggattttt gtggctgggt tttctgaagt ctgaggaaca atgccttaag aaaaaacaaa    4800
cagcaggaat cggtgggaca gtttcctgtg gccagccgag cctggcagtg ctggcaccgc    4860
gagctggcct gacgcctcaa gcacgggcac cagccgtcat ctccggggcc aggggctgca    4920
gcccggcggt ccctgttttg ctttattgct gtttaagaaa aatggaggta gttccaaaaa    4980
agtggcaaat cccgttggag gttttgaagt ccaacaaatt ttaaacgaat ccaaagtgtt    5040
ctcacacgtc acatacgatt gagcatctcc atctggtcgt gaagcatgtg gtaggcacac    5100
ttgcagtgtt acgatcggaa tgcttttat aaaagcaag tagcatgaag tattgcttaa      5160
attttaggta taaataaata tatatatgta taatatatat tccaatgtat tccaagctaa    5220
gaaacttact tgattcttat gaaatcttga taaaatattt ataatgcatt tatagaaaaa    5280
gtatatatat atatataaaa tgaatgcaga ttgcgaaggt ccctgcaaat ggatggcttg    5340
tgaatttgct ctcaaggtgc ttatggaaag ggatcctgat tgattgaaat tcatgttttc    5400
tcaagctcca gattggctag atttcagatc gccaacacat tcgccactgg gcaactaccc    5460
tacaagtttg tactttcatt ttaattattt tctaacagaa ccgctcccgt ctccaagcct    5520
tcatgcacat atgtacctaa tgagttttta tagcaaagaa tataaatttg ctgttgattt    5580
ttgtatgaat tttttcacaa aaagatcctg aataagcatt gttttatgaa ttttacattt    5640
ttcctcacca tttagcaatt ttctgaatgg taataatgtc taaatctttt tcctttctga    5700
attcttgctt gtacattttt ttttaccttt caaaggtttt taattatttt tgttttttatt   5760
tttgtacgat gagttttctg cagcgtacag aattgttgct gtcagattct attttcagaa    5820
agtgagagga gggaccgtag gtcttttcgg agtgacacca acgattgtgt ctttcctggt    5880
ctgtcctagg agctgtataa agaagcccag gggctctttt taactttcaa cactagtagt    5940
attacgaggg gtggtgtgtt tttcccctcc gtggcaaggg cagggagggt tgcttaggat    6000
gcccggccac cctgggaggc ttgccagatg ccggggcag tcagcattaa tgaaactcat      6060
gtttaaacttc tctgaccac atcgtcagga tagaattcta acttgagttt tccaaagacc    6120
ttttgagcat gtcagcaatg catggggcac acgtggggct cttacccac ttgggttttt     6180
ccactgcagc cacgtggcca gcctggatt ttggagcctg tggctgcaag gaacccaggg     6240
acccttgttg cctggtgaac ctgcagggag ggtatgattg cctgaccagg acagccagtc    6300
```

-continued

```
tttactcttt ttctcttcaa cagtaactga cagtcacgtt ttactggtaa cttatttccc    6360
agcacatgaa gccaccagtt tcattccaaa gtgtatattg ggttcagact tgggggcaga    6420
agttcagaca caccgtgctc aggagggacc cagagccgag tttcggagtt tggtaaagtt    6480
tacagggtag cttctgaaat taactcaaac ttttgaccaa atgagtgcag attcttggat    6540
tcacttggtc actgggctgc tgatggtcag ctctgagaca gtggtttgag agcaggcaga    6600
acggtcttgg gacttgtttg actttcccct ccctggtggc cactctttgc tctgaagccc    6660
agattggcaa gaggagctgg tccattcccc attcatggca cagagcagtg gcagggccca    6720
gctagcaggc tcttctggcc tccttggcct cattctctgc atagccctct ggggatcctg    6780
ccacctgccc tcttaccccg ccgtggctta tggggaggaa tgcatcatct cacttttttt    6840
ttttaagcag atgatgggat aacatggact gctcagtggc caggttatca gtgggggac    6900 ttaattctaa tctcattcaa atggagacgc cctctgcaaa ggcctggcag ggggaggcac    6960
gtttcatctg tcagctcact ccagcttcac aaatgtgctg agagcattac tgtgtagcct    7020
tttctttgaa gacacactcg gctcttctcc acagcaagcg tccagggcag atggcagagg    7080
atctgcctcg gcgtctgcag gcgggaccac gtcaggagg gttccttcat gtgttctccc    7140
tgtgggtcct tggacccttta gccttttttct tcctttgcaa aggccttggg ggcactggct    7200
gggagtcagc aagcgagcac tttatatccc tttgaggaa accctgatga cgccactggg    7260
cctcttggcg tctgccctgc cctcgcggct tcccgccgtg ccgcagcgtg cccacgtgcc    7320
cacgccccac cagcaggcgg ctgtcccgga ggccgtggcc cgctgggact ggccgccct    7380 ccccagcgtc ccagggctct ggttctggag ggccactttg tcaaggtgtt tcagtttttc    7440
tttacttctt ttgaaaatct gtttgcaagg ggaaggacca tttcgtaatg gtctgacaca    7500
aaagcaagtt tgattttgc agcactagca atggactttg ttgttttct ttttgatcag    7560 aacattcctt ctttactggt cacagccacg tgctcattcc attcttcttt tgtagactt    7620 tgggcccacg tgttttatgg gcattgatac atatataaat atatagatat aaatatatat    7680
gaatatattt tttaagtttt cctacacctg gaggttgcat ggactgtacg accggcatga    7740
ctttatattg tatacagatt ttgcacgcca aactcggcag cttggggaa gaagaaaaat    7800 gcctttctgt tccctctca tgacatttgc agatacaaaa gatggaaatt tttctgtaaa    7860
acaaaacctt gaaggagagg agggcgggga agtttgcgtc ttattgaact tattcttaag    7920
aaattgtact tttattgta agaaaaataa aaaggactac ttaaacattt gtcatattaa    7980 gaaaaaagt ttatctagca cttgtgacat accaataata gagtttattg tatttatgtg    8040
gaaacagtgt tttagggaaa ctactcagaa ttcacagtga actgcctgtc tctctcgagt    8100
tgatttggag gaattttgtt tgttttgtt ttgtttgttt cctttatct ccttccacgg    8160 gccaggcgag cgccgcccgc cctcactggc cttgtgacgg tttattctga ttgagaactg    8220
ggcggactcg aaagagtccc cttttccgca cagctgtgtt gactttttaa ttactttttag    8280 gtgatgtatg gctaagattt cactttaagc agtcgtgaac tgtgcgagca ctgtggttta    8340
caattatact ttgcatcgaa aggaaaccat ttcttcattg taacgaagct gagcgtgttc    8400
ttagctcggc ctcactttgt ctctggcatt gattaaaagt ctgctattga aagaaaaag     8459
```

<210> SEQ ID NO 14
<211> LENGTH: 4077
<212> TYPE: DNA
<213> ORGANISM: Homo sapiens -continued

```
<400> SEQUENCE: 14
gaattcccag ctctctgctc gctctgctcg cagtcacaga cacttgagca cacgcgtaca      60
cccagacatc ttcgggctgc tattggattg actttgaagg ttctgtgtgg gtcgccgtgg     120
ctgcatgttt gaatcaggtg gagaagcact tcaacgctgg acgaagtaaa gattattgtt     180
gttattttt ttttctctct ctctctctct taagaaagga aaatatccca aggactaatc      240
tgatcgggtc ttccttcatc aggaacgaat gcaggaattt gggaactgag ctgtgcaagt     300
gctgaagaag gagatttgtt tggaggaaac aggaaagaga aagaaaagga aggaaaaaat     360
acataatttc agggacgaga gagagaagaa aaacggggac tatggggaga aaaaagattc     420
agattacgag gattatggat gaacgtaaca gacaggtgac atttacaaag aggaaatttg     480
ggttgatgaa gaaggcttat gagctgagcg tgctgtgtga ctgtgagatt gcgctgatca     540
tcttcaacag caccaacaag ctgttccagt atgccagcac cgacatggac aaagtgcttc     600
tcaagtacac ggagtacaac gagccgcatg agagccggac aaactcagac atcgtggaga     660
cgttgagaaa gaagggcctt aatggctgtg acagcccaga ccccgatgcg gacgattccg     720
taggtcacag ccctgagtct gaggacaagt acaggaaaat taacgaagat attgatctaa     780
tgatcagcag gcaaagattg tgtgctgttc cacctcccaa cttcgagatg ccagtctcca     840
tcccagtgtc cagccacaac agtttggtgt acagcaaccc tgtcagctca ctgggaaacc     900
ccaacctatt gccactggct cacccttctc tgcagaggaa tagtatgtct cctggtgtaa     960
cacatcgacc tccaagtgca ggtaacacag gtggtctgat gggtggagac ctcacgtctg    1020
gtgcaggcac cagtgcaggg aacgggtatg gcaatccccg aaactcacca ggtctgctgg    1080
tctcacctgg taacttgaac aagaatatgc aagcaaaatc tcctccccca atgaatttag    1140
gaatgaataa ccgtaaacca gatctccgag ttcttattcc accaggcagc aagaatacga    1200
tgccatcagt gtctgaggat gtcgacctgc ttttgaatca aaggataaat aactcccagt    1260
cggctcagtc attggctacc ccagtggttt ccgtagcaac tcctacttta ccaggacaag    1320
gaatgggagg atatccatca gccatttcaa caacatatgg taccgagtac tctctgagta    1380
gtgcagacct gtcatctctg tctgggttta acaccgccag cgctcttcac cttggttcag    1440
taactggctg gcaacagcaa cacctacata acatgccacc atctgccctc agtcagttgg    1500
gagcttgcac tagcactcat ttatctcaga gttcaaatct ctccctgcct tctactcaaa    1560
gcctcaacat caagtcagaa cctgtttctc ctcctagaga ccgtaccacc ccccttcga     1620
gatacccaca acacacgcgc cacgaggcgg ggagatctcc tgttgacagc ttgagcagct    1680
gtagcagttc gtacgacggg agcgaccgag aggatcaccg gaacgaattc cactccccca    1740
ttggactcac cagaccttcg ccggacgaaa gggaaagtcc ctcagtcaag cgcatgcgac    1800
tttctgaagg atgggcaaca tgatcagatt attacttact agttttttt tttttcttgc     1860
agtgtgtgtg tgtgctatac cttaatgggg aagggggtc gatatgcatt atatgtgccg     1920
tgtgtggaaa aaaaaaagt caggtactct gttttgtaaa agtacttta aattgcctca      1980
gtgatacagt ataagataa acagaaatgc tgagataagc ttagcacttg agttgtacaa     2040
cagaacactt gtacaaaata gattttaagg ctaacttctt ttcactgttg tgctcctttg    2100
caaaatgtat gttacaatag atagtgtcat gttgcaggtt caacgttatt tacatgtaaa    2160
tagacaaaag gaaacatttg ccaaaagcgg cagatcttta ctgaaagaga gagcagctgt    2220
tatgcaacat atagaaaaat gtatagatgc ttggacagac ccggtaatgg gtggccattg    2280
gtaaatgtta ggaacacacc aggtcacctg acatcccaag aatgctcaca aacctgcagg    2340
```

-continued

```
catatcattg gcgtatggca ctcattaaaa aggatcagag accattaaaa gaggaccata    2400
cctattaaaa aaaaatgtgg agttggaggg ctaacatatt taattaaata aataaataaa    2460
tctgggtctg catctcttat taaataaaaa tataaaaata tgtacattac attttgctta    2520
ttttcatata aaaggtaaga cagagtttgc aaagcatttg tggcttttg tagtttactt    2580 aagccaaaat gtgttttttt ccccttgata gcttcgctaa tattttaaac agtcctgtaa    2640
aaaaccaaaa aggactttt gtatagaaag cactaccta agccatgaag aactccatgc    2700
tttgctaacc aagataactg ttttctcttt gtagaagttt tgtttttgaa atgtgtattt    2760
ctaattatat aaaatattaa gaatctttta aaaaaatctg tgaaattaac atgcttgtgt    2820
atagctttct aatatatata atattatggt aatagcagaa gttttgttat cttaatagcg    2880
ggaggggggt atatttgtgc agttgcacat ttgagtaact attttctttc tgttttcttt    2940
tactctgctt acatttata agtttaaggt cagctgtcaa aaggataacc tgtggggtta    3000
gaacatatca cattgcaaca ccctaaattg tttttaatac attagcaatc tattgggtca    3060
actgacatcc attgtatata ctagtttctt tcatgctatt tttattttgt ttttgcatt    3120 tttatcaaat gcagggcccc tttctgatct caccatttca ccatgcatct tggaattcag    3180
taagtgcata tcctaacttg cccatattct aaatcatctg gttggtttc agcctagaat    3240 ttgatacgct ttttagaaat atgcccagaa tagaaaagct atgttgggc acatgtcctg    3300 caaatatggc cctagaaaca agtgatatgg aatttacttg gtgaataagt tataaattcc    3360
cacagaagaa aaatgtgaaa gactgggtgc tagacaagaa ggaagcaggt aaagggatag    3420
ttgctttgtc atccgttttt aattatttta actgaccctt gacaatcttg tcagcaatat    3480
aggactgttg aacaatcccg gtgtgtcagg accccaaat gtcacttctg cataaagcat    3540
gtatgtcatc tatttttct tcaataaaga gatttaatag ccatttcaag aaatcccata    3600
aagaacctct ctatgtccct ttttttaatt taaaaaaatg actcttgtct aatattcgtc    3660
tataagggat taattttcag acccttaat aagtgagtgc cataagaaag tcaatatata    3720
ttgtttaaaa gatatttcag tctaggaaag attttccttc tcttggaatg tgaagatctg    3780
tcgattcatc tccaatcata tgcattgaca tacacagcaa agaagatata ggcagtaata    3840
tcaacactgc tatatcatgt gtaggacatt tcttatccat ttttctctt ttacttgcat    3900 agttgctatg tgtttctcat tgtaaaaggc tgccgctggg tggcagaagc caagagacct    3960
tattaactag gctatatttt tcttaacttg atctgaaatc cacaattaga ccacaatgca    4020
cctttggttg tatccataaa ggatgctagc ctgccttgta ctaatgtttt atatatt      4077
```

METHODS OF USING DEACETYLASE INHIBITORS TO PROMOTE CELL DIFFERENTIATION AND REGENERATION

CROSS REFERENCE TO RELATED APPLICATIONS

This is a continuation of U.S. patent application Ser. No. 10/492,901 filed Apr. 15, 2004, issued as U.S. Pat. No. 7,229,963, which is a U.S. National Stage of International Application No. PCT/US02/33570 filed Oct. 17, 2002, which was published under PCT Article 21(2), and which claims the benefit of U.S. Provisional Application Nos. 60/335,705 filed Oct. 18, 2001 and 60/343,854 filed Oct. 25, 2001, each of which applications is incorporated herein in its entirety.

FIELD

This disclosure relates to progenitor cell differentiation, growth and regeneration. Methods are disclosed for promoting progenitor cell differentiation and investigating and/or treating physiological diseases and disorders, such as diseases and disorders of the circulatory system, the musculoskeletal system, and the nervous system. Methods are also disclosed for promoting the growth and development of vertebrate embryos.

BACKGROUND

Progenitor cells are undifferentiated, non-specialized cells that give rise to particular cell lineages. For example, muscle progenitor cells (myoblasts) give rise to muscle cells, neuronal progenitor cells (neuroblasts) differentiate to produce nerve cells, and hematopoetic progenitor cells are the precursors of cells found in blood and lymph. Understanding the molecular controls of cellular differentiation from progenitor cells to mature cells has important implications in research about, and therapy for, many different diseases associated with tissue degeneration and/or atrophy, including muscular dystrophy, Alzheimer's disease, and anemia.

For example, myoblasts differentiate into multinucleated myotubes, which develop into mature muscle fibers (myocytes). This differentiation occurs naturally in vertebrate mammals, but also may be accomplished artificially. During transition from myoblasts to myotubes, two muscle-restricted proteins, MyoD and Myf5 (which are functionally inert in myoblasts) trigger a cascade of cellular events leading to the irreversible cell cycle arrest, the expression of other myogenic regulatory factors (MRFs), and the transcription of a number of differentiation-specific genes encoding structural and contractile proteins. See, e.g., Lassar, A. and A. Münsterberg, Current Opinion in Cell Biology 6:432-42 (1994); Molkentin, J. D. and E. N. Olson, Current Opinion in Genetics & Development 6:445-53 (1996).

SUMMARY

Disclosed is a method of enhancing progenitor cell differentiation, including enhancing myogenesis, neurogenesis, and hematopoiesis, by contacting an undifferentiated progenitor cell with an effective amount of a deacetylase inhibitor (DI), resulting in enhancement of progenitor cell differentiation. This effect is surprising because it has previously been shown that deacetylase inhibitors inhibit cellular differentiation of differentiated cells.

In some embodiments, the progenitor cell is part of a cell culture, such as a cell culture used for in vitro or in vivo analysis of progenitor cell differentiation, while in other embodiments, the cell is part of an organism, such as a human or other mammal.

Any suitable DI can used, including (but not limited to) sodium butyrate, trichostatin A, or valproic acid.

In some embodiments, progenitor cell differentiation is enhanced by enhancing expression of differentiation-related genes in a progenitor cell. In particular embodiments, the progenitor cell is a myoblast, neuroblast, or hematopoietic progenitor cell, and the agent enhances expression of muscle-specific genes, nerve-specific genes, or hematopoietic-specific genes. Expression of differentiation-related genes can be accomplished by inhibiting the formation of complexes between a deacetylase and a transcription factor, such as a transcription factor with a basic helix-loop-helix (bHLH) configuration.

Enhancing expression of differentiation-related genes also can be accomplished in subjects deficient in myogenesis, neurogenesis, or hematopoiesis. In some embodiments, the deficiency leads to a loss of muscle tissue, nerve tissue, or hematopoietic tissue. However, a subject not deficient in myogenesis, neurogenesis, or hematopoiesis can still suffer a disease or condition associated with a loss of muscle tissue, nerve tissue, or hematopoietic tissue.

In one embodiment, inhibiting a deacetylase is part of a method of treating a disease or condition associated with degeneration of muscle tissue, nerve tissue, or hematopoietic tissue. Thus, a subject suffering such a disease or condition is identified, and a therapeutically effective amount of a deacetylase inhibitor is administered to the subject.

BRIEF DESCRIPTION OF THE DRAWINGS

FIGS. 1A-F illustrate exposure of skeletal muscle cells to the deacetylase inhibitors sodium butyrate, TSA, or VPA. These figures show that DI exposure modulates cell differentiation and the levels of endogenous muscle proteins depending on the timing of treatment. FIG. 1A is a Western blot of C2C12 cells cultured in differentiation medium (DM) were either non-treated (−) or treated with sodium butyrate (B) for 48 hours. Cellular extracts were obtained and analyzed by Western blotting for the presence of MHC, tubulin, and myogenin. FIG. 1B shows C2C12 cells treated as described in FIG. 1A with MFC detected by immunofluorescence. Nuclei were stained with DAPI. FIG. 1C illustrates MHC levels of C2C12 cells determined with the MF-20 antibody and tubulin, visualized with the E7 antibody. Cells were cultured in growth medium (GM) and exposed to either sodium butyrate (B), TSA (T), or VPA (V) for 24 hours and then switched to DM for additional 48 hours in the absence of TSA. Additionally, RT-PCR was performed on RNA obtained form cells treated with TSA (T) or without (−) TSA with specific primers for either MCK or GAPDH. FIG. 1D shows C2C12 cells treated as described in FIG. 1C with MHC detected by immunofluorescence. Nuclei were stained with DAPI. FIG. 1E shows MHC levels of human skeletal myocytes (HSkM) detected by immunofluorescence. Cells were grown in GM and treated with TSA for 24 hours, then switched to DM in the absence of TSA for additional 48 hours. Nuclei were stained with DAPI. Additionally, a Western blot analysis of MHC and tubulin expression in either untreated or TSA-treated (T) HSkM is shown. FIG. 1F shows MHC detected by immunofluorescence in HSkM either untreated (Control) or exposed to TSA. Nuclei were stained with DAPI.

FIG. 2A shows the activation of MCK-luc and CMV-luc monitored after transient transfection in C2C12 cells. Luciferase activity was measured in non-treated cells cultured in either GM (GM) or DM (DM). Alternatively, C2C12 were exposed to sodium butyrate for 24 hours in GM and then switched to DM without sodium butyrate (Butyr/GM>DM) or treated with sodium butyrate when cultured in DM (Butyr/DM) before being analyzed for luciferase activity. FIG. 2B shows C2C12 cells transfected with MCK-luc either in the absence or presence of an HDAC1-expression vector and exposed to sodium butyrate when cultured in GM. Luciferase assays were performed after culturing the cells for 48 hours in DM without sodium butyrate. FIG. 2C shows the transcriptional activity of an E2F-responsive construct evaluated either in the absence or presence of sodium butyrate in GM and DM conditions as described in FIG. 2A. FIG. 2D shows the activity of three integrated reporters (4RE-luc, MCK-luc and cyclA-luc) in C2C12 cell clones monitored after exposure (+) or not (−) to TSA for 48 hours in GM. The reporter activity was also analyzed in cells differentiated in the absence of TSA (DM)

FIGS. 3A-C show that exposure of undifferentiated myoblasts to DI results in MyoD and histone hyperacetylation. In FIG. 3A, MyoD acetylation in undifferentiated C2C12 myoblasts (GM) untreated (−) or treated with either sodium butyrate (Butyr.) or TSA and in differentiated myotubes (abbrev. DM in FIG. 3A, but not to be confused with the abbreviation for "differentiation medium" as used elsewhere herein) was measured by $^3$H incorporation of exogenously transfected Flag-tagged MyoD following metabolic labeling with $^3$H sodium acetate as described in Sartorelli, V., et al., *Molecular Cell* 4:725-34 (1999). FIG. 3B shows C2C12 myoblasts (grown in GM) and myotubes (grown in DM for 48 hours) and formaldehyde cross-linked. Chromatin was immunoprecipitated with antibodies against acetyl-histone 4 (AcH4) or IgG (as a control). Purified DNA from anti-AcH4 immunoprecipitated chromatin was analyzed by PCR using primers recognizing GAPDH promoter and MCK enhancer as described in Example 1. Unbound DNA (lanes 2 and 3, top panel) is an aliquot of chromatin not immunoprecipitated by anti-AcH4 antibody and amplified with GAPDH primers. Input (lanes 2 and 3, bottom panel) is an aliquot (1%) of the chromatin analyzed before the immunoprecipitation to quantify the amount of DNA present in different samples. FIG. 3C shows the results of a ChIP (described in Example 1) for myoblasts cultured in GM and exposed (+) or not (−) to TSA for 16 hours and cultured in the absence of TSA in DM for 24 hours. Myoblasts were then formaldehyde cross-linked and processed.

FIG. 4A shows C2C12 cells transfected with the MLC1/3F-nLacZ plasmid reporter construct. Cells were then exposed to TSA (50 nM) in GM and subsequently switched to DM for 48 hours. Cells were stained to detect β-galactosidase activity. FIG. 4B is a picture of E 10.5 embryos derived from MLC1/3F-nLacZ transgenic mice exposed to either TSA or VPA treatment (see Example 1) and stained for 1 hour at 30° C. to detect β-galactosidase activity. TSA-treated and VPA-treated embryos showed a higher level of MLC-lacZ transgene expression and a larger number of somites expressing MLC1/3F-nLacZ than control embryos. FIG. 4C is a Western blot of extracts derived from total embryos exposed to either TSA or VPA; MHC is detected.

FIGS. 5A-D illustrate downregulation of deacetylases during skeletal myogenesis and formation of distinct complexes with MyoD in myoblasts and pRb in Myotubes. FIG. 5A is a Western blot of the levels of MyoD, MHC, cyclin A, pRb, and tubulin detected using total extracts from C2C12 cells. The activity of MCK (graph beneath Western blot) was monitored in C2C12 cell extracts at the same time points (18 and 36 hours) and is calculated as micromoles of creatine formed/min/mg of protein extract. FIG. 5B shows immunoprecipitation of endogenous HDAC1 (upper panel, IP HDAC1) or pRb (middle panel, IP pRb) from extracts of C2C12 cells grown either in GM (20% FBS) or DM (2% horse serum) for 36 hr, using a mixture of anti-HDAC1 antibodies or anti-pRb. The coimmunoprecipitated proteins were revealed by Western blot. In the lower panel (SN IP pRb), the presence of HDAC1 and MyoD in the extracts before or after pRb immunoprecipitation was evaluated by Western blot. The amount of HDAC1 remaining in the supernatant of DM after immunoprecipitation with Rb was calculated to be 30% of that present in whole DM extract by densitometric scanning of the Western blot. Total cell lysate from C2C12 was used to verify the identity of immunoprecipitated proteins. FIG. 5C shows immunoprecipitation of endogenous HDAC1 from extracts of C2C12 cells grown either in GM (20% FBS) or DM (2% horse serum), with the coimmunoprecipitated MyoD detected by Western blot. FIG. 5D illustrates a deacetylation assay performed following immunoprecipitation of MyoD or pRb from nuclear extracts of either C2C12 undifferentiated (GM) or differentiated (DM for 36 hr) cells, treated (+) or not (blank) with TSA, and subsequent incubation with preacetylated histones. The values of deacetylase activity were normalized by the amount of immunoprecipitated proteins (lower panels).

FIG. 6A illustrates the interaction of FLAG-tagged HDAC1 and pRb proteins, mixed in different combinations, determined by immunoprecipitation with anti-HDAC1. The precipitated proteins were detected by immunoblotting with the M2 anti-FLAG antibody. Input proteins are 10% of that employed in immunoprecipitation. FIG. 6B illustrates the reaction of FLAG-tagged HDAC1 incubated with His-MyoD in different combinations; the reaction was immunoprecipitated with anti-HDAC1, and MyoD was revealed in immunoblotting with anti-MyoD antibody. FIG. 6C shows the results of competition experiments performed by incubating FLAG-HDAC1 and FLAG-pRb either in the absence (−) or presence (+) of increasing concentrations of His-MyoD. Immunoprecipitation was conducted with anti-HDAC1 antibodies and the precipitated proteins revealed with M2 anti-FLAG and anti-MyoD antibodies. Right panel: the amount of pRb bound to HDAC1 either in the absence or presence of His-MyoD was quantitated using the NIH Image 1.6 software program. FIG. 6D is a Western blot illustrating the levels of HDAC1, 2, 4, and 5 detected using total extracts from C2C12 cells. FIG. 6E shows the levels of HDAC1 and HDAC2 transcripts in undifferentiated C2C12 myoblasts, either proliferating or confluent (lanes 1 and 2, GM), and at different time points of differentiation (lanes 3, 4, and 5, DM) were determined by Northern blot. As a control, myogenin and cyclin DI RNA levels were also measured.

FIG. 7 illustrates the effect of HDAC1/2 overexpression on MyoD-dependent transcription and muscle-specific gene expression. C2C12 cells were transfected in GM with a vector encoding GFP alone or in conjunction with HDAC1 and then induced to differentiate in DM for 36 hours. After fixation in paraformaldehyde, productively transfected cells were visualized by the expression of cotransfected GFP. Myogenic differentiation was scored by determining expression of MHC (red) in GFP-positive cells.

FIG. 8A shows MyoD coexpression with HDAC1, or the enzymatic defective mutant HDAC1-D174N-D176N, and the 4RE-luc reporter in 10T1/2 cells. The bottom panel shows 50 μg of total cell extracts analyzed by Western blot for the presence of transfected MyoD and HDAC1. In FIG. 8B, MEF2C was coexpressed in 10T1/2 cells with either HDAC1 or HDAC1-D174N-D176N and a MEF2-responsive reporter. In FIG. 8C, MyoD was coexpressed in 10T1/2 cells with the 4RE-luc reporter and increasing amounts of HDAC1. In FIG. 8D, MyoD was coexpressed in 10T1/2 cells with HDAC1 and 4RE-luc in the presence or absence of TSA (50 nM). The bottom panel shows 50 μg of total cell extracts analyzed by Western blot for the presence of transfected HDAC1 (bottom panel). FIG. 8E shows the chimeric protein MyoD-E47 coexpressed in 10T1/2 cells with increasing doses of HDAC1 and 4RE-luc. FIG. 8F shows Gal-MyoD was coexpression in 10T1/2 cells with increasing doses of HDAC1. FIG. 8G shows MyoD and MEF2C expressed in 10T1/2 cells alone or in combination with E12 and the MCK-luc reporter. HDAC1, or the enzymatic defective mutant HDAC1-D174N-D176N, and HDAC4, or its enzymatic defective mutant HDAC4-D640N, were coexpressed. The bottom panel shows 50 μg of total cell extracts analyzed by Western blot for the presence of transfected MyoD, MEF2, HDAC1, and HDAC4 (right panel).

FIG. 9A shows immunoprecipitation of HDAC1 from pRb–/–p53±double knock out derived 3T3 fibroblasts converted by retroviral-mediated expression of MyoD. The association with MyoD was monitored at different stages of myogenic conversion (GM and DM for 36 hours) by Western blot using anti-MyoD antibodies. In FIG. 9B, pRb–/–p53±double knock out derived 3T3 cells were transfected with Flag-HDAC1 and myc-MyoD. Nuclear extracts were prepared and subsequently incubated with increasing amounts of either GST-pRbwt or GST-pRbN757F. The amount of GST-recruited HDAC1 was revealed by Western blot using anti-Flag antibodies. The HDAC1 present in the supernatant of the GST pull-down was immunoprecipitated with anti-Flag conjugated beads, and the associated MyoD was detected by Western blot by using anti-myc antibodies. In FIG. 9C (upper panel), a graph illustrates the ability to activate MCK-luc reporter by MyoD transiently expressed in pRb–/–p53±3T3 fibroblasts, evaluated with or without the co-expression of pRb wt or pRb N757F. In the lower panel of FIG. 1C, levels of endogenous MHC, p21, myogenin, tubulin, and ectopically produced pRb were evaluated by Western blot in pRb–/–p53±3T3 fibroblasts after transient expression of MyoD alone or in conjunction with either pRb wt or pRb N757F. FIG. 9D is a graph illustrating the ability to activate the MCK-luc reporter by MyoD and MEF2C alone, or in combination with E12, in pRb–/–p53±double knock out derived 3T3 cells was evaluated with or without the co-expression of pRb wt or pRb N757F. FIG. 9D is a graph showing transcriptional activation of pRb–/–cells transfected with MCK-luc and different combinations of MyoD, E2F1-pRb (SP), HDAC1 WT and HDAC1 ΔIACEE (MT) expression vectors. Transcriptional activation was measured by luciferase assay.

FIG. 10A is a graph illustrating the effect of reconstituting MD3 cells, growing in GM and transfected with 4RE-luc, with different pRb mutants either alone or in conjunction with the cdks inhibitors p21 and p16. FIG. 10B shows MD3 cells growing in GM transiently transfected with HDAC1 alone (lane 1) or in conjunction with different pRb mutants (lanes 2 to 5). Forty-eight hours after transfection, cells were harvested and the total lysate was incubated with anti-MyoD antibodies to immunoprecipitate the endogenous MyoD. Co-immunoprecipitation with HDAC1 (both endogenous and exogenously transfected) was revealed by Western blot using anti-HDAC1 antibody. 1/10 of the total lysate before the immunoprecipitation was used to monitor the expression levels of MyoD, HDAC1 and the phosphorylation status of pRb. FIG. 10C is a model illustrating the regulation of muscle-specific transcription by class I histone deacetylases, class II histone deacetylases, acetyltransferases, and pRb.

BRIEF DESCRIPTION OF THE SEQUENCE LISTING

Figure 1B:
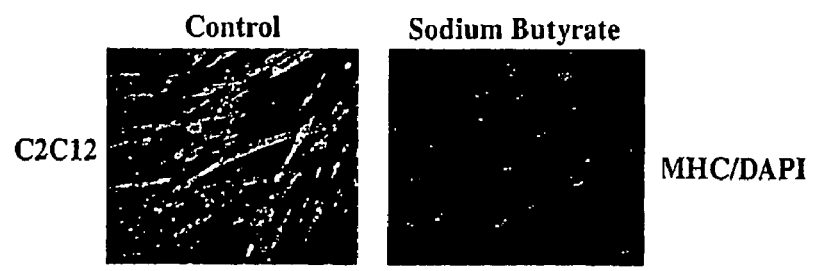

The nucleic acid sequences listed herein are shown using standard letter abbreviations for nucleotide bases. Only one strand of each nucleic acid sequence is shown, but the complementary strand is understood as included by any reference to the displayed strand.

SEQ ID NOS: 1 and 2 show the GAPDH primer pair used in a PCR amplification.

SEQ ID NOS: 3 and 4 show the MCK primer pair used in a PCR amplification.

SEQ ID NO: 5 is the nucleic acid sequence encoding mouse MHC corresponding to GenBank Accession No. M9_2099.

SEQ ID NO: 6 is the nucleic acid sequence encoding mouse myogenin corresponding to GenBank Accession No. NM_031189.

SEQ ID NO: 7 is the nucleic acid sequence encoding mouse MyoD corresponding to GenBank Accession No. XM_124916.

SEQ ID NO: 8 is the nucleic acid sequence encoding mouse MCK corresponding to GenBank Accession No. M21390.

SEQ ID NO: 9 is the nucleic acid sequence encoding mouse GAPDH corresponding to GenBank Accession No. NM_008084.

SEQ ID NO: 10 is the nucleic acid sequence encoding human MLC1/3F corresponding to GenBank Accession No. NM_079422.

SEQ ID NO: 11 is the amino acid sequence for mouse Rb corresponding to GenBank Accession No. A33_718.

SEQ ID NO: 12 is the nucleic acid sequence encoding human HDAC1 corresponding to GenBank Accession No. NM_004964.

SEQ ID NO: 13 is the nucleic acid sequence encoding human HDAC4 corresponding to GenBank Accession No. NM_006037.

SEQ ID NO: 14 is the nucleic acid sequence encoding human MEF2C corresponding to GenBank Accession No. NM_002397.

DETAILED DESCRIPTION

Surprisingly, deacetylase inhibitors (DIs) have been found to promote the differentiation, growth, and regeneration of undifferentiated progenitor cells, if the undifferentiated progenitor cells are contacted with a DI during a stage of development, such as during the myoblast stage. While protein acetylation promotes muscle transcription and differentiation, it has been known for some time that deacetylase inhibitors can repress muscle-gene transcription and cellular differentiation in differentiated myotubes. See, e.g., Blau, H. M. and C. J. Epstein, Cell 17:95-108 (1979); Fiszmnan, M. Y., et al., Exp Cell Res 126: 31-7 (1980); Johnston, L. A., et al., Molecular & Cellular Biology 12:5123-30 (1992). For example, the deacetylase inhibitor (DI), sodium butyrate, has been shown to inhibit differentiation skeletal muscle cells (myocytes) by affecting certain molecular cellular mechanisms. However, in contrast, DIs promote muscle-gene transcription and cellular differentiation in undifferentiated myoblasts.

Abbreviations
  bHLH=basic helix-loop-helix.
  DI=deacetylase inhibitor.
  DM=differentiation medium.
  GAPDH=glyceraldehyde-3-phosphate dehydrogenase:
  GM=growth medium.
  HDAC=class I histone deacetylase.
  HSkM=human skelatalmyocyte.
  MCK=muscle creatine kinase.
  MHC=myosin heavy chain.
  MRF=mycogenic regulator factor.
  Rb=retinoblastoma protein.
  pRb=phosphorylated Rb.
  TSA=trichostatin A.
  VPA=valproic acid.

Explanation of Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995.

As used herein, the singular forms "a," "an," and "the," refer to both the singular as well as plural, unless the context clearly indicates otherwise. For example, the term "a cell" includes single or plural cells and can be considered equivalent to the phrase "at least one cell."

As used herein, the term "comprises" means "includes." Thus, "comprising a deacetylase inhibitor" means "including a deactylase inhibitor," without excluding additional elements.

The term "or" refers to a single element of stated alternative elements or a combination of two or more elements. For example, the phrase "a muscle progenitor cell or a neuronal progenitor cell" refers to a muscle progenitor cell, a neuronal progenitor cell, or both a muscle progenitor cell and a neuronal progenitor cell.

As used herein, a group of members stated in the alternative includes embodiments relating to a single member of the group or combinations of multiple members. For example, the term "muscle tissue, nerve tissue, or hematopoietic tissue," includes embodiments relating to "muscle tissue," "nerve tissue," "hematopoietic tissue," "muscle tissue and nerve tissue," "muscle tissue and hematopoietic tissue," "nerve tissue and hematopoietic tissue," and "muscle tissue, nerve tissue, and hematopoietic tissue."

In order to facilitate review of the various embodiments of the invention, the following explanations of terms are provided:

Amplification: of a nucleic acid molecule (e.g., a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques.

The PCR method can be modified in certain embodiments. For example, reverse-transcription PCR (RT-PCR) can be used to amplify RNA molecules, and a polymerase chain reaction-enzyme immunoassay (PCR-EIA) method can be used for amplification and differentiation of nucleotides. See, e.g., Elie, C. M., et al., J. Clin. Microbiol. 36:3260-65 (1998); and Fujita, S., et al., J. Clin. Microbiol. 33:962-67 (1995).

Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320,308; gap filling ligase chain reaction amplification, as disclosed in U.S. Pat. No. 5,427,930; and NASBA™ RNA transcription-free amplification, as disclosed in U.S. Pat. No. 6,025,134.

Animal: A living multi-cellular vertebrate or invertebrate organism, a category that includes, for example, mammals and birds. The term mammal includes both human and non-human mammals. Similarly, the term "subject" includes both human and veterinary subjects.

Antisense, Sense, and Antigene: A DI can be based on an antisense molecule directed to inhibiting translation of a deacetylase gene.

Double-stranded DNA (dsDNA) has two strands, a 5' to 3' strand, referred to as the plus (+) strand, and a 3' to 5' strand (the reverse complement), referred to as the minus (−) strand. Because RNA polymerase adds nucleic acids in a 5' to 3' direction, the minus strand of the DNA serves as the template for the RNA during transcription. Thus, the RNA formed will have a sequence complementary to the minus strand and identical to the plus strand (except that U is substituted for T). Complementary binding occurs when the base of one molecule forms a hydrogen bond with another molecule. Normally the base adenine (A) is complementary to thymidine (T) and uracil (U), while cytosine (C) is complementary to guanine (G).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a particular dsDNA target.

A gene-suppressive technology that is similar to antisense technology involves the use of small inhibitory RNA molecules (siRNAs) to inhibit a target gene. These siRNAs also are known as short interfering RNA molecules. Methods of using siRNAs to inhibit eukaryotic gene expression, and more particularly, mammalian gene expression, are in the literature, for instance, Gitlin, et al., Nature 418:430-34 (2002); Caplen et al., Proc. Natl. Acad. Sci. 98(17):9742-9747 (2001); Gitlin, et al., Nature 418:430-34 (2002); and Elbashir et al., Nature 411:494-498, 2001.

To inhibit translation of a target deacetylase RNA molecule, and antisense molecule should persist in the cell for a sufficient period of time to contact the target RNA. However, the cell contains enzymes and other components that cause polynucleotides (such as the antisense molecule) to degrade. Therefore, an antisense molecule can be genetically engineered to avoid such degradation in the cell, for example, by substituting the normally occurring phosphodiester linkage, which connects the individual bases of the antisense molecule, with modified linkages. These modified linkages can, for example, be a phosphorothioate, methylphosphonate, phosphodithioate, or phosphoselenate. Furthermore, a single antisense molecule can contain multiple substitutions in various combinations.

The antisense molecule also can be designed to contain different sugar molecules. For example the molecule can contain the sugars ribose, deoxyribose or mixtures thereof, which are linked to a base. The bases give rise to the antisense molecule's ability to bind complementarity to the target RNA. However, in order to be effective, the antisense molecule does not have to be 100% complementary to the target RNA.

Catalytic antisense molecules also contain regions that complement the target RNA sequence. These regions serve to allow the antisense molecules to specifically bind to the target RNA of interest. The catalytic molecules also contain regions that are not complementary to the target RNA. These non-complementary regions typically will contain a sequence which gives the molecule its catalytic activity. Additionally, the catalytic molecules are subject to the same potential problem of degradation as the antisense molecules. Therefore, the catalytic molecules can be designed to contain the same substitutions already discussed.

The antisense polynucleotides, which include both antisense molecules and catalytic nucleic acid molecules, can vary in length. Generally, a longer complementary region will give rise to a molecule with higher specificity. However, these longer molecules can be more difficult to synthesize. Therefore, the longer polynucleotide molecules can be used in conjunction with systems which produce the therapeutic molecules in vivo. These systems involve cloning the polynucleotide sequence into a vector and then delivering the vector to a host cell. The host cell then supplies the necessary components for transcription of the therapeutic molecule.

Shorter polynucleotides (oligonucleotides) can conveniently be produced synthetically, as well as being produced in vivo. These antisense oligonucleotides are of at least six nucleotides, and in particular embodiments, are oligonucleotides ranging from about six to about 50 oligonucleotides. However, in other embodiments, the oligonucleotide is at least 10 nucleotides, at least 15 nucleotides, at least 25 nucleotides, at least 30 nucleotides, at least 50 nucleotides, or at least 75 nucleotides. The oligonucleotides can be DNA or RNA, or chimeric mixtures or derivatives or modified versions thereof, single-stranded or double-stranded. The oligonucleotide can be modified at the base moiety, sugar moiety, or phosphate backbone, and can include other appending groups such as peptides, or agents facilitating transport across the cell membrane (see, e.g., Letsinger et al., PNAS USA 86:6553-6556, 1989; Lemaitre et al., PNAS USA 84:648-652, 1987; PCT Publication No. WO 88/09810) or blood-brain barrier (see, e.g., PCT Publication No. WO 89/10134), hybridization triggered cleavage agents (see, e.g., Krol et al., BioTechniques 6:958-976, 1988) or intercalating agents (see, e.g., Zon, Pharm. Res. 5:539-549, 1988).

In one exemplary embodiment, a single-stranded antisense nucleic acid directed to the HDAC1 mRNA is provided. In a more particular aspect, such a nucleic acid comprises a sequence antisense to the sequence encoding the catalytic domain of the HDAC1 protein.

The oligonucleotide can be modified at any position on its structure with substituents. For example, a modified base moiety can be 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, or 2,6-diaminopurine.

In another exemplary embodiment, the antisense oligonucleotide includes a modified sugar moiety such as arabinose, 2-fluoroarabinose, xylose, or hexose.

In another exemplary embodiment, the antisense oligonucleotide includes a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

As an alternative to antisense inhibitors, catalytic nucleic acid compounds, such as ribozymes or anti-sense conjugates, can be used to inhibit expression of a deacetylase gene, such as HDAC1. Ribozymes can be synthesized and administered to the subject, or can be encoded on an expression vector, from which the ribozyme is synthesized in the targeted cell (as in PCT publication WO 9523225, and Beigelman et al. Nucl. Acids Res. 23:4434-4442, 1995). Examples of oligonucleotides with catalytic activity are described in WO 9506764, WO 9011364, and Sarver et al., Science 247:1222-1225, 1990. Conjugates of antisense with a metal complex, e.g. terpyridylCu (II), capable of mediating mRNA hydrolysis, are described in Bashkin et al., Appl. Biochem Biotechnol. 54:43-56, 1995.

Particular antisense nucleic acids of the invention include a sequence complementary to at least a portion of an RNA transcript of an HDAC1 gene, including a human HDAC1 gene. However, absolute complementarity is not required.

An antisense sequence can be complementary to at least a portion of a deacetylase RNA, meaning a sequence having sufficient complementarity to be able to hybridize with the target deacetylase RNA, forming a stable duplex; in the case of double-stranded antisense nucleic acids, a single strand of the duplex DNA thus can be tested, or triplex formation can be assayed. The ability to hybridize will depend on both the degree of complementarity and the length of the antisense nucleic acid. Generally, the longer the hybridizing nucleic acid, the more base mismatches with a target RNA it can contain and still form a stable duplex (or triplex, as the case may be).

The amount of an antisense nucleic acid effective for inhibiting a particular deacetylase can depend on the nature of the deacetylase, or the intended prophylactic or therapeutic effect, which can be determined by standard clinical techniques. In one, non-limiting example, pharmaceutical compositions comprising antisense nucleic acids targeting HDAC1 are administered via liposomes, microparticles, or microcapsules. It can be useful to use such pharmaceutical compositions to achieve sustained release of the antisense nucleic acid, for example, by utilizing liposomes targeted via antibodies to specific identifiable cellular antigens.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA is synthesized in the laboratory by reverse transcription from messenger RNA extracted from cells.

Deacetylase: An enzyme that mediates the removal or modification of acetyl groups to a variety of substances in intermediary metabolism. Exemplary deacetylases include (but are not limited to): acetaminophen deacetylase, acetylgalactosamine deacetylase, acetylpolyamine deacetylase, acetylspermidine deacetylase, C-10-deacetylase, citrate (pro-3S)-lyase deacetylase, heparan sulfate-N-deacetylase-N-sulfotransferase, histone deacetylase, melatonin deacetylase, N-acetylornithine deacetylase, N-acetylphosphinothricin deacetylase, poly(N-acetylgalactosamine) deacetylase, polysaccharide deacetylase, and UDP-3-O-(R-3-hydroxymyristoyl)-N-acetylglucosamine deacetylase. For example, histone deacetylase hydrolyzes n-acetyl groups on histones, and citrate (pro-3S)-lyase deacetylase catalyzes conversion of enzymatically active acetyl-s-citrate lyase (4.1.3.6) into inactive hs-form and acetate. Particular nuclear acetyltransferases and deacetylases, such as histone deacetylase (HDAC), are involved in myogenesis, such as in the regulation of muscle-gene expression and resulting cellular differentiation.

Deacetylase inhibitor: An agent that inhibits the activity of a deacetylase. The inhibitor can be competitive or noncompetitive, and can interfere with deacetylase activity by affecting the enzymatic activity, disrupting the spatial conformation of the deacetylase, or interfering with transcription or translation pathways leading to production of the deacetylase. The DI can be any agent, including, but not limited to, chemical compounds, proteins, peptidomimetics, and antisense molecules or ribozymes. Exemplary deacetylase inhibitors include (but are not limited to): sodium butyrate, trichostatin A (TSA) and valproic acid (VPA). Another specific, non-limiting example of a deacetylase inhibitor is an antisense RNA or ribozyme that specifically binds mRNA encoding a deacetylase and inhibits translation of the mRNA. Particular classes of deacetylase inhibitors can be used, such as a histone deacetylase inhibitor, or inhibitors of any other deactylases, such as any of the deacetylases described herein.

Differentiated cell: A cell distinguished from an undifferentiated progenitor cell. The state of differentiation in progenitor cells versus their progeny cells can be identified morphologically or biochemically. For example (and without limitation), undifferentiated muscle progenitor cells generally appear round in shape and are uninucleated, while more differentiated muscle cells take on morphological aspects of their terminal cell types, such as being elongated and multinucleated. Therefore, undifferentiated progenitor cells can be selected by detecting their morphological characteristics under a light or electron microscope.

Additionally, differentiated cells can express different genes, including antigen expression, than those expressed in their undifferentiated progenitor cells. In a specific, non-limiting example, MHC is expressed in differentiated myotubes, but not expressed in undifferentiated myoblasts. The cellular-specific genes of undifferentiated progenitor cells are transcriptionally and/or or translationally silent in the undifferentiated cell, but later become active as differentiation begins.

Figure 10A:
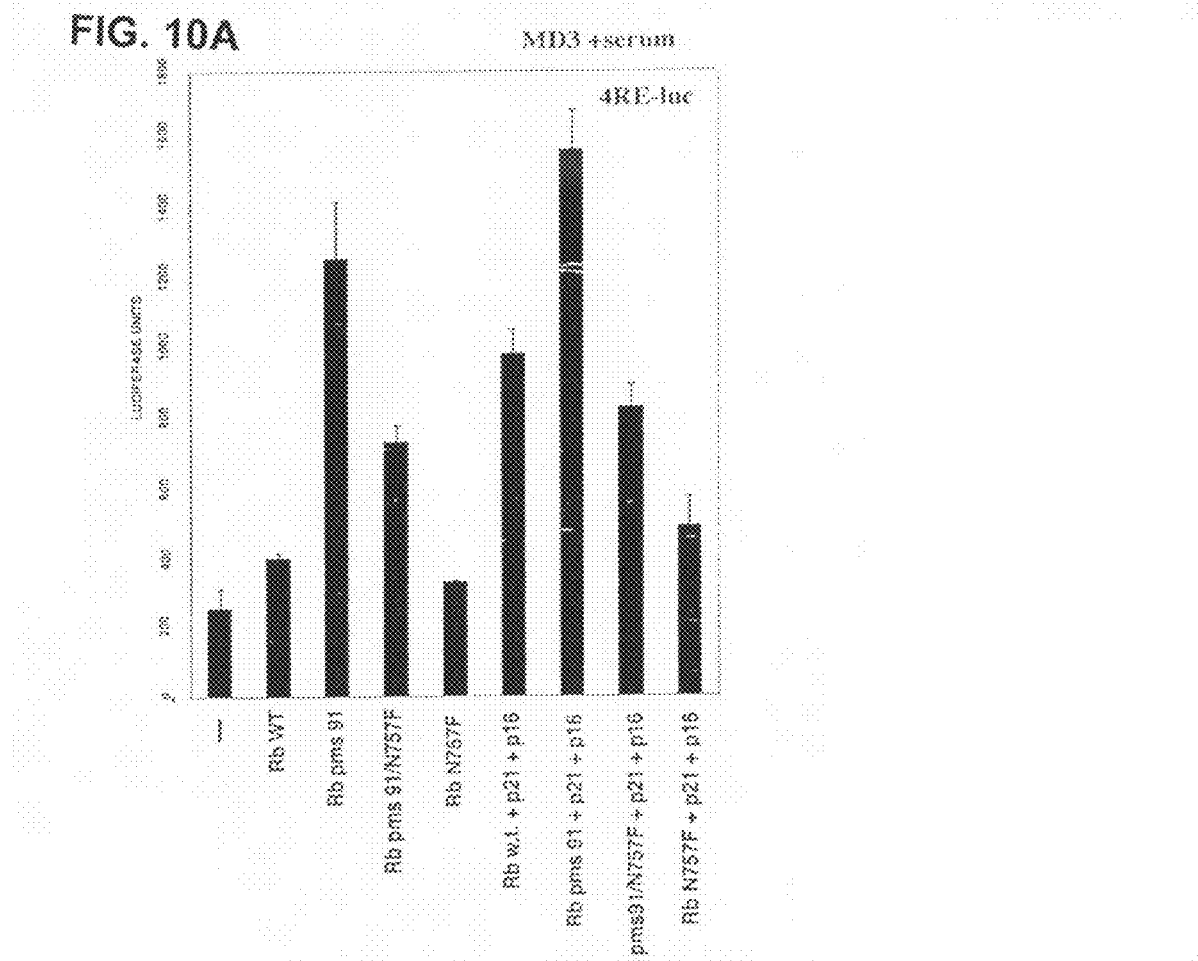
FIGS. 10A-C show that pRb dephosphorylation is required to dissociate the HDAC1-MyoD interaction and to activate muscle-gene expression.
Figure 10B:
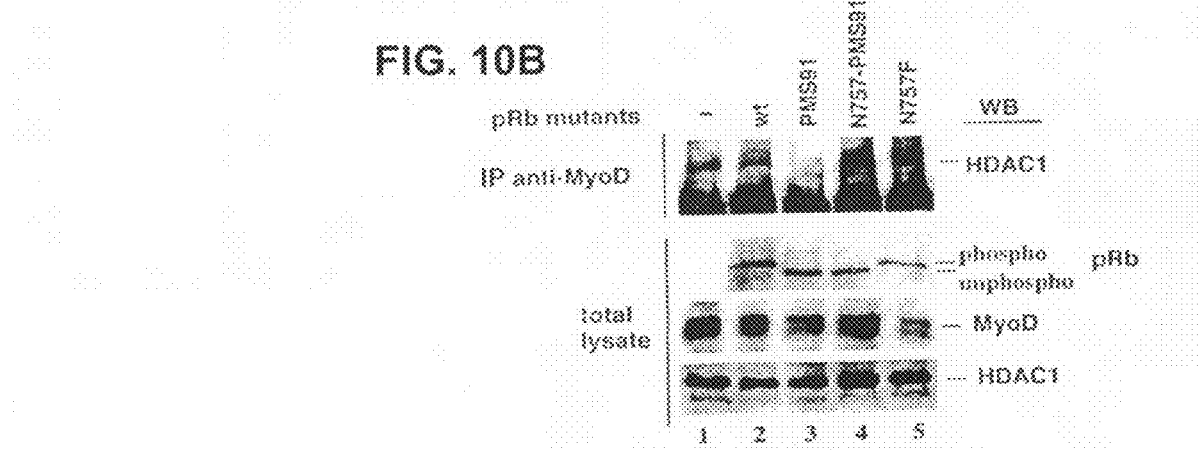
Figure 10C:
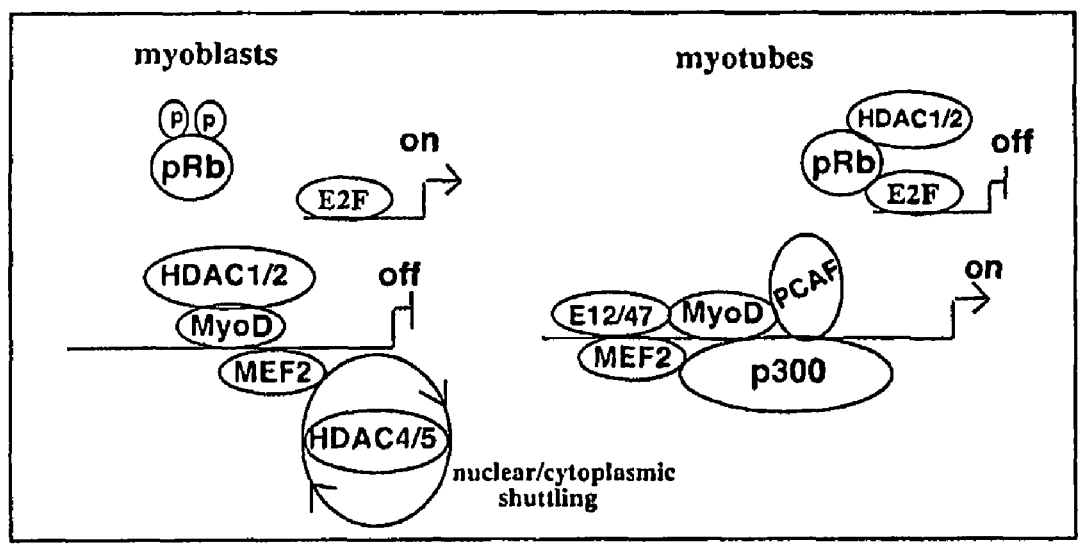

Undifferentiated progenitor cells also can be identified apart from differentiated cells based on particular molecular interactions. For example (and without limitation), as illustrated in FIG. 10C (and explained in further detail below), MyoD complexes with HDAC1 in undifferentiated myoblasts and blocks transcription of muscle-specific genes. Upon cellular differentiation, the levels of HDAC1 decline and residual HDAC1 is recruited by pRb, thus removing the transcriptional block of muscle-specific genes. In differentiated myotubes, HDAC1 no longer associates with MyoD, and MyoD complexes with the acetyltransferase PCAF, a protein whose acetylase activity is required for MyoD function, and muscle-specific genes are transcribed. Therefore, in addition to a lack of muscle-specific gene expression, undifferentiated myoblasts can be identified by detection a HDAC1/MyoD interaction.

E2F: The E2F protein is a component of normal cell cycle regulation. As a transcription factor, it positively regulates many of the genes required for initiation of S phase (the DNA synthetic phase) of the cell cycle. In mammals, E2F is held inactive by the retinoblastoma (Rb) family of pocket proteins. Hypophosphorylated Rb can interact with E2F during the G1 phase of the cell cycle, and this complex can bind to DNA and repress transcription of E2F target genes. If Rb is inactivated, such as by hyperphosphorylation carried out by cyclin dependent kinases, E2F is released and is allowed to activate genes required for DNA synthesis and entry into the S phase of the cell cycle.

Glyceraldehyde-3-phosphate dehydrogenase (GAPDH): A glycolytic enzyme that catalyses the reversible oxidative phosphorylation of glyceraldehyde-3-phosphate. One exemplary, non-limiting example of GAPDH is the protein encoded by the nucleic acid sequence of GenBank Accession No. NM_008084 (SEQ ID NO: 9).

Histone deacetylase (HDAC): A family of zinc hydrolases that modulate gene expression through deacetylation of the N-acetyl lysine residues of histone proteins and other transcriptional regulators. Three distinct families of human HDACs have been identified. Class I HDACs are expressed in most cell types, for example, HDAC1, which acts as a co-repressor for the Rb tumor suppressor protein. Class II HDACs such as HDAC4, are tissue-specific proteins implicated in the regulation of muscle differentiation. One exemplary, non-limiting example of HDAC1 is the protein encoded by the nucleic acid sequence of GenBank Accession No. NM_004964 (SEQ ID NO: 12), and one exemplary, non-limiting example of HDAC4 is the protein encoded by the nucleic acid sequence of GenBank Accession No. NM_006037 (SEQ ID NO: 13).

Hybridization: Hybridization of a nucleic acid occurs when two complementary nucleic acid molecules undergo at least some degree of hydrogen bonding to each other. The stringency of hybridization can vary according to the environmental conditions surrounding the nucleic acids, the nature of the chosen hybridization method, and the composition and length of the nucleic acids used. Temperature and ionic strength (for example, the $Na^+$ concentration) can affect the stringency of hybridization. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part 1, Chapter 2 (Elsevier, New York, 1993).

By way of illustration only, hybridization can occur by melting and reannealing a double-stranded nucleic acid, such as a dsDNA. The term $T_m$ represents the temperature at which 50% of a given strand of nucleic acid is hybridized to its complementary strand.

The $T_m$ of a particular nucleic acid can be determined by observing the transition state between a single-stranded and double-stranded state during a temperature change, such as heating a dsDNA from about 30° C. to about 100° C., and detecting when the dsDNA denatures to ssDNA. This can be accomplished by determining a melting profile for the nucleic acid.

Additionally, a $T_m$ an immobilized nucleic acid can be determined according to following equation:

$$T_m=81.5\ C-16.6(\log_{10}[Na^+])+0.41(\%G+C)-0.63(\%\text{formamide})-(600/l)$$

Where l=the length of the hybrid in base pairs.

This equation is valid for concentrations of Na⁺ in the range of 0.01 M to 0.4 M, and it is less accurate for calculations of $T_m$ in solutions of higher [Na⁺]. The equation is also primarily valid for nucleic acids whose GC content is in the range of 30% to 75% and whose length is about 100 nucleotides or greater.

For oligonucleotides of about 20 bases, the classical formula for $T_m$ is: $T_m=2\times(A+T)+4\times(G+C)$.

For longer nucleic acid fragments, such as PCR products, the nearest-neighbor method can be used to determine $T_m$. See, e.g., Breslauer K. J., et al., Proc. Natl. Acad. Sci. USA 83:3746-50 (1986). Additionally, the MeltCalc software can be used to determine $T_m$. See, e.g., Schultz, E. and von Ahsen, N., Biotechniques 30:8018-22, 24 (1999).

The $T_m$ of dsDNA decreases by about 1.0 to 1.5° C. with every about 1% decrease in sequence homology. For example, a heteroduplex dsDNA of about 100 bp with an SNP has a $T_m$ about 1.0 to 1.5° C. lower than a corresponding homoduplex dsDNA.

For purposes of this disclosure, "stringent conditions" encompass conditions under which hybridization will only occur if there is less than 25% mismatch between the hybridization molecule and the target sequence. "Stringent conditions" can be considered according to particular levels of stringency. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Isolated: An "isolated" cell (such as a progenitor cell) has been substantially separated or purified away from cells and/or microbes of different types, strains, or species. For example, an "isolated" culture of neuronal progenitor cells would be substantially free of bacteria, fungi, or other microbes and other types of cells, such as other types of progenitor cells or differentiated cells. Progenitor cells can be isolated by a variety of techniques.

An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

MCK: Muscle creatine kinase, a dimeric enzyme that catalyzes the formation of ATP from ADP and creatine phosphate in muscle. One exemplary, non-limiting example of MCK is the protein encoded by the nucleic acid sequence of GenBank Accession No. M21390 (SEQ ID NO: 8).

MLC1: A myosin alkali light chain expressed in fast skeletal muscle. Sometimes abbreviated as MYL1. One exemplary, non-limiting example of MLC1 is the protein encoded by the nucleic acid sequence of GenBank Accession No. NM_079422 (SEQ ID NO: 10).

MEF2C: One of the members of the myocyte enhancer factor-2 (MEF2) family of MADS-box transcription factors. Expressed in skeletal, cardiac and smooth muscle cells. Four vertebrate MEF2 proteins have been identified-MEF2A, MEF2B, MEF2C and MEF2D-whose products bind as homodimers and heterodimers to an A/T-rich DNA sequence in the control regions of numerous of musclespecific genes. One exemplary, non-limiting example of MEF2C is the protein encoded by the nucleic acid sequence of GenBank Accession No. NM_002397 (SEQ ID NO: 14).

Myoblast: An undifferentiated progenitor cell for myotubes and muscle cells (including cardia, skeletal, and smooth muscle cells).

MyoD: Considered a master regulatory protein involved in the determination of muscle cells (one of several proteins considered to be involved in muscle determination), MyoD activates or controls the transcription of many muscle-specific genes. Normally expressed in myoblasts and skeletal muscle cells, MyoD can convert some other types of cells into muscle cells if transfected into such other cells. MyoD is a nuclear protein with a helix-loop-helix dimerization domain and can form homodimers or heterodimers with other members of the bHLH (basic helix-loop-helix) superfamily. One exemplary, non-limiting example of MyoD is the protein encoded by the nucleic acid sequence of GenBank Accession No. XM_124916 (SEQ ID NO: 7).

Myogenin: A member of the MyoD family of muscle regulatory proteins that is related to the myc proto-oncogene family. One exemplary, non-limiting example of myogenin is the protein encoded by the nucleic acid sequence of GenBank Accession No. NM_031189 (SEQ ID NO: 6).

Myotube: Elongated, multinucleate cells that contain some peripherally located myofibrils. Myotubes are formed by the fusion of myoblasts and eventually develop into mature muscle fibers that have peripherally located nuclei and most of their cytoplasm filled with myofibrils.

Myosin heavy chain (MRC): A structurally bound contractile protein of the thick filaments of muscle cells. One exemplary, non-limiting example of MHC is the protein encoded by the nucleic acid sequence of GenBank Accession No. M9_2099 (SEQ ID NO: 5).

Oligonucleotide: A linear polynucleotide sequence of between 5 and 100 nucleotide bases in length.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Pharmaceutical agent, pharmaceutical composition, or drug: Refers to a chemical compound or composition capable of inducing a desired therapeutic or prophylactic effect when properly administered to a subject. Pharmaceutically acceptable salts of deacetylase inhibitors include, but are not limited to, those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts can be prepared by standard procedures, for example by reacting the free acid with a suitable organic or inorganic base. A deacetylase inhibitor alternatively can be administered as a pharmaceutically acceptable salt thereof or as part of a pharmaceutical composition, as disclosed herein.

Pharmaceutically acceptable carriers useful in this disclosure are conventional. Martin, *Remington's Pharmaceutical Sciences*, published by Mack Publishing Co., Easton, Pa., 19th Edition, 1995, describes compositions and formulations suitable for pharmaceutical delivery of the compositions herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Progenitor cell: A "progenitor cell" is a cell that gives rise to progeny in a defined cell lineage. For example, a "hematopoietic progenitor cell" is a cell that gives rise to cells of the hematopoietic lineage, a "muscle progenitor cell" is a cell that gives rise to cells of the skeletal and cardiac muscle lineage, and a "neuronal progenitor cell" is a cell that gives rise to the cells of nervous tissue. A progenitor cell can remain a progenitor cell, or can proceed to terminal differentiation.

Purified: The term "purified" does not require absolute purity. Rather, "purified" is a relative term. Thus, for example, a purified biological component (such as a cell) is one in which the component is more enriched than in its natural environment, such as within the body or within a cell. For example, a purified cell culture can be one in which at least 50% of the total number of cells in the culture are of the same type as the cell of interest.

Retinoblastoma protein (Rb): A nuclear phosphoprotein that normally acts as an inhibitor of cell proliferation. Rb is absent in retinoblastoma cell lines. One exemplary, non-limiting example of Rb is the protein illustrated by the amino acid sequence of GenBank Accession No. A33_718 (SEQ ID NO: 11).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, can be expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a protein or nucleic acid disclosed herein will possess a relatively high degree of sequence identity when aligned using standard methods. This homology will be more significant when the orthologous proteins or nucleic acids are derived from species that are more closely related (e.g., human and chimpanzee sequences), compared to species more distantly related (e.g., human and *C. elegans* sequences).

Methods of alignment of sequences for comparison are known. Various programs and alignment algorithms are described in: Smith & Waterman Adv. Appl. Math. 2: 482, 1981; Needleman & Wunsch J. Mol. Biol. 48: 443, 1970; Pearson & Lipman Proc. Natl. Acad. Sci. USA 85: 2444, 1988; Higgins & Sharp Gene, 73: 237-244, 1988; Higgins & Sharp CABIOS 5: 151-153, 1989; Corpet et al. Nuc. Acids Res. 16, 10881-90, 1988; Huang et al. Computer Appls. in the Biosciences 8, 155-65, 1992; and Pearson et al. Meth. Mol. Bio. 24, 307-31, 1994. Altschul et al. (J. Mol. Biol. 215:403-410, 1990), presents a detailed consideration of sequence alignment methods and homology calculations.

The NCBI Basic Local Alignment Search Tool (BLAST) (Altschul et al. J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions (described above). Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

A first nucleic acid is "substantially similar" to a second nucleic acid if, when the first nucleic acid is optimally aligned (with appropriate nucleotide deletions or gap insertions) with the second nucleic acid (or its complementary strand) and there is nucleotide sequence identity in at least about, for example, 50%, 70%, 75%, 80%, 85%, 90%, 95%, or 99% of the nucleotide bases.

Transfected: A transfected cell is a cell into which a nucleic acid has been introduced by molecular biology techniques. The terms "transfection," or "transformation," encompass all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector can include nucleic acid sequences that permit it to replicate in a host cell, such as an origin of replication. A vector also can include one or more selectable marker genes and other genetic elements.

Deacetylase Inhibition and the Effects on Progenitor Cell Growth and Differentiation Contacting a progenitor cell with a deacetylase inhibitor (DI) produces different effects on gene transcription and cellular differentiation, depending on the stage of cell differentiation at which a DI is applied. It has been previously described that, if a DI is applied to a differentiated cell, further differentiation of that cell is inhibited or prevented. Surprisingly, however, as demonstrated herein, when a DI is applied to an undifferentiated progenitor cell, the DI promotes gene expression leading to differentiation of the progenitor cell. The DI can then be removed, once the progenitor cell has been induced to differentiate, to allow further differentiation of that cell.

These effects are observed in different types of progenitor cells, including human adult primary skeletal muscle cells and mouse embryos. A DI can be used to promote cell differentiation, growth, and regeneration of muscle cells, hematopoieic cells, and neuronal cells. A DI can be used for prophylatic or therapeutic applications to inhibit, prevent, or treat pathological conditions associated with deterioration of tissue, such as muscular dystrophy, neurodegenerative disorders, and conditions characterized by decreased production and/or increased destruction of hematopoietic cells, such as anemia, bone marrow loss due to anti-tumor radiation therapy or chemotherapy, or in destruction of cells resulting from an infectious agent. Additionally, the effect of a DI a can be assisted by the retinoblastoma protein (Rb).

DI exposure during the undifferentiated progenitor cell stage promotes gene expression leading to cellular differentiation. For example, in undifferentiated myoblasts, application of a DI produces an increase in the formation of multinucleated myotubes, and DI applied to cultured myoblasts promotes expression of muscle-specific reporters and endogenous muscle proteins. For example, as shown in Example 1, the morphological changes that occur when a myoblast is contacted with a DI include a dramatic recruitment of nuclei in terminally differentiated myotubes, with less than about 20% of the total nuclei being present in MHC-negative cells. These results are in contrast with cultures of non-treated myotubes, which exhibit up to about 84% of nuclei present in MHC negative cells. See Table 1.

In one embodiment, myoblasts exposed to a DI (such as by targeting the HDAC/MyoD interaction, explained in further detail below) causes activation of muscle gene expression and a dramatic increase in myotube formation upon subsequent incubation in differentiation medium (DM), a medium permissive for cellular differentiation.

Conversely, differentiated muscle cells exposed to DI and incubated in DM result in the activation of E2F-dependent transcription and repression of terminal differentiation. Myocytes derived from pRb−/−mice (in which the HDAC1/MyoD interaction persists in DM due to the absence of pRb) are resistant to the repressive effects of DI in DM, thus demonstrating that pRb is involved in mediating the effects of HDAC inhibition at distinct stages of the myogenic program.

Additionally, embryos exposed in utero to non-teratogenic doses of a DI display effects correlated to those observed in cell culture. For example, embryos contacted with a DI in utero can display an increased number of somites and augmented expression of a muscle-specific transgene. Thus, both somitogenesis and muscle transcription are promoted upon exposure to non-teratogenic doses of a DI. Therefore, DIs can be used to manipulate cellular differentiation both in culture and in animal models.

Without being bound by one particular theory, one explanation for the surprising effects of a DI on undifferentiated progenitor cells involve the interaction of HDAC1, MyoD, and pRb. Briefly, HDAC1 inhibits MyoD activity in undifferentiated myoblasts, but HDAC1 is required in myotubes to mediate the pRb-dependent blockade of genes controlling cell cycle progression, therefore promoting cell cycle arrest, a prerequisite for terminal differentiation. A DI that inhibits HDAC1 in undifferentiated progenitor cells therefore inhibits the HDAC1/MyoD interaction, which reverses the normal repression of transcription of muscle-specific genes and allows those genes to become active. Conversely, a DI that inhibits HDAC1 in differentiated myotubes inhibits the HDAC1/pRb interaction that normally represses E2F transcription, and the resulting activation of E2F transcription in myotubes represses terminal differentiation. These interactions are explained in further detail in the Examples below.

In addition, without being bound by one particular theory, the effects of DI on developing embryos involve the control of the Notch signaling pathway. Notch transcripts are increased in animals exposed to a DI, such as TSA. The Notch signaling pathway has been shown to regulate boundary formation that accompanies the generation of newly formed somites. Specifically, Lunatic fringe can modulate the effects of the Notch signaling pathway by causing periodic bursts of Notch activation with a periodicity that coincides with the time required to form two somites. Therefore, a DI, such as TSA, can promote somitogenesis by providing a continuous stimulation of the Notch pathway outside the control of Lunatic fringe.

The effects of DI exposure on other types of progenitor cells, such as neuronal and hematopoietic progenitor cells, is similar to that observed for muscle progenitor cells. Without being bound by a specific theory, the survival and differentiation of hematopoietic and neuronal progenitor cells depend on bHLH transcription factors whose activity—like that of MyoD and MEF2—is modulated by acetyltransferases and depend on the functional integrity of pRb. Therefore, because the molecular mechanisms are similar in muscle, neuronal, and hematopoeitic progenitor cells, the effects of DI on these different types of progenitor cells are believed to be similar; a DI that inhibits a deacetylase in undifferentiated neuronal or hematopoietic progenitor cells will inhibit a deacetylase/bHLH transcription factor interaction (similar to the HDAC1/MyoD interaction), which will reverse the normal repression of transcription of cell-specific genes and allow those genes to become active.

Methods of Using Deacetylase Inhibitors to Control Cellular Differentiation

A DI can be used to promote cellular differentiation, growth, and regeneration of progenitor cells of muscle cells, hematopoiteic cells, and neuronal cells. The progenitor cells can be part of cell culture or can be located within a subject. Generally, a progenitor cell, such as a progenitor cell in culture, is contacted with an amount of a DI effective to promote growth, regeneration, or differentiation of the progenitor cell. For example, a culture of undifferentiated progenitor cells can be grown and, just prior to transplantation into a host, can be contacted with an amount of a DI effective to initiate differentiation into more specialized cells. Additionally, the effects of a DI can be supplemented by coadministration of retinoblastoma (Rb) protein. Once the transplanted progenitor cells are introduced into the host subject, the DI concentration around the transplanted cells decreases and does not interfere with further courses of differentiation of the transplanted cells within the host. Alternatively, the DI can be reduced or removed from the progenitor cell environment prior to transplantation. Progenitor cells can be transplanted in ways similar to transplanting stem cells, and exemplary cell transplantation techniques can be found in U.S. Pat. Nos. 5,928,947; 5,817,773; and 5,800,539, and PCT publications WO 01/176507 and WO 01/170243.

An effective amount of a DI can be administered to a subject, such as a human or other mammal, to promote the growth, regeneration, or differentiation of progenitor cells within that subject, with or without progenitor cell transplantation. Administering a DI to a subject is believed to alleviate symptoms of various pathological conditions and diseases associated with tissue degeneration or tissue loss. Such tissue-wasting conditions and diseases include those that destroy tissue, reduce cellular size or number within a tissue, impair the functioning of tissue, or otherwise diminish a mass of tissue, for example, through non-use (such as muscular atrophy), an infective agent (such as viral destruction of cells), a toxin (such as bone marrow loss during chemotherapy), or genetic mutation (such as anemia). Exemplary tissue-wasting diseases and conditions include (but are not limited to): muscular atrophy, muscular dystrophy, muscular cachexia, dermatomyositis, Alzheimer's disease, olivopontocerebellar atrophy, Parkinson's disease, degeneration of nervous tissue, ocular atrophy, alcohol-induced brain damage, hepatocerebral degeneration, idiopathic aplastic anemia, secondary aplastic anemia, post-ischemic tissue degeneration, amyotrophic lateral sclerosis, poliomyolitis, bone marrow loss induced by radiation therapy or chemotherapy, multiple myeloma, acute lymphocytic leukemia, HIV infection, AIDS, malaria, chronic myelogenous leukemia, Fanconi's anemia, or trauma. Additionally, administering a DI to a subject can provide a prophylactic effect leading to the inhibition or prevention of such diseases or conditions.

For example, a subject at risk of suffering some muscle-wasting disease, such as muscular dystrophy, and/or some neurodegenerative disease, such as Alzheimer's disease, can be administered an amount of a DI effective to promote growth and differentiation of progenitor cells within that subject, thus replacing dead or dying cells of muscle or nervous tissue. Such a subject need not be diagnosed with a particular disease, since administering a DI effective to promote growth and differentiation of progenitor cells within that subject can provide a prophylactic effect. As another example, a subject partially or totally immobilized after injury or trauma can suffer muscular atrophy, which can be alleviated by administering a DI to the subject to promote muscle progenitor cell growth, regeneration, and differentiation to replace atrophied muscle tissue. As another, non-limiting example, subjects undergoing anti-tumor chemotherapy or radiation therapy, who suffer degeneration of hemopoietic tissues, can be administered an amount of a DI effective to promote regeneration and differentiation of hemopoetic progenitor cells within that subject. As yet another, non-limiting example, a subject suffering (or at risk of suffering) aplastic anemia, or other degenerative disease of the bone marrow, can be treated by administering an effective amount of a DI that promotes the growth, regeneration, and differentiation of hematopoetic progenitor cells.

In some embodiments, the prophylactic and/or therapeutic effects of promoting progenitor cell growth, regeneration, and/or differentiation are provided by administering to a subject a therapeutically effective amount of a DI as part of a pharmaceutical composition. The pharmaceutical composition can include plural DIs; pharmaceutically compatible carriers, agents, counterions, adjuvants, or vehicles; or combinations thereof. Although the treatment can be used prophylactically in any patient in a demographic group at significant risk for suffering a disease or condition associated with tissue degeneration and/or loss, subjects also can be selected using more specific criteria, such as a definitive diagnosis of a particular infection, disease, or condition, or identification of a particular genotype, such as the presence of a genetic marker associated with a particular disease or condition.

Providing a pharmaceutical composition to a subject includes methods of administering that composition. Routes of administration include, but are not limited to, oral and parenteral routes, such as intravenous (IV), intraperitoneal (IP), rectal, topical, ophthalmic, nasal, and transdermal. If orally bioavailable DIs are used, the pharmaceutical compositions can be provided or administered in the form of a unit dose in solid, semi-solid, or liquid dosage forms such as tablets, pills, powders, liquid solutions, or liquid suspensions. However, the drugs also can be administered intravenously in any conventional medium for intravenous injection, such as an aqueous saline medium, or in a blood plasma medium. The medium also can contain conventional pharmaceutical adjunct materials, such as those found in Remington: The Science and Practice of Pharmacy (19$^{th}$ Edition, 1995) in chapter 95.

Therapeutically effective amounts of compounds of the present invention can be determined in many different ways, depending on the toxicity of the DI or its teratogenic threshold. In certain embodiments, the DI is administered to provide plasma levels of about 10 to about 500 µg/mL, such as about 50 to 300 µg/nl, or about 100 to 150 µg/mL. As one particular, non-limiting example, valproic acid can be administered at a dose that achieves plasma levels of about 150 µg/mL. Valproic acid is available in an oral dosage form which can be administered, for example, at dosages of 15-60 mg/kg/day. Serum levels of the drug can be determined to determine whether therapeutic levels have been achieved The specific dose level, frequency of dosage, and duration of treatment for any particular subject can be varied and will depend upon a variety of factors, including: the activity of the specific pharmaceutical composition; the metabolic stability and length of action of that composition; the age, body weight, general health, sex, diet, and other characteristics of the subject; mode and time of administration; the rate of excretion; drug combination parameters; and severity of the condition of the subject undergoing treatment.

Since a DI can inhibit further differentiation of cells once they convert from undifferentiated progenitor cells to differentiated cells, pulsatile administration of the DI can be used in some embodiments. For example, a sufficient single or pulse dose is administered to raise the tissue concentration of the drug in the vicinity of the target progenitor cells of interest to a level that is similar to that at which cellular differentiation is observed to be induced in culture. Administration of the DI is then discontinued so that tissue concentrations fall below the level at which the DI has been found to inhibit further differentiation of already differentiated cells. Once the full effect of the DI has been realized, and the induced cells have differentiated and matured, another dose of the DI is administered.

Many variations on this pulsatile administration regimen are possible, and clear separation between induction of undifferentiated progenitor cells and further maturation of already differentiated cells is not essential. For example, rounds of DI induction or differentiation can overlap within periods of further maturation of the cells in which differentiation has already been induced.

EXAMPLES

The following examples are provided to illustrate particular features of certain embodiments, but the scope of the claims should not be limited to those features exemplified.

Example 1

Modulation of the Myogenic Program by Inhibitors of Nuclear Deacetylases in Cultured Cells and in Developing Embryos When a DI is applied to undifferentiated myoblasts, and then removed once cells are induced to differentiate, the DI promotes muscle gene expression and differentiation. However, in the presence of a DI, further differentiation of induced cells is inhibited or prevented. This phenomenon correlates with hyperacetylation of MyoD, of histones surrounding the MCK enhancer, and transcriptional activation.

Cells, Plasmids, Transfections and Luciferase Reporter Assay

Mouse muscle myoblast C2C12 cells (obtained from the American Type Culture Collection, ATCC CRL-1772) and CC42 cells (from Dr. Kenneth Walsh, Tufts University School of Medicine) were cultured in DMEM supplemented with 20% fetal bovine serum, 2 mM glutamine and 1× kanamycin (growth medium, GM). Cellular differentiation was induced with DMEM supplemented with 2% horse serum and 1× insulin, transferring, selenium (Life Technologies). Human skeletal myocytes (CC-2561) were purchased from Clonetics. Stable C2C12 cell lines with integrated reporters are described in Wu, Z., et al., *Mol Cell Biol* 20:3951-64 (2000). The MCK-luc, 4RE-luc, MEF2 reporter constructs have been described in Puri, P. L., et al., *EMBO Journal* 16:369-83 (1997a) and Sartorelli, V., et al., *Molecular & Cellular Biology* 17:1010-26 (1997). The E2F-luc plasmid is described in Helin, K., et al., *Genes Dev* 7:1850-61 (1993). The MLC-lacZ-nls plasmid is described in Wu, et al. (2000). Dr. Stuart Schreiber (Harvard University) provided the vector expressing Flag-HDAC1, which is described in Taunton, J., et al., *Science* 272: 408-11 (1996). Transient transfections were performed using FuGENE 6 transfection reagent (Roche Molecular Biochemicals). Following transfections, luciferase activity was determined using the Dual-Luciferase reporter assay system (Promega) on a microtiter luminescence detection system (MLX, Dynex).

Immunoblotting and Immunofluorescence

For immunoblotting, cell extracts were obtained after incubating the cells in standard lysis buffer. Western blots were probed with the following antibodies: anti-MHC (MF-20), anti-myogenin (FD5), and anti-tubulin (E7), obtained from the Developmental Studies Hybridoma Bank, University of Iowa. Primary antibodies were visualized with the ECL cheminoluminescent kit (Amersham). Cells were fixed and stained with anti-MHC MF-20 antibodies. Nuclei were visualized by 4',6'-diamino-2-phenylindole (DAPI). FITC-conjugated or Texas red-conjugated secondary antibodies were employed to reveal the primary antibodies.

Muscle Creatine Kinase Assay

The activity of endogenous muscle creatine kinase in C2C12 muscle cells was measured following the procedures of the commercial kit (Sigma). Cells were washed in TBS and the cell extracts used for the assay were prepared in TBS-containing buffer with 1% Tween, phosphatase, and proteases inhibitors.

Deacetylase Inhibitors Treatment

C2C12 and CC42 cells were exposed to sodium butyrate 5 mM (Sigma), trichostatin A 50 nM (Upstate Biotechnologies), or valproic acid 10 mM (Sigma) for 24 hours in GM (GM regimen). TSA was removed and the cells cultured in DM for 48 hrs before being analyzed. When indicated (DM regimen), the cells were exposed to deacetylase inhibitors when switched from GM to DM and cultured in their presence for 48 hrs.

β-Galactosidase Assay

Cells transfected with MLC-lacZ-nls were washed twice in PBS, fixed in 4% paraformaldeheyde-PBS for 5 min, washed twice in PBS, and stained for 2-5 hrs with 5 mM potassium ferrycyanide, 5 mM potassium ferrocyanide, 2 mM $MgCl_2$, 1 mg/ml X-gal (5-bromo-4-chloro-3-indolyl-β-D-galactoside).

In Vivo Acetylation Assay

In vivo acetylation assay was performed as described in Sartorelli, V., et al., *Molecular Cell* 4:725-34 (1999).

Chromatin Immunoprecipitation Assay (ChIP)

A ChIP assay was performed using the acetyl-histone H4 immunoprecipitation assay kit (Upstate Biotechnology) according to the manufacturer's instructions. PCR was performed on "input" DNA of different samples and equivalent amounts of immunoprecipitated DNA were amplified by PCR using primers for the GAPDH promoter and MCK enhancers. PCR conditions were: 1×95° C. 2 min, followed by 25 cycles at 95° C. for 30 sec, 55° C. for 30 sec, and 72° C. for 30 sec.

The primers used were:

```
GAPDH   5' GCTCACTGGCATGGCCTTCCG 3' ("sense")
        5' GTAGGCCATGAGGTCCACCAC 3' ("anti-sense")
MCK     5' GCCACTATGGGTCTAGGCTGC 3' ("sense")
        5' CGAGCTTCTCCTCCATGGTG 3' ("anti-sense")
```

The MCK primers amplify nucleotides −1229 to −1007 of the MCK enhancer, while the GAPDH primers amplify nucleotides −1030 to −721. The PCR products were analyzed on 6% non-denaturing polyacrylamide gels.

Embryo Manipulation

MLC1/3F-nLacZ pregnant mice (E 8.5) received intra peritoneal injection of 15 µg of TSA (WAKO chemicals, Neuss Germany) or VPA (Sigma) at E 8.5 and E 9.5 as described in Faiella, A., et al., *Hum Mol Genet* 9:227-36 (2000), and Nervi, C., et al., *Cancer Res* 61:1247-9 (2001). VPA was dissolved in distilled water and administered at doses of 6 mg/mice (about 150 µg/ml) every 12 h at E 8.5, E 9, E 9.5, E 10 as described in Faiella et al. (2000). VPA doses were in the therapeutic range in humans (50-150 µg/ml). Mice were sacrificed at E 10.5, and the embryos were observed under a dissecting stereo-microscope to evaluate their viability, presence of external malformations, and number of somites. Embryos were fixed in 4% paraformaldehyde for histology and X-Gal staining or immunocytochemistry using antibodies against MyoD and myosin heavy chains as described in Tajbakhsh, S., et al., *Neuron* 13:813-21 (1994).

The Effects of Deacetylases Inhibition on Skeletal Muscle Cells Depend on their Differentiation Stage Previously, the deacetylase inhibitor sodium butyrate has been reported to inhibit myogenic differentiation (see Background). In those studies the cells were exposed to the DI when cultured in differentiation medium (DM). In agreement with these findings, it was observed that the cells treated with sodium butyrate when cultured in DM failed to activate expression of both myogenin and the myosin heavy chain (MHC) and to properly differentiate (FIGS. 1A and B).

Numerous cells exposed to sodium butyrate in DM undergo a high frequency of apoptosis as indicated by the reduced cell density (FIG. 1B). The interaction of HDAC1 with pRb in DM blocks E2F-dependent transcription (see, e.g., Magnaghi-Jaulin, L., et al. (1998); Brehm, A., et al. (1998); and Luo, R. X., et al. (1998)) and activates muscle gene expression. However, exposure of skeletal myoblasts to DI during differentiation impinges on the function of the HDAC1-pRb complex and adversely affects muscle gene expression, since sustained E2F activity is incompatible with the activation of the myogenic program. See Wang, et al. (1995).

While HDAC1 associates with MyoD in undifferentiated skeletal myoblasts, HDAC1 is later recruited on hypophosphorylated pRb in differentiated skeletal myotubes. Indeed, DI exposure activates E2F-dependent transcription in myoblasts cultured in DM, but not in GM (see FIG. 2C). Thus, undifferentiated myoblasts exposed to a DI demonstrate a different outcome than differentiating myocytes exposed to a DI.

Undifferentiated myoblasts were exposed to sodium butyrate and allowed to differentiate in the absence of DI. Under these conditions, the cells upregulated MHC expression and displayed a striking increased frequency of larger MHC-positive multinucleated cells as compared to untreated cells (FIGS. 1C and D). MHC expression is restricted to late stages of muscle differentiation and requires the presence of functional pRb, whereas myogenin is activated at earlier stages and does not require pRb. See Novitch, B. G., et al., *Journal of Cell Biology* 135: 441-56 (1996).

To evaluate the effects of DIs on the activation of additional muscle-specific genes, an RT-PCR-mediated analysis was performed on the RNA obtained from cells exposed to a DI. Transcription of the late stage-specific gene muscle creatine kinase (MCK) was enhanced when compared to non-treated cells (FIG. 1C).

Two other structurally unrelated DIs, trichostatin A (TSA) and valproic acid (VPA), a short-chained fatty acid used as anticonvulsant and mood stabilizer recently shown to inhibit histone deacetylases (see Phiel, C. J., et al. *J Biol Chem* 25:25 (2001)) displayed effects undistinguishable from those exerted by sodium butyrate (FIGS. 1C and D). Hence, deacetylase inhibition not peculiar activities of the individual compounds-mediates the effects on myogenesis.

Figure 1D:
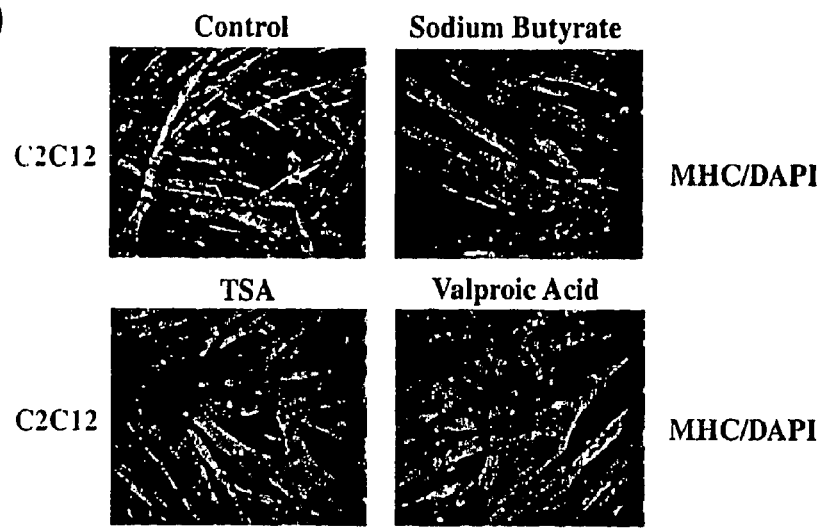

Another striking effect induced by DI is their ability to increase the number of nuclei present in MHC positive cells. While approximately 15% of the total nuclei are present in elongated, MHC-positive myotubes not exposed to DI, approximately 75-80% of the total nuclei are detected in hypernucleated MHC-positive myotubes when these have been previously exposed to DI (see FIG. 1D and Table 1). In Table 1, C2C12 cells were either exposed to sodium butyrate, TSA, VPA or left untreated for 24 hours in GM. The medium was replaced with DM without DI, and MHC expression was detected by immunofluorescent staining. Nuclei were visualized with DAPI. The values in parenthesis indicate the percentage of nuclei detected in MHC-positive cells. The values are derived from two independent trials.

TABLE 1

Deacetylase Inhibitors Augment the Percentage of Multinucleated Skeletal Myotubes

|  |  | Total Nuclei (DAPI) | Nuclei/ MHC-Positive Cells |
|---|---|---|---|
| Untreated | Tr. 1 | 240 | 33 (14%) |
|  | Tr. 2 | 250 | 42 (17%) |
| Sodium Butyrate | Tr. 1 | 250 | 210 (84%) |
|  | Tr. 2 | 274 | 230 (83%) |
| TSA | Tr. 1 | 266 | 200 (75%) |
|  | Tr. 2 | 320 | 210 (65%) |
| VPA | Tr. 1 | 187 | 153 (81%) |
|  | Tr. 2 | 240 | 187 (78%) |

Furthermore, fluorescence activated cell sorting (FACS) experiments showed that DI treatment does not prevent the normal accumulation of myoblasts in G0/G1 of the cell cycle once placed in DM.

The effect of DI exposure was further verified in primary human skeletal myocytes (HSkM). Again, exposure of these cells by TSA (FIG. 1E) or other DI, followed by incubation in DM, greatly enhanced the formation of MHC-positive myotubes and increased the MHC expression levels. The same effect was also observed in rat L6 myocytes (data not shown). These results indicate that the positive effect exerted by DI on muscle differentiation is general and not restricted to specific myogenic cell lineages.

Deacetylase Inhibitors Target the Muscle Regulatory Factors (MRFs)

Figure 1F:
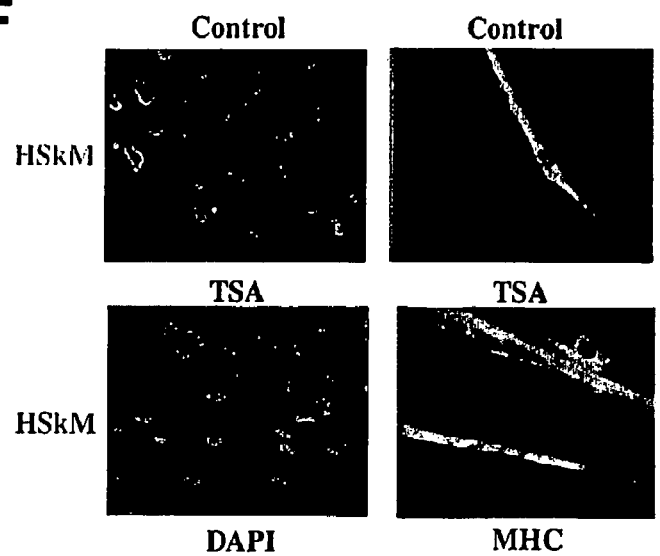
Figure 2A:
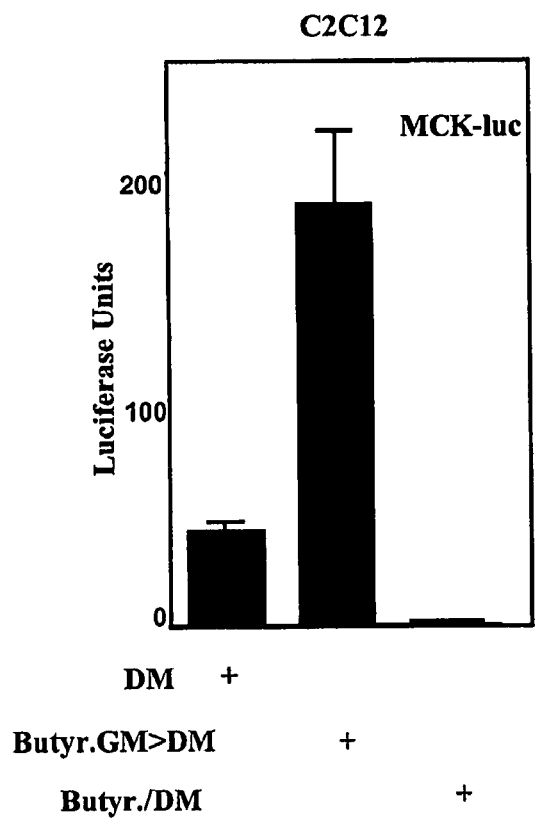
FIGS. 2A-D are graphs showing DI activation muscle-specific transcription in skeletal muscle cells.

Since exposure of undifferentiated myoblasts to TSA causes hyperacetylation of MyoD and of the histones within the chromatin of the MyoD-regulated MCK enhancer deacetylase inhibition can target the activity of the myogenic bHLH and possibly the MEF2 proteins. To demonstrate the effects of deacetylase inhibition, several myogenic reporters, whose activation relies mainly on myogenic bHLH proteins (4RE-luc), MEF2 factors (MEF2-luc) or both (MCK-luc), were transiently transfected in skeletal myoblasts, which were subsequently exposed to TSA or VPA treatment either in GM or DM. As shown in FIG. 2A, TSA treatment stimulates transcription of the reporter constructs only when the DI inhibitors are applied to the cells cultured in GM. These findings are in agreement with the behavior of the endogenous genes MHC and MCK upon DI treatment (FIG. 1).

Figure 2B:
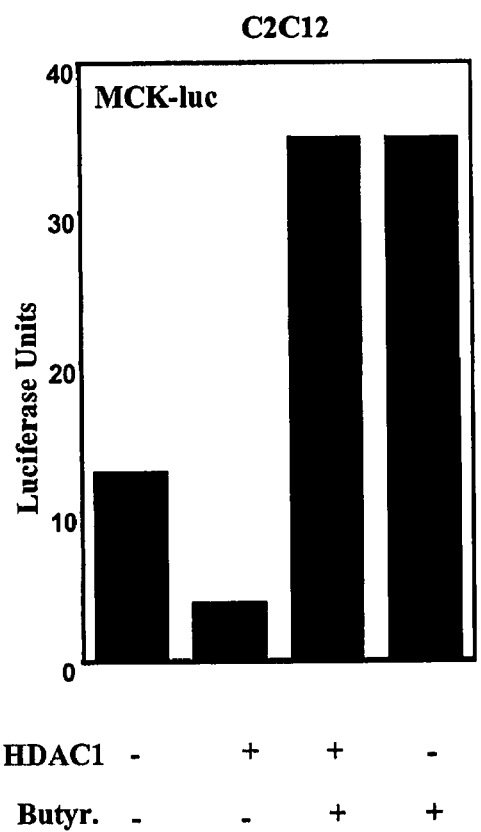
Figure 2C:
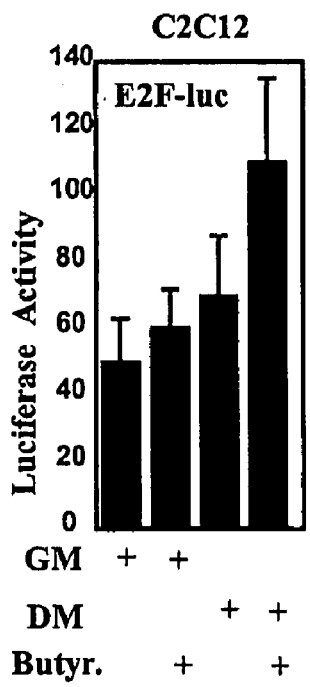

Since TSA targets class I as well as class II HDACs, inhibition of members belonging to both families of deacetylases can mediate the pro-differentiation effect of TSA. Nonetheless, HDAC1-mediated inhibition of 4RE-luc could be reversed by TSA treatment (FIG. 2B), indicating that blockade of class I deacetylases is involved in promoting muscle-transcription and differentiation. In contrast to the behavior of muscle-specific reporters, transcription driven from an E2F-responsive construct was stimulated by TSA when cells were exposed to DI in DM (FIG. 2C).

Figure 2D:
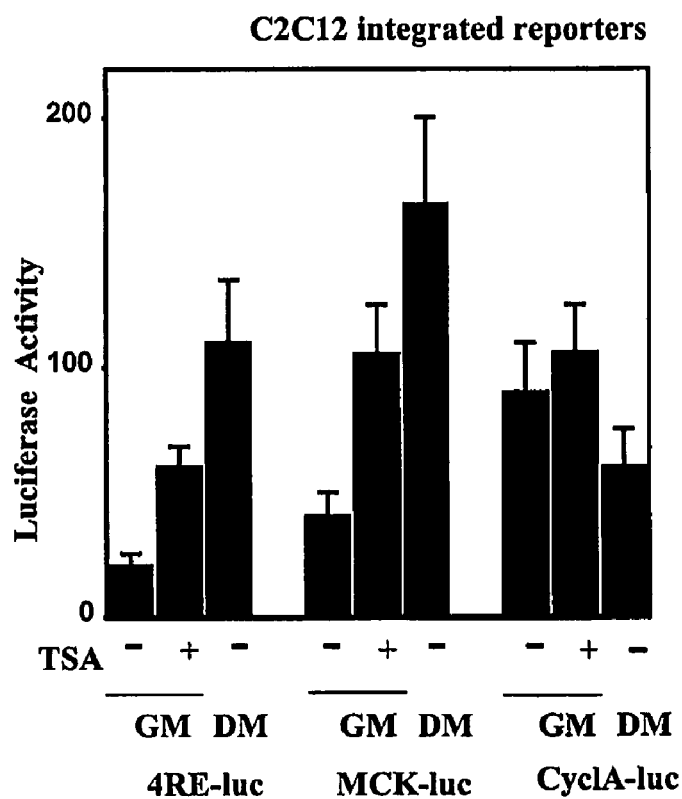

To strengthen and extend these observations, the effects of TSA on chromatin-integrated muscle-specific reporters were tested. C2C12 clones, stably transfected with 4RE-luc and MCK-luc templates, were used. These templates are repressed when the cells are cultured in GM, while exposure to TSA led to two-to-three fold activation in the presence of serum (FIG. 2D). On the contrary, serum-dependent transcription driven by an integrated cyclinA-luc construct was not stimulated by TSA treatment in GM (FIG. 2D). The difference in fold activation observed between transient (FIG. 2A) and stable (FIG. 2D) transfectants might be ascribed to either a different copy number of templates or to a tighter chromatin conformation of the integrated reporters.

Figure 3A:
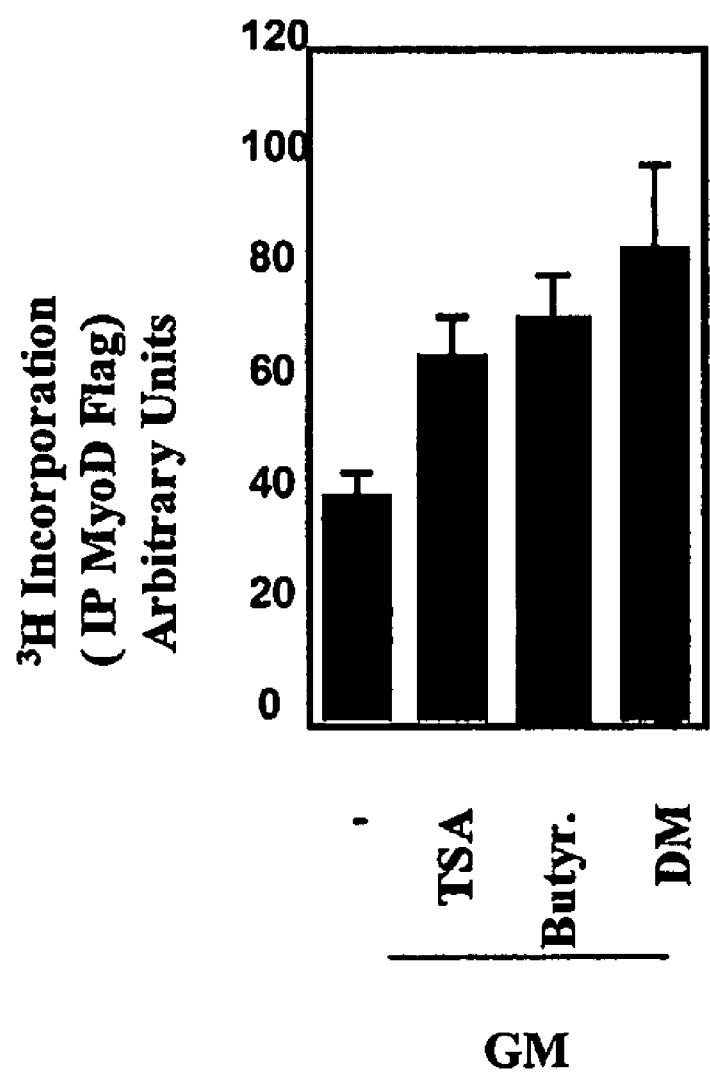

MyoD and Histone Acetylation Correlate with the Functional Outcomes of Deacetylases Inhibition The acetylation of MyoD by $^3$H-acetate incorporation in myoblasts, cultured in either the absence or presence of TSA, was evaluated. As shown in FIG. 3A, TSA exposure stimulated the incorporation of $^3$H-acetate into a MyoD transiently transfected into myoblasts cultured in GM to levels comparable to those detected upon placing the cells in DM. It appears that TSA-mediated hyperacetylation of MyoD is obtained mainly through inhibition of the enzymatic activity of HDAC1 and not through its displacement from MyoD.

The transcriptional state of a given gene can often be predicted by the acetylation of the histones positioned on its regulatory regions. Histone hyperacetylation marks transcriptionally active regions. See, e.g., Bone et al., *Genes De.* 8:96-104 (1994) whereas inactive chromatin domains are hypoacetylated. See, e.g., Braunstein, M., et al., *Genes Dev.* 7:592-604 (1993). To analyze the effects of TSA on histone acetylation, a chromatin immunoprecipitation (ChIP) assay using an antibody against hyperacetylated H4 histones was performed to evaluate the acetylation of the histones surrounding the E-boxes of the MCK enhancer. As shown in FIG. 3B, the histones located on the MCK enhancer are hypoacetylated in undifferentiated myoblasts and become hyperacetylated upon differentiation, in agreement with the kinetics of the MCK transcriptional activation. Exposure of undifferentiated myoblasts to TSA in GM resulted in activation of a transfected MCK-luc reporter (FIG. 2B), induction of endogenous MCK transcripts (FIG. 1C), and histone hyperacetylation of the MCK enhancer (FIG. 3C). Thus, the functional effects of TSA on muscle gene expression can be positively correlated with MyoD and histone acetylation of the MCK enhancer.

TSA and VPA Anticipate Somitogenesis and Activate Muscle Transcription in Developing Embryos To demonstrate the effects of deacetylase inhibition in an animal model, transcription directed by the myosin light chain 3F regulatory regions-lacZ (MLC3F-lacZ-nls) transgene (Kelly et al. 1995) were observed in developing mouse embryos exposed to either TSA or VPA.

Figure 4A:
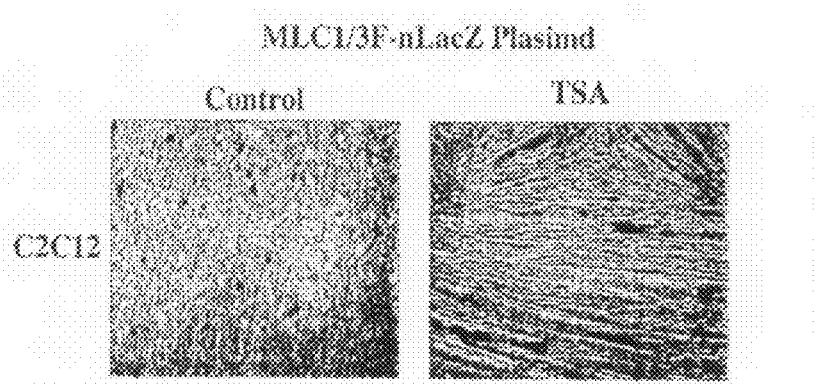
FIGS. 4A-C illustrate that embryos exposed to DI display enhanced somitogenesis and increased muscle gene expression.

The MLC3F-lacZ-nls construct was shown to be responsive to TSA treatment in cultured cells. As shown in FIG. 4A, cells transfected with the MLC3F-lacZ-nls construct and exposed to either TSA or VPA (data not shown) displayed increased β-galactosidase-positive nuclei when compared to non-treated cells.

Figure 4B:
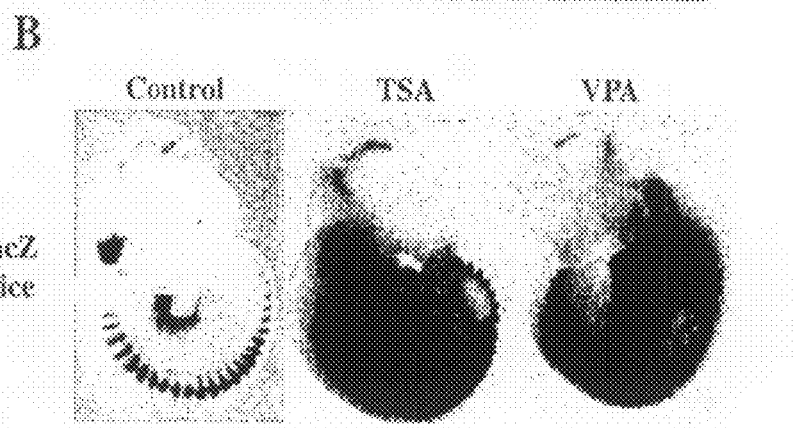

Mouse embryos treated with TSA at E 8.5 and sacrificed at E 9.5 during somitogenesis were modestly and consistently larger than control embryos and presented an increased (+2 to +6) number of somites. This correlated with increased acetylation of histone H4 and number of somites expressing the myogenic factor Myf-5. Since MyoD is not expressed at E 9.5, the in vivo effect of TSA and VPA was analyzed. DI was administered intraperitoneally to pregnant mice (at a concentration of 0.5 to 1 mg/Kg for TSA and 200 mg/Kg for VPA) at post-implantation stages of E 8.5, and the pregnant mice were sacrificed at 10.5, when MyoD expression is clearly detectable in the myotomes. As illustrated in FIG. 4 and Table 2, the number of MLC expressing somites (revealed in blue by β-galactosidase staining in FIG. 4B), and the number of MyoD expressing myotomes (panel B) were consistently increased in TSA and VPA treated embryos. In Table 2, Somites of MLC1/3F-nLacZ mice (injected at day 8.5 and sacrificed at day 10.5) were scored after staining the embryos to detect β-galactosidase activity.

TABLE 2

TSA and VPA Anticipate Somitogenesis in Developing Embryos

| Controls (PBS) (# somites) | TSA [1 mg/ml] (20 ul + 380 ul PBS) (# somites) | VPA 155 mM (# somites) |
| --- | --- | --- |
| 25 | 33 | 34 |
| 25 | 36 | 33 |
| 27 | 32 | 36 |
| 27 | 32 | 34 |
| 32 | 32 | 35 |
| 31 | 37 | 36 |
| 30 | 34 | 33 |
| 32 | 36 | 33 |
| 30 | NE | 33 |
| 32 | NE | 36 |
| NE | NE | 34 |
| NE | NE | 34 |

"NE" = not evaluated.

Figure 4C:
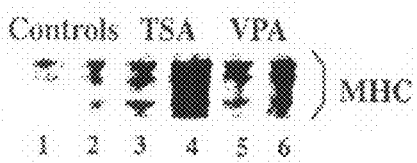

Furthermore, as shown in FIG. 4C, TSA and VPA treatment also augmented the levels of MHC in the exposed embryos.

These results show that DI treatment during the post-implantation stage, when certain morphogenetic events occur, results in accelerated formation of somites and increased myosin levels, as observed in cultured cells.

Example 2

Class I Histone Deacetylases Sequentially Interact with MyoD and pRb During Skeletal Myogenesis A functional and biochemical link exists among the myogenic activator MyoD, the deacetylase HDAC1, and the tumor suppressor pRb. Interaction of MyoD with HDAC1 in undifferentiated myoblasts mediates repression of muscle-specific gene expression. Pro-differentiation cues, mimicked by serum removal, induce both downregulation of HDAC1 protein and pRb hypophosphorylation. Dephosphorylation of pRb promotes the formation of pRb-HDAC1 complex in differentiated myotubes. pRb-HDAC1 association coincides with interference with the MyoD-HDAC1 interaction, transcriptional activation of muscle-restricted genes, and cellular differentiation of skeletal myoblasts. A single-point mutation introduced in the HDAC1-binding domain of pRb obstructs its ability to disrupt MyoD-HDAC1 interaction and to promote muscle-gene expression. Thus, reduced expression of HDAC1, accompanied by its redistribution in alternative nuclear protein complexes, is involved in terminal differentiation of skeletal muscle cells.

Cells, Plasmids, Transfections and Luciferase Reporter Assay

C2C12, 3T3 and C3H10T1/2 cells were cultured as previously described. See Puri et al. (1997a) and Sartorelli et al. (1997). Rb−/−MD3 and cells were provided by Dr. Lassar. Rb−/−p53±double knock out derived 3T3 fibroblasts were established as previously described Chen, T. T., and Wang, Y. J., *Mole Cell Biol.* 20:5571-80 (2000). Transient transfections were performed using the calcium-phosphate precipitation method, lipofectamine (Life Technologies), or FuGENE 6 transfection reagent (Roche Molecular Biochemicals). The MCK-luc, 4RE-luc, MEF2-luc, CMV-MyoD and CMV-MEF2C, Gal-MyoD and Myo-E47 constructs are described in Puri et al. (1997a) and Sartorelli et al. (1997). The vectors expressing Myc-HDAC4 and mutant Myc-HDAC4D840N were provided by Dr. Kouzarides and are described in Miska, E. A., et al., *EMBO Journal* 18:5099-107 (1999). The vectors expressing Flag-HDAC1, mutant Flag-HDAC1D174N-D176N and Flag-HDAC2 were provided by Dr. Schreiber and are described in Taunton et al. (1996). The vector expressing HDAC1 ΔIACEE was provided by Dr. Harel-Bellan and is described in Magnaghi et al. (1998). The vectors expressing pRb and mutants pRb (N757F), pRb (PMS.91) and pRb (PMS.91-N757F) are described in Chen and Wang (2000). The vector expressing E2F1-pRb(SP) was provided by Dr. Kaelin and is described in Sellers, W. R., et al. *Genes Dev.* 12:95-106 (1998). Following transfections, luciferase activity was determined using the Dual-Luciferase reporter assay system (Promega) on a microtiter luminescence detection system (MLX, Dynex). Luciferase assays were done in triplicate points and repeated 3-5 times.

Immunoprecipitation, Immunoblotting and Immunofluorescence

To detect interactions between pRb, HDAC1 and MyoD by co-immunoprecipitation (co-IP), C2C12 cells and pRb-deficient myogenic cells (either MD3 cells or MyoD converted 3T3 pRb−/−p53±), were either grown in GM or induced to differentiate in DM. Cells were harvested and lysed in buffer containing 50 mM Tris HCl pH 8, 125 mM NaCl, 1 mM DTT, 5 mM $MgCl_2$, 1 mM EDTA, 10% glycerol, 0.1%, NP40 supplemented with 1 mM PMSF, proteases inhibitors mix, 1 mM Na3OV4, 10 mM β-glycerophosphate, 1 mM sodium pyrophosphate, 10 mM NaF, 10 mM sodium butyrate. After 30 minutes in ice, lysates were sonicated and 5 mg (myoblasts) or 10 mg (myotubes) of extract was processed for IP with a mixture of anti-HDAC1 polyclonal antibodies from Upstate Biotech and Santa Cruz Biotechnologies or anti-pRb 851. Co-precipitated MyoD and pRb were revealed by anti-MyoD 5.8 (Novocastra) or anti-pRb 851, respectively. To detect HDAC1 associated with pRb, C2C12 extracts were immunoprecipitated with pRb G3-245 monoclonal antibody (PharMingen) as described in Magnaghi et al. (1998) and HDAC1 was revealed in Western blot with anti-HDAC1 polyclonal antibody (Upstate Biotech.). For immunoblotting, cell extracts were obtained after incubating the cells in standard lysis buffer. Western blots were probed with the following antibodies: anti-FLAG-M2 (Sigma), anti-MHC MF-20, anti-cyclin A, (Upstate Biotech.), anti-myogenin FD5, anti-MEF2 (Santa Cruz Biotech.) anti-p21 (Calbiochem), anti-MyoD polyclonal M-318 (Santa Cruz Biotech), anti-MyoD monoclonal 5.8 (Novocastra), anti-HDAC1-2-4-5 (Santa Cruz Biotech.), anti-pRb 851 and anti-tubulin E7 (Developmental Studies Hybridoma Bank, University of Iowa). Primary antibodies were visualized with the ECL (Amersham) chemoluminescent kit.

For immunofluorescence studies, cells were co-transfected with the plasmid of interest and a GFP-encoding plasmid, to localize productively transfected cells. After exposure to DM, cells were fixed and stained with the following antibodies: MF-20 (anti-MHC), and myogenin FD5. Green fluorescent signal in GFP-transfected cells was preserved by fixation with 2.8% formalin buffer. Nuclei were visualized by 4',6'-diamino-2-phenylindole (DAPI). FITC-conjugated or Texas red-conjugated secondary antibodies were employed to reveal the primary antibodies.

Muscle Creatine Kinase Assay

The activity of endogenous muscle creatine kinase in C2C12 muscle cells was measured following the procedures of the commercial kit from Sigma. Cells were washed in TBS and the cell extracts used for the assay were prepared in TBS-containing buffer with 1% Tween, phosphatase, and proteases inhibitors.

In Vitro Pull-Down Assay and Co-Immunoprecipitation

FLAG-HDAC1 and FLAG-pRb were baculovirus expressed and affinity purified as described in Sartorelli et al. (1999). His-MyoD was expressed in bacteria and purified as described in Sartorelli et al. (1999). For the interaction between HDAC1 and pRb, 3 pmol of FLAG-pRb were incubated with 8 pmol of HDAC1 in 0.2 ml of NETN buffer (20 mM Tris-HCl, pH 8.0; 150 mM NaCl, 0.5% NP-40, 1 mM EDTA, 1 mM PMSF) for 15 min on ice in the presence of 1 μg of bovine serum albumin. After adding 1 μg of HDAC1 antiserum (Upstate Biotech.), the reaction was incubated for 60 min at +4° C. on a rotating wheel. Protein A agarose (20 μl) was added and incubation continued for additional 60 min. Agarose beads were collected by centrifugation, washed four times with 1 ml of NETN each time, boiled, and proteins were analyzed on 4%-20% gradient SDS-PAGE. Immunoblot was performed with M2 anti-FLAG antibody (Kodak) and protein detected with the ECL cheminoluminescent kit (Amersham). For HDAC1-MyoD interaction, HDAC1 was 3 pmol and His-MyoD 10 pmol. For competition experiments, His-MyoD (10 pmol or 20 pmol) was added to the reaction and immunoblot performed with anti-MyoD 5.8 antibody (Novocastra). GST-Rb (WT) and GST-Rb (N757F) were expressed in bacteria and purified as described in Chen and Wang (2000). Rb−/− 3T3 cells were co-transfected with plasmids expressing myc-tagged MyoD and Flag-tagged HDAC1 using Superfect (Quiagen). Total cell lysate was prepared 48 hours after transfection in lysis buffer. Aliquots of an equal amount of total cell lysate were incubated with an increasing amount of GST-RB (WT) or GST-RB (N757F) for 2 hours at 4° C. Bound proteins were recovered by centrifugation at 14,000 rpm for 30 seconds at 4° C. and analyzed by immunoblots using anti-Flag antibody to detect HDAC1. The supernatants were transferred to new tubes and incubated with anti-Flag antibody for 2 hours at 4° C. Protein G conjugated to agarose was then added and the incubation continued for another 1 hour at 4° C. At the end of incubation, bound proteins were collected by centrifugation at 10,000 rpm for 30 seconds and washed three times with lysis buffer. Precipitated proteins were analyzed by immunoblots using anti-Flag or anti-myc antibodies.

Deacetylation Assay

The deacetylation assay was performed with a histone deacetylase assay kit purchased by Upstate Biotechnology. C2C12 nuclear extracts were prepared according to the manufacturer's instructions. Two hundred micrograms of nuclear extracts were precleared and immunoprecipitated with the 4 µg of the indicated antibodies for 3 h and subsequently washed three times in buffer A (20 mM Tris/Cl pH-7.6; 150 mM NaCl, 5 mM MgCL2; 10% Glycerol; 0.1% IPGAL). The purified proteins were incubated with 80,000 cpm of $^3$H-acetylated H4 peptide in 200 µl assay buffer for 3 h at 30° C. Sodium butyrate (20-50 mM) or 100 nM trichostatin A (TSA) (WAKO, USA) were employed as deacetylase inhibitors. Free $^3$H-acetyl was determined with liquid scintillation counting and results were adjusted to background.

HDAC1 Associates with MyoD in Undifferentiated Myoblasts and with Hypophosphorylated pRb in Differentiated Myotubes.

Figure 5A:
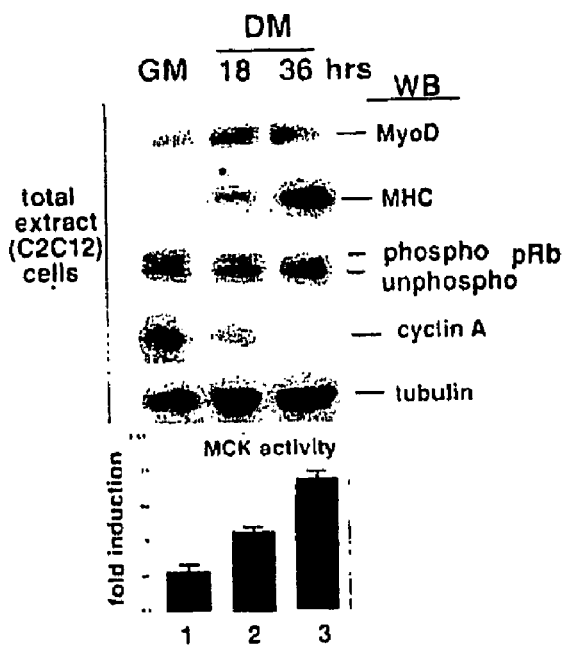
Figure 5B:
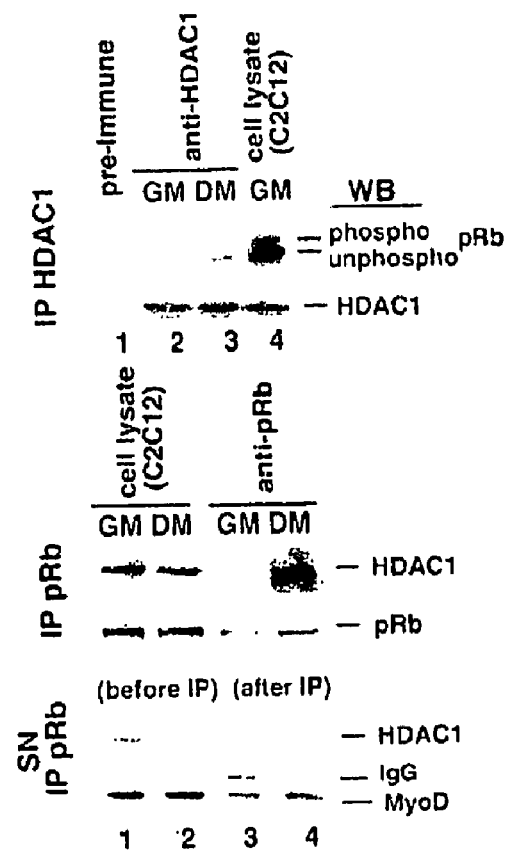
Figure 6A:
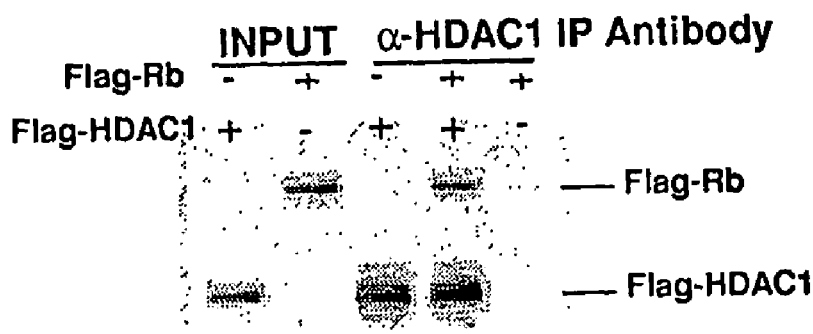
FIGS. 6A-E illustrate the in vitro interaction of pRb and MyoD with HDAC1.
Figure 6B:
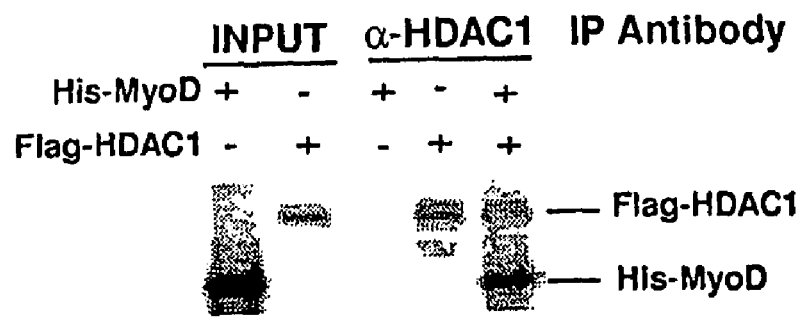
Figure 6C:
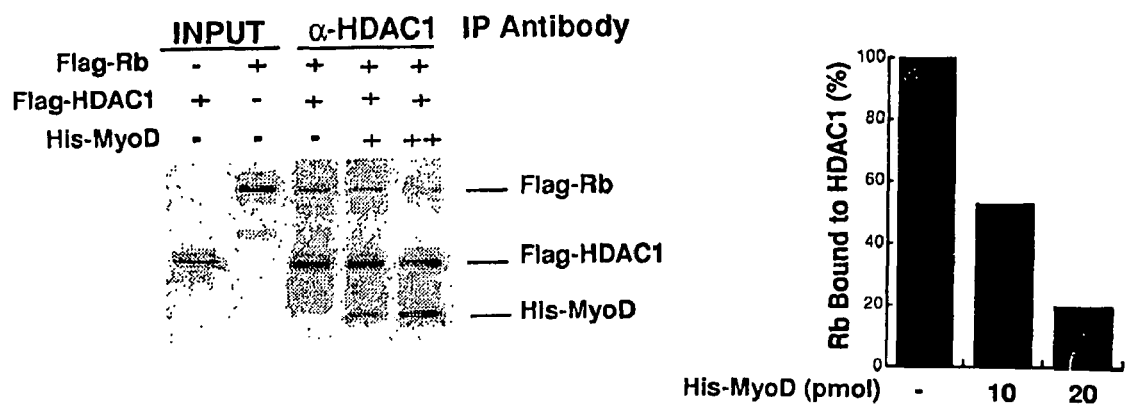
Figure 6D:
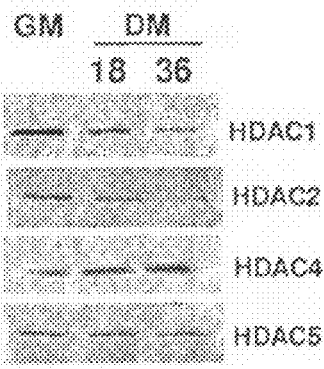
Figure 6E:
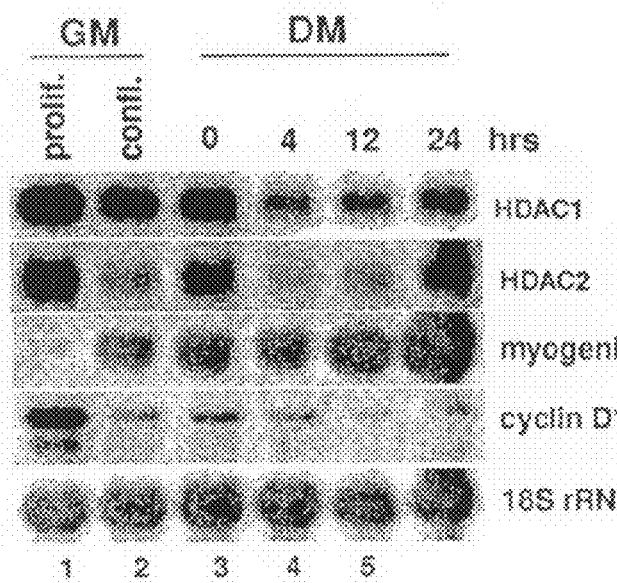

In growth-arrested cells, the recruitment of HDAC1 by hypophosphorylated pRb mediates transcriptional repression of E2F-dependent genes involved in cell cycle progression. See, e.g., Harbour, J. S. and Dean, D. C., *Genes Dev.* 14:2393-2409 (2000a). In skeletal muscle cells induced to differentiate by serum withdrawal (differentiation medium), pRb dephosphorylation coincides with repression of cell cycle promoting genes, such as cyclin A, as well as the expression of late muscle-restricted genes, such as MHC and MCK (FIG. 5A). Under these conditions, only hypophosphorylated pRb can be co-precipitated with HDAC1 (FIG. 5B, upper panel, IP HDAC1, lane 3). To perform the complementary experiment, pRb was immunoprecipitated and it was confirmed that HDAC1-pRb complex could be detected in myotubes (FIG. 5B, lower panel, IP pRb, lane 4). To verify that HDAC1 was co-immunoprecipitated by pRb derived from myotubes (i.e., hypophosphorylated pRb, FIG. 5A), the supernatants were analyzed—following pRb immunoprecipitation—for the presence of HDAC1. The supernatant derived from the pRb immunoprecipitation conducted with differentiated myotube extracts was depleted of –70% of the cellular HDAC1, as compared to that present in the extract prior immunoprecipitation. This indicates that, in myotubes, the large majority of HDAC1 is associated with pRb. In spite of the HDAC1 immunodepletion exerted by pRb antibodies (FIG. 5B lower panel, lane 4), the levels of MyoD present in the supernatant remain constant, suggesting that pRb does not interact with MyoD and that MyoD is not associated with the HDAC1-pRb complex in myotubes. Thus, repression of genes involved in cell cycle progression and activation of late myogenic markers correlate with the formation of pRb-HDAC1 complex. In contrast, HDAC1-pRb complex was not detected in proliferating myoblasts (FIG. 5B, upper panel, lane 2; lower panel, lane 3), a stage in which pRb is hyperphosphorylated (FIG. 5A). HDAC1 has been recently reported to interact with and repress the activity of MyoD. See Mal A., et al. *EMBO Journal* 20:1739-53 (2001). It was found that HDAC1 interacts with MyoD in myoblasts, but not in myotubes (FIG. 5C, lower panel, compare lanes 1 and 2). No association between pRb and MyoD could be detected in extracts from either myoblasts or myotubes. Thus, HDAC1-MyoD and HDAC1-pRb are distinct complexes that form at discrete stages of muscle differentiation. A similar pattern of interactions was also observed with HDAC2 (data not shown). Consistent with a sequential interaction of class I deacetylases with MyoD and pRb, the deacetylase activity co-immunoprecipitated with MyoD was higher in myoblasts as compared to myotubes, whereas pRb-associated deacetylase activity increased in differentiated muscle cells (FIG. 5D). MyoD and pRb do not interact with class H deacetylases. See Lu, J., et al. *Mol. Cell* 6:233-44 (2000), and Harbour and Dean (2000b) and HDAC1 was found associated with either MyoD or pRb in immunoprecipitates employed for deacetylase assays (FIG. 5D). To address whether the interaction between MyoD and HDAC1, and pRb and HDAC1 is direct, recombinant FLAG-HDAC1 and FLAG-pRb produced in a baculovirus expression system and recombinant His-MyoD generated in bacteria were employed. As shown in FIGS. 6A and 6B, respectively, HDAC1 binds to pRb and MyoD. Competition experiments were performed with constant amounts of both FLAG-HDAC1 and FLAG-pRb and increasing concentrations of His-MyoD. The interaction between HDAC1 and pRb was inhibited in a dose-dependent manner by addition of MyoD (FIG. 6C). This in vitro evidence, together with the mutually exclusive formation of HDAC1-MyoD and HDAC1-pRb complexes in myoblasts and myotubes, respectively, (FIG. 5B) demonstrate that HDAC1, MyoD, and pRb do not form a trimeric complex. HDAC1 levels were further monitored during skeletal muscle differentiation. Unlike class II deacetylases HDAC4 and 5, whose protein levels are constant during the differentiation program (FIG. 5A and Lu et al. (2000), class I deacetylases HDAC1 and 2 declined in muscle cells placed in DM (FIG. 5A). A Northern blot analysis revealed that reduction of HDAC1 and 2 levels occurs at the RNA level either after cell confluence or serum removal (DM), two conditions associated to downregulation of muscle inhibitors (e.g. cyclin DI) and up-regulation of markers of myogenic differentiation (e.g. myogenin) (FIG. 6E).

These results collectively indicate that downregulation of class I deacetylases and their sequential interaction with MyoD—in myoblasts—and hypophosphorylated pRb—in myotubes—is involved in the control of the expression of late muscle-restricted genes.

HDAC1 Represses Late-Muscle Gene Expression

Forced expression of class I deacetylases can interfere with the activation of those genes (e.g. MCK and MHC), whose expression requires the presence of functional pRb. Indeed, forced expression of either HDAC1 or 2 in MyoD-converted 10T1/2 fibroblasts led to a partial suppression of muscle-specific gene expression, with lack of inhibition on early differentiation markers, such as myogenin, but reduced expression of late differentiation genes, such as MHC (Table 3). In Table 3, 10T1/2 cells were converted into muscle cells by ectopic expression of MyoD with or without coexpression of HDAC1, 2, or 4. A vector encoding GFP was employed to allow identification of transfected cells. After fixation in paraformaldehyde, productively transfected cells were visualized by the expression of cotransfected GFP. Myogenic conversion was scored by determining the expression of two differentiation markers (myogenin and MHC) in GFP-positive cells. Only multinucleated cells (with two or more nuclei) were considered positive.

TABLE 3

HDAC Overexpression Inhibits MHC Expression

| | Percentage Positive Cells | | | |
|---|---|---|---|---|
| | Myog | | MyoD | |
| | Trial #1 | Trial #2 | Trial #1 | Trial #2 |
| Empty Vector | <1 | <1 | <1 | <1 |
| MyoD | 52 | 41 | 23 | 25 |
| MyoD + HDAC1 | 45 | 44 | 10 | 11 |
| MyoD + HDAC2 | 50 | 44 | 12 | 9 |
| MyoD + HDAC4 | 15 | 12 | 7 | 10 |

Figure 8A:
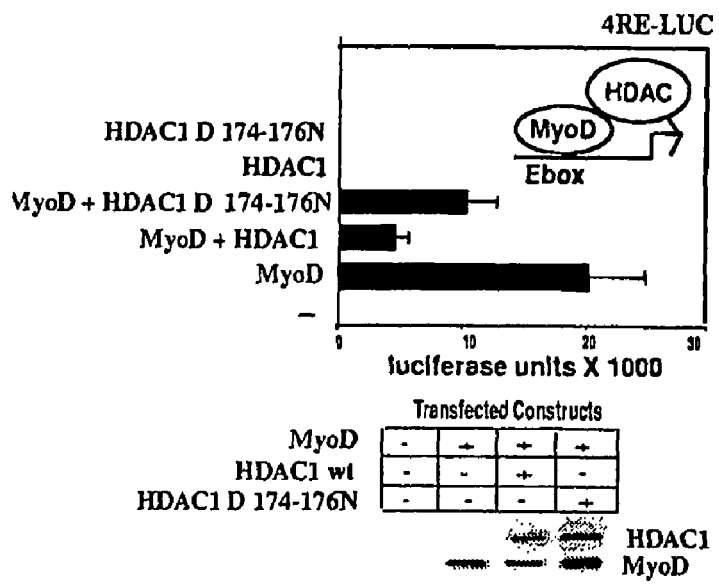
FIGS. 8A-G show that HDAC1 suppresses MyoD-mediated, and not MEF2-mediated transcription. Cells were placed in DM 48 hr after transfection and were harvested after 48 hr for luciferase activity.
Figure 8B:
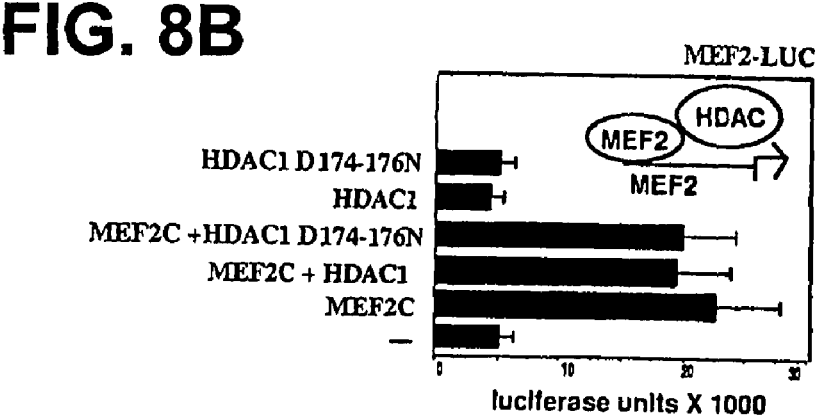
Figure 8C:
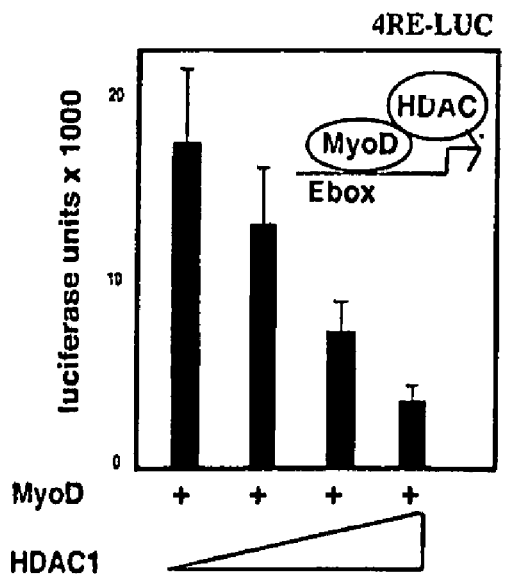
Figure 8D:
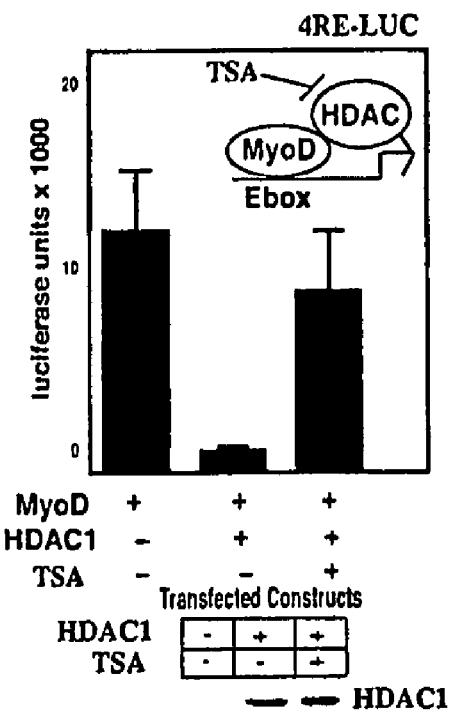
Figure 8E:
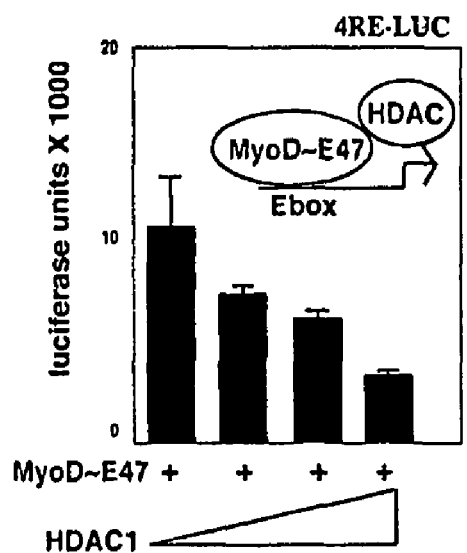
Figure 8F:
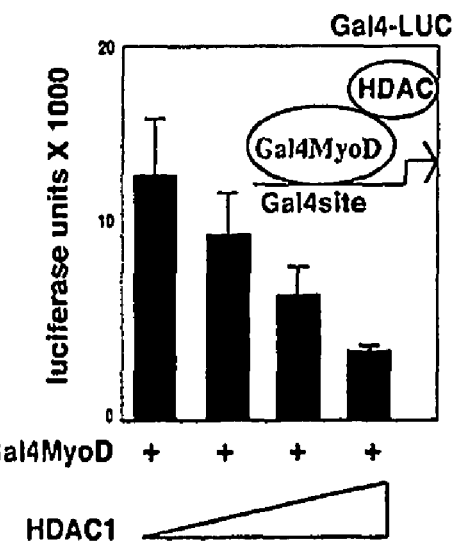

A similar pattern of myogenic repression was also observed in C2C12 muscle cells. The molecular and phenotypic consequences of HDAC-1 and 2 overexpression in myogenic cells are reminiscent of those observed in myocytes derived from pRb−/− mice, further indicating a functional link between these two proteins in regulating the expression of certain muscle-specific genes. Activation of muscle-specific gene expression occurs following induction of both myogenic bHLH and MEF2-mediated transcription. Therefore the effect of HDAC1 on the activation of reporter constructs containing either four repeated MyoD-binding sites (4RE-luc) or two MEF2-binding sites (MEF2-luc) was evaluated. Transfection of MyoD and MEF2C in 10T1/2 fibroblasts activated the 4RE-luc and MEF2-luc reporters, respectively (FIGS. 8A and 8B). HDAC1 overexpression abrogated MyoD-dependent activation of 4RE-luc (FIG. 8A), but had no relevant effect on MEF2-dependent transcription (FIG. 8B), consistent with the lack of interaction between class I deacetylases and MEF2 members. Importantly, HDAC1 inhibited MyoD-dependent transcription in a dose dependent manner (FIG. 8C). A similar effect on MyoD-mediated transcription was observed with HDAC2 and, to a much less extent, with HDAC3 (data not shown). HDAC-mediated inhibition of both MyoD and MEF2C was dependent on the integrity of the enzymatic function, since mutations that abolished HDAC1 (HDAC1D174N-D176N) and HDAC4 (HDAC4D840N) deacetylase activity reduced their ability to repress MyoD and MEF2C, respectively (FIGS. 8A and 8B). The residual activity of these mutants can be due to their ability to dimerize with endogenous HDACs.

Figure 8G:
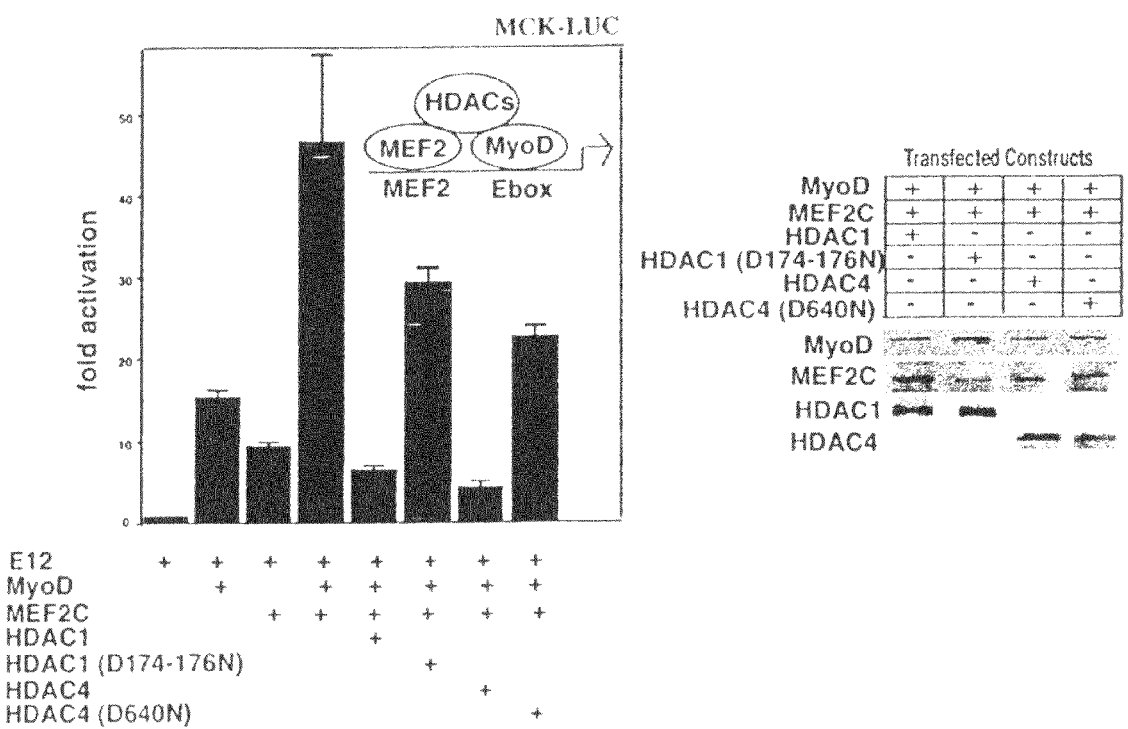

Previous reports have documented the functional synergism between myogenic bHLH proteins and MEF2 members in the activation of promoters/enhancers regulated by both E-box and MEF2 sites. See, e.g., Molkentin, J. D., and Olson, E. N., *Proc. Natl. Acad Sci. USA* 87:9366-73 (1996) and Novitch, B. G., et al., *Current Biology* 9:449-59 (1999). For instance, the regulatory region of the MCK gene contains both E-box and MEF2 sites and a MCK-luc reporter is synergistically activated in fibroblasts by the ectopic expression of MyoD, E12 and MEF2C. As shown in FIG. 8G, co-expression of either HDAC1 or HDAC4 abrogates the synergistic activation of the MCK promoter by MyoD and MEF2C. Thus, recruitment of class I or class II histone deacetylases by either MyoD or MEF2C can suppress the cooperation between these regulators in activating muscle-specific genes.

Figure 9A:
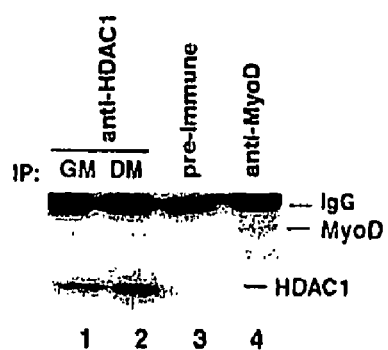
FIGS. 9A-E show that MyoD-HDAC1 interactions are disrupted by pRbwt, but not by a pRb mutant impaired in associating with HDAC1 and in promoting MyoD activity (pRb N757F).

A pRb Mutant (pRb N757F) Incapable of Associating with HDAC1 is Impaired in Promoting MyoD-Dependent Transcription in pRb-Deficient Myocytes The data presented in the previous sections indicated that, in the absence of pRb, the MyoD-HDAC1 interaction might be detectable even when these cells are cultured in DM. The MyoD-HDAC1 interaction was detected by immunoprecipiting HDAC1 from extracts derived from Rb−/−myogenic cells cultured either in GM or DM. Unlike in normal (pRb wt) muscle cells (see FIG. 5B), a MyoD-HDAC1 interaction was detectable in pRb−/−muscle cells cultured either in GM or in DM (FIG. 9A). The same interaction was observed in other pRb-deficient muscle cell lines, such as CC42 cells (data not show). Thus, the absence of pRb is permissive for the initiation of a MyoD-HDAC1 interaction, even when cells are placed in DM, indicating that pRb is involved in the displacement of HDAC1 from MyoD once cells are induced to differentiate.

Figure 9B:
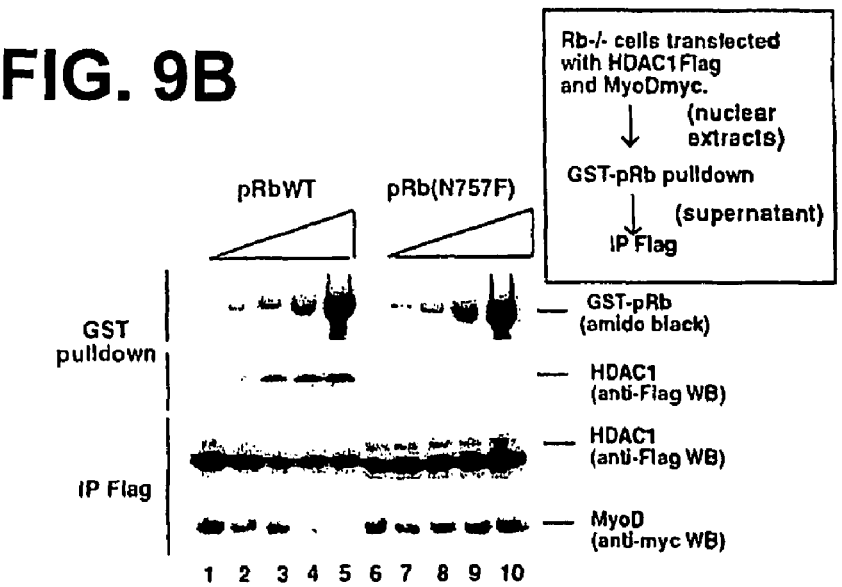
Figure 9C:
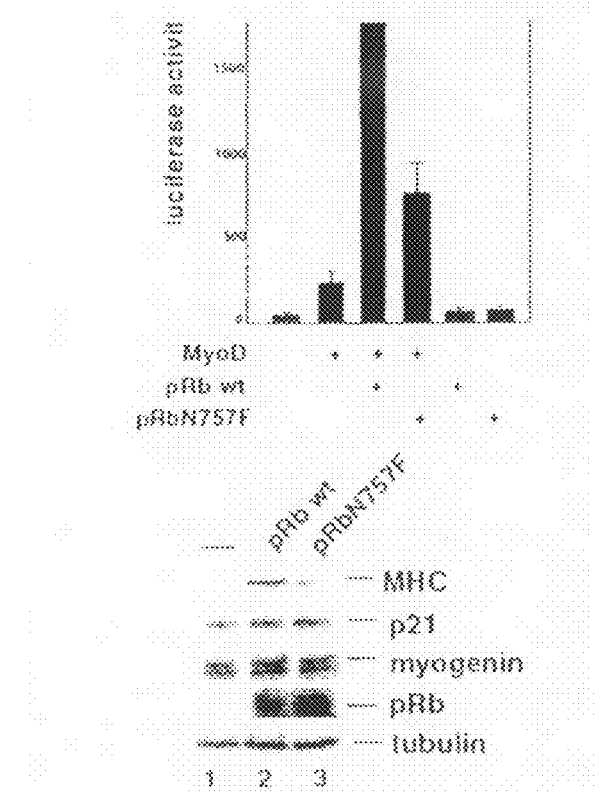

The ability of pRb wild type (wt) was compared to the ability of a pRb point mutant (N757F) impaired in HDAC1 binding (Chen and Wang, 2000) to interfere with the HDAC1-MyoD interaction as well as to restore MyoD transcriptional activity. The specificity for HDAC1 binding of pRb wt and pRb (N757F) was first tested in an in vitro-in vivo binding assay. Flag-HDAC1 and a myc-MyoD vectors were expressed in pRb−/−3T3 cells and their interaction was verified by performing an anti-Flag immunoprecipitation followed by Western blot with an anti-myc antibody (FIG. 9B). When the extracts were pre-incubated with increasing amounts of either GST-pRb wt or GST-pRb (N575F), HDAC1 was recovered only in GST-pRb wt complexes (FIG. 9B, GST-pulldown panels, compare lanes 1 to 5 with 6 to 10). In contrast, no MyoD signal was detected either in GST-pRb wt or in N757F precipitates, and MyoD levels were comparable in the supernatant derived from both GST precipitates (data not shown). Immunoprecipitation with anti-Flag from the supernatants obtained after incubation with the GST-pRb fusion proteins, revealed the presence of MyoD-HDAC1 complexes only in the extracts pre-incubated with GST-pRb (N757F) (FIG. 9B, IP Flag panels, lanes 6 to 10). These results indicate that a pRb mutant incapable of associating with HDAC1 does not displace HDAC-1 from MyoD. The activity of the pRb wt and pRb (N757F) mutant was further investigated in vivo by comparing the efficiency of pRb wt versus pRb N757F in restoring MyoD-dependent transcription and expression of late myogenic markers in pRb−/−cells. For this purpose, pRb−/−3T3 fibroblasts were transfected with MyoD and the MCK-luc reporter. In the absence of pRb, MyoD did not efficiently activate MCK-luc (FIG. 9C) and induced low amounts of MHC (FIG. 9C, lower panel, lane 1). Reconstitution of these cells with pRb wt could restore MCK-luc activity (FIG. 9C) as well as the expression of MHC (FIG. 9C, lower panel, lane 2), whereas reintroduction of pRb N757F failed to do so (FIG. 9C, and lower panel, lane 3). In contrast, expression levels of early myogenic markers, p21 and myogenin, were efficiently stimulated by MyoD in the absence of pRb and did not change with the reintroduction of either pRb wt or N757F (FIG. 9C, lower panel). These results demonstrate that the failure to activate transcription of late myogenic markers in pRb−/−myocytes by MyoD is attributable to the persistent initiation of a MyoD-HDAC1 interaction, due to a lack of HDAC1 interaction with pRb. Notably, despite the inability to fully rescue the transcription of late myogenic markers (e.g. MCK and MHC), pRb N757F was competent to restore fusion of pRb −/−MD3 myoblasts into myotubes (Chen and Wang, 2000) (and data not shown).

Figure 9D:
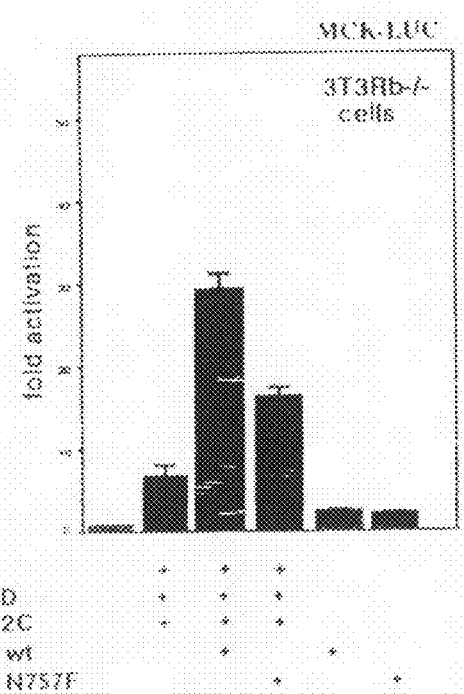
Figure 9E:
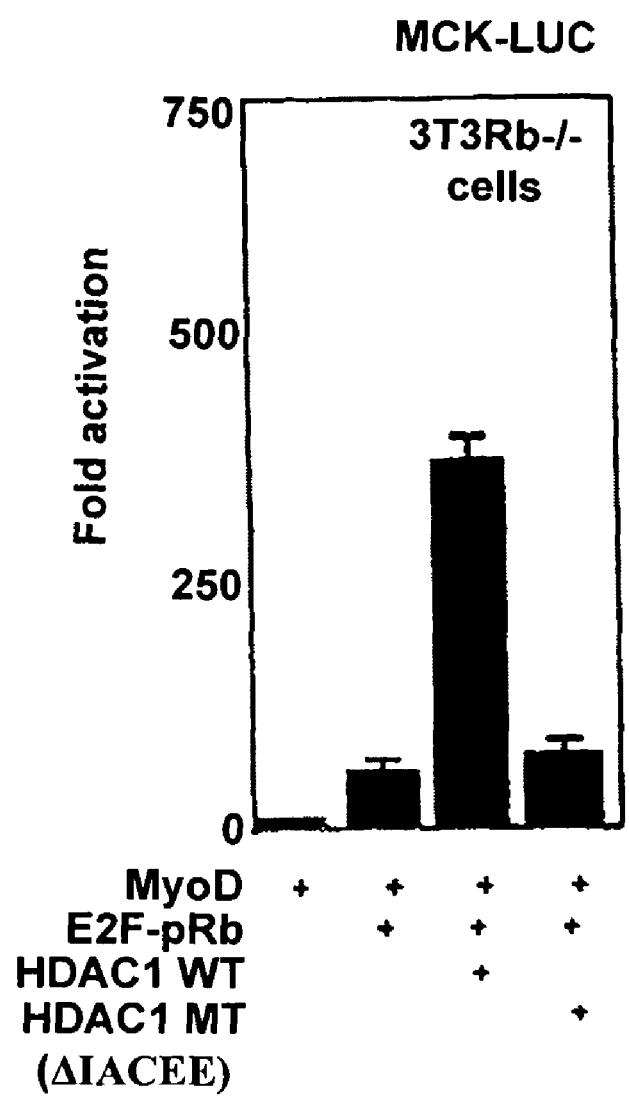

The ability of pRb wt was compared to the ability of pRb N757F to rescue the cooperative activation of MCK-luc by MyoD and MEF2C in pRb−/−fibroblasts. Again, the efficiency of pRb N757F in promoting MyoD-MEF2 synergism was much reduced as compared to pRb wt (FIG. 9D), indicating that HDAC1 binding is an important event in pRb-mediated activation of MyoD-MEF2C synergism.

The interaction of pRb with HDAC1 can concomitantly achieve two independent, yet functionally coherent, effects: i) displacement of HDAC1 from MyoD (FIG. 6C and FIG. 9B) and ii) recruitment of the HDAC1-pRb complex to actively regulate muscle-specific transcription by repressing of genes favoring cell cycle progression. The second effect can be demonstrated with the E2F1-pRb(SP) construct expressing a chimeric protein consisting of the DNA-binding domain of E2F1 fused to the small pocket (amino acids 379-797) of pRb. The E2F1-pRb(SP) construct has been shown to coactivate MyoD-dependent transcription and block cell cycle progression (Novitch et al., 1999). pRb−/−cells were transfected with MCK-luc and different combinations of MyoD, E2F1-pRb (SP), HDAC1 and HDAC1 ΔIACEE, a mutant impaired in associating with pRb (Magnaghi et al., 1998). HDAC1 augmented the ability of E2F1-pRb(SP) to coactivate MyoD-dependent transcription, whereas HDAC1 ΔIACEE failed to do so (FIG. 5E).

pRb Dephosphorylation is Required to Interfere with the HDAC1-MyoD Interaction and to Activate Muscle-Gene Expression Since HDAC1 selectively interacts with hypophosphorylated pRb (FIG. 5B), a non-phosphorylatable pRb mutant (pRb-PSM 91) (Knudsen et al. 1997) constitutively displaces HDAC1 from MyoD and therefore activate MyoD even in the presence of serum. Reconstitution of pRb-deficient myogenic MD3 cells with pRb-PSM 91 restored MyoD-dependent transcription more efficiently than pRb wt in the presence of serum (FIG. 10A). To further address the interplay between pRb phosphorylation and HDAC1-binding, a pRb mutant incapable of both interacting with HDAC1 and being phosphorylated was devised (pRb-PSM 91-N757F). This pRb mutant displayed a reduced efficiency in rescuing MyoD-dependent transcription in the presence of serum (FIG. 10A) as compared to the non-phosphorylatable pRb form (pRb-PSM 91). The different efficiency displayed by the two pRb mutants, pRb-PSM 91 and pRb-PSM 91-N757F, in restoring MyoD function in the presence of serum correlated with their different ability to interfere with the MyoD-HDAC1 interaction in MD3 cells cultured in high serum (GM) (FIG. 10B). Only pRb-PSM 91 disrupted the interaction between endogenous MyoD and overexpressed HDAC1 (FIG. 10B, lane 3). In contrast, pRb wt undergoes hyperphosphorylation, as a consequence of high mitogens contained in the serum, and could not displace MyoD-HDAC1 interaction. Similarly, either pRb-N757F-PMS91 or the pRb N757F mutants failed to dissociate MyoD-HDAC1 interaction, regardless of their phosphorylation status (FIG. 10B, lanes 4 and 5). Thus, both pRb dephosphorylation and intact HDAC1-binding domain are involved in the pRb-mediated dissociation of the MyoD-HDAC1 interaction and activation of MyoD-dependent transcription.

pRb dephosphorylation in differentiating muscle cells occurs upon the simultaneous upregulation of cdk-inhibitors (cdki) and the downregulation of cyclin-cdk activity. Modulation of pRb phosphorylation by overexpression of cdki can affect the ability of pRb to restore MyoD function. Co-transfection of both cdki p21 and p16 potentiated the ability of pRb wt, but not that of pRb-PMS 91 or pRbN757F mutants, in rescuing MyoD activity in the presence of serum (FIG. 10A). Since both pRb wt and pRb N757F undergo hypophosphorylation following cdki overexpression, their different abilities to stimulate MyoD activity in GM can be attributed to their capability of interacting (pRbwt) or not (pRb N757F) with HDACs. These results demonstrate that modulation of pRb phosphorylation by cyclin/cdks can indirectly affect the activity of MyoD by regulating its association with HDAC1.

Having illustrated and described the principles of several embodiments, it should be apparent that those embodiments can be modified in arrangement and detail without departing from the principles described. Thus, all such embodiments and their equivalents are considered to be encompassed herein.

We claim:

1. A method of enhancing progenitor cell differentiation, comprising contacting an undifferentiated progenitor cell with an effective amount of a deacetylase inhibitor for a period of time sufficient to induce progenitor cell differentiation.

2. The method according to claim 1, further comprising, once progenitor cell differentiation has been induced, removing a sufficient amount of the deacetylase inhibitor sufficient to allow further differentiation of the differentiated progenitor cell to occur.

3. The method according to claim 1 wherein the progenitor cell is a muscle progenitor cell, a neuronal progenitor cell, or a hematopoietic progenitor cell.

4. The method according to claim 1 wherein the progenitor cell comprises a cell culture.

5. The method according to claim 1 wherein the progenitor cell is located within an organism.

6. The method according to claim 1 wherein the progenitor cell is a mammalian progenitor cell.

7. The method according to claim 6 wherein the progenitor cell is a human progenitor cell.

8. The method according to claim 1 wherein the deacetylase inhibitor is an inhibitor of histone deacetylase.

9. The method according to claim 8 wherein the deacetylase inhibitor is an inhibitor of HDAC1.

10. The method according to claim 1 where the deacetylase inhibitor is sodium butyrate, trichostatin A, valproic acid, or a combination thereof.

11. The method according to claim 1 wherein the method is a method of enhancing myogenesis, neurogenesis, hematopoiesis, or a combination thereof.

12. The method according to claim 1, further comprising introducing a Rb or pRb protein into the cell.

13. A method of enhancing differentiation-related gene expression in a progenitor cell, comprising contacting a progenitor cell with a sufficient amount of an agent that inhibits a deacetylase for a period of time sufficient to enhance expression of the genes.

14. The method according to claim 13 wherein the progenitor cell is a myoblast, neuroblast, hematopoietic progenitor cell, or a combination thereof.

15. The method according to claim 14 wherein the progenitor cell is a myoblast.

16. The method according to claim 15 wherein contacting the myoblast with the agent enhances expression of muscle-specific genes.

17. The method according to claim 15 wherein the deacetylase is HDAC1 and, by inhibiting HDAC1, the agent interferes with the HDAC1/MyoD interaction in the myoblast.

18. The method according to claim 13 wherein the deacetylase is a histone deacetylase.

19. The method according to claim 18 wherein the deacetylase is HDAC1.

20. The method according to claim 13 wherein the agent is an effective amount of sodium butyrate, trichostatin A, valproic acid, or a combination thereof.

21. The method according to claim 13 wherein the agent is administered in a therapeutically effective amount to a subject to increase the rate of differentiation of a progenitor cell within the subject.

22. The method according to claim 21 wherein the subject is a mammal.

23. The method according to claim 22 wherein the subject is a human.

24. The method according to claim 22 wherein the subject is deficient in myogenesis, neurogenesis, hematopoiesis, or a combination thereof.

25. The method according to claim 13 wherein the agent is administered to a subject suffering a disease or condition associated with a loss of muscle tissue, nerve tissue, or hematopoietic tissue.

26. The method according to claim 25 wherein the disease or condition is associated with a loss of two or more of muscle tissue, nerve tissue, hematopoietic tissue, or a combination thereof.

27. The method according to claim 25 wherein the disease or condition is muscular atrophy, muscular dystrophy, muscular cachexia, dermatomyositis, Alzheimer's disease, olivopontocerebellar atrophy, Parkinson's disease, degeneration of nervous tissue, ocular atrophy, hepatocerebral degeneration, idiopathic aplastic anemia, secondary aplastic anemia, amyotrophic lateral sclerosis, poliomyolitis, bone marrow loss induced by radiation therapy or chemotherapy, multiple myeloma, acute lymphocytic leukemia, HIV infection, AIDS, malaria, chronic myelogenous leukemia, Fanconi's anemia, or trauma.

28. The method according to claim 27 wherein the disease or condition is muscular atrophy, muscular dystrophy, muscular cachexia, Alzheimer's disease, Parkinson's disease, idiopathic aplastic anemia, secondary aplastic anemia, bone marrow loss induced by radiation therapy or chemotherapy, or trauma.

29. The method according to claim 25 wherein the disease or condition is a disease or condition associated with degeneration of muscle tissue.

30. The method according to claim 13, further comprising introducing a Rb or pRb protein into the cell.

31. A method of treating a disease or condition associated with degeneration of muscle tissue, nerve tissue, or hematopoietic tissue, comprising:
    identifying a subject suffering a disease or condition associated with degeneration of muscle tissue, nerve tissue, or hematopoietic tissue; and
    administering to the subject a therapeutically effective amount of a deacetylase inhibitor to induce differentiation of progenitor cells which mature into muscle tissue, nerve tissue, or hematopoietic tissue.

32. The method according to claim 31 wherein the subject is a mammal.

33. The method according to claim 32 wherein the subject is a human.

34. The method according to claim 31 wherein the disease or condition is muscular atrophy, muscular dystrophy, muscular cachexia, dermatomyositis, Alzheimer's disease disease, olivopontocerebellar atrophy, Parkinson's disease, degeneration of nervous tissue, ocular atrophy, hepatocerebral degeneration, idiopathic aplastic anemia, secondary aplastic anemia, amyotrophic lateral sclerosis, poliomyolitis, bone marrow loss induced by radiation therapy or chemotherapy, multiple myeloma, acute lymphocytic leukemia, HIV infection, AIDS, malaria, chronic myelogenous leukemia, Fanconi's anemia, or trauma.

35. The method according to claim 34 wherein the disease or condition is muscular atrophy, muscular dystrophy, muscular cachexia, Alzheimer's disease, Parkinson's disease, idiopathic aplastic anemia, secondary aplastic anemia, bone marrow loss induced by radiation therapy or chemotherapy, or trauma.

36. The method according to claim 31 wherein the disease or condition is a disease or condition associated with degeneration of muscle tissue.

37. The method according to claim 31 wherein the deacetylase inhibitor is sodium butyrate, trichostatin A, or valproic acid.

38. The method according to claim 31 wherein the deacetylase inhibitor further comprises a pharmaceutically acceptable carrier, adjuvant, vehicle, or salt.

39. The method according to claim 31, further comprising administering to the subject a Rb or pRb protein.

40. A method of treating a deficiency in myogenesis, neurogenesis, or hematopoiesis, comprising:
    identifying a subject deficient in myogenesis, neurogenesis, or hematopoiesis; and
    administering to the subject a therapeutically effective amount of a deacetylase inhibitor.

41. The method according to claim 33 wherein the subject is a mammal.

42. The method according to claim 34 wherein the subject is a human.

43. The method according to claim 33 wherein the deacetylase inhibitor is sodium butyrate, trichostatin A, or valproic acid.

44. The method according to claim 33 wherein the deacetylase inhibitor comprises a pharmaceutically acceptable carrier, adjuvant, vehicle, or salt.

45. The method according to claim 33, further comprising administering to the subject a Rb or pRb protein.

* * * * *